US011365264B2

United States Patent
Theze et al.

(10) Patent No.: US 11,365,264 B2
(45) Date of Patent: Jun. 21, 2022

(54) THERAPEUTIC METHODS AND COMPOSITIONS

(71) Applicant: INSTITUT PASTEUR, Paris (FR)

(72) Inventors: Jacques Theze, Paris (FR); Thierry Rose, Paris (FR); Florence Bugault, Chartres (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 15/105,042

(22) PCT Filed: Dec. 22, 2014

(86) PCT No.: PCT/EP2014/078969
§ 371 (c)(1),
(2) Date: Jun. 16, 2016

(87) PCT Pub. No.: WO2015/097140
PCT Pub. Date: Jul. 2, 2015

(65) Prior Publication Data
US 2016/0311926 A1    Oct. 27, 2016

Related U.S. Application Data

(60) Provisional application No. 62/017,457, filed on Jun. 26, 2014, provisional application No. 61/920,137, filed on Dec. 23, 2013.

(30) Foreign Application Priority Data

Jun. 26, 2014 (EP) .................................. 14174599

(51) Int. Cl.
*C07K 16/40* (2006.01)
*A61K 39/38* (2006.01)

(52) U.S. Cl.
CPC .............. *C07K 16/40* (2013.01); *A61K 39/38* (2013.01); *C07K 2317/21* (2013.01); *C07K 2317/24* (2013.01); *C07K 2317/35* (2013.01); *C07K 2317/54* (2013.01); *C07K 2317/55* (2013.01); *C07K 2317/569* (2013.01); *C07K 2317/622* (2013.01); *C07K 2317/76* (2013.01); *C12Y 301/01004* (2013.01)

(58) Field of Classification Search
None
See application file for complete search history.

(56) References Cited

U.S. PATENT DOCUMENTS 9,000,132 B2 * 4/2015 Miller .................... C07K 16/40
424/133.1

FOREIGN PATENT DOCUMENTS

WO    WO 2004/002295       1/2004
WO    WO 2007/056279   *   5/2007 ............. A61K 47/48

OTHER PUBLICATIONS

Magrioti et al. (Expert Opin. Ther. Patents, 20(1):1-18, 2010).*
Donath et al. (Nature Reviews, Immunology, 11, 98-107, 2011).*
Stancovski et al. (PNAS, 88: 8691-8695, 1991).*
Jiang et al. (J. Biol. Chem., 280: 4656-4662, 2005).*
Limou, S. et al. "Exploration of associations between phospholipase A2 gene family polymorphisms and AIDS progression using the SNPlex™ method" *Biomedicine and Pharmacotherapy,* 2008, pp. 31-40, vol. 62, No. 1.
Seilhamer, J.J. et al. "Pancreatic Phospholipase A₂: Isolation of the Human Gene and cDNAs from Porcine Pancreas and Human Lung" *DNA,* Dec. 1, 1986, pp. 519-527, vol. 5, No. 6.
Xu, W. et al. "Structural Insight into the Activation Mechanism of Human Pancreatic Prophospholipase A2" *The Journal of Biological Chemistry,* Jun. 12, 2009, pp. 16659-16666, vol. 284, No. 24.
Written Opinion in International Application No. PCT/EP2014/078969, dated Apr. 24, 2015, pp. 1-6.

* cited by examiner

*Primary Examiner* — Nelson B Moseley, II
(74) *Attorney, Agent, or Firm* — Saliwanchik, Lloyd & Eisenschenk

(57) ABSTRACT

Methods for diagnosing or treating immune disorders in a subject are provided. The methods are based on the detection or modulation of Refractory state Inducing Factor (RIF).

16 Claims, 17 Drawing Sheets

Figure 1:
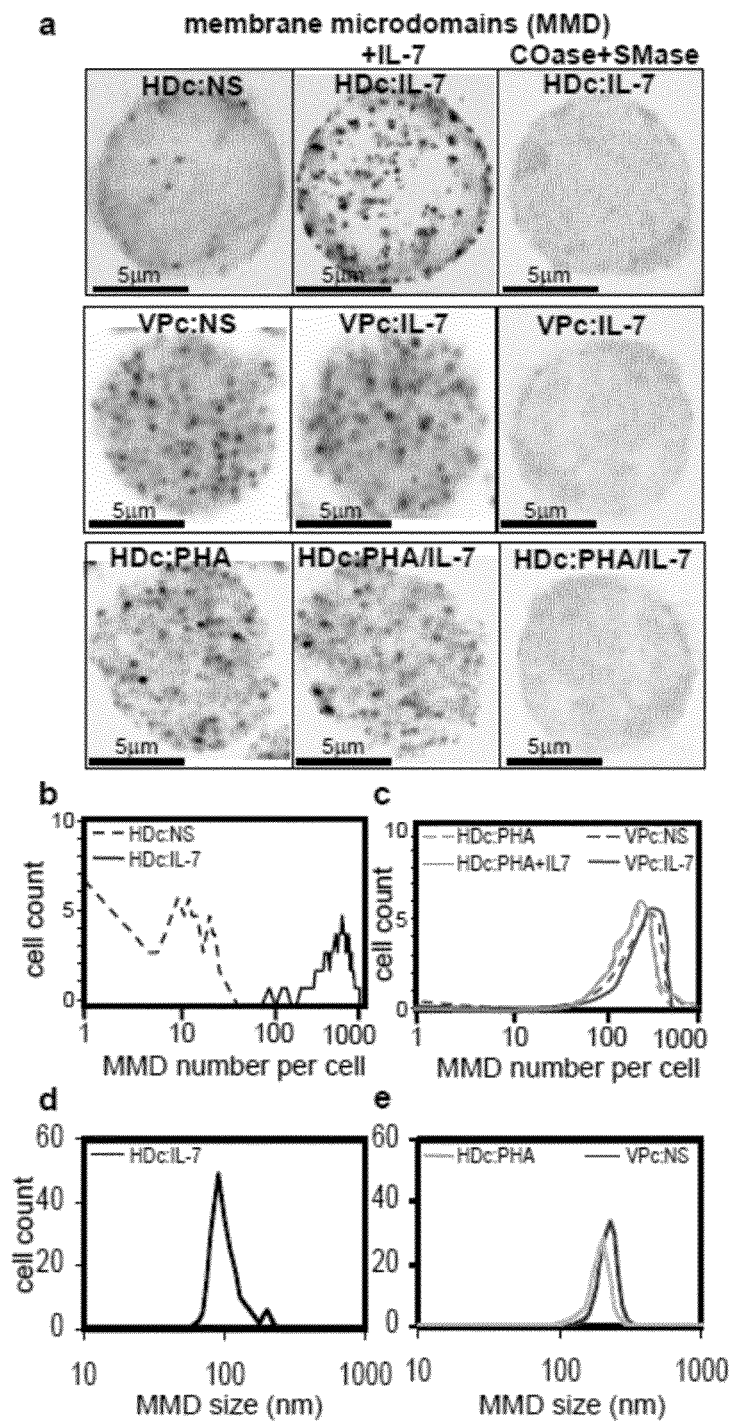

Specification includes a Sequence Listing.

a.

b.

SEQUENCE LISTING

<160> NUMBER OF SEQ ID NOS: 31

<210> SEQ ID NO 1
<211> LENGTH: 447
<212> TYPE: DNA
<213> ORGANISM: Artificial
<220> FEATURE:
<223> OTHER INFORMATION: cDNA encoding hGIBsPLA2

<400> SEQUENCE: 1

```
atgaaactcc ttgtgctagc tgtgctgctc acagtggccg ccgccgacag cggcatcagc      60
cctcgggccg tgtggcagtt ccgcaaaatg atcaagtgcg tgatcccggg gagtgacccc     120
ttcttggaat acaacaacta cggctgctac tgtggcttgg ggggctcagg cacccccgtg     180
gatgaactgg acaagtgctg ccagacacat gacaactgct acgaccaggc caagaagctg     240
gacagctgta aatttctgct ggacaacccg tacacccaca cctattcata ctcgtgctct     300
ggctcggcaa tcacctgtag cagcaaaaac aaagagtgtg aggccttcat ttgcaactgc     360
gaccgcaacg ctgccatctg cttttcaaaa gctccatata caaggcaca caagaacctg     420 gacaccaaga agtattgtca gagttga                                        447
```

<210> SEQ ID NO 2
<211> LENGTH: 148
<212> TYPE: PRT
<213> ORGANISM: Artificial
<220> FEATURE:
<223> OTHER INFORMATION: hGIBsPLA2

<400> SEQUENCE: 2

```
Met Lys Leu Leu Val Leu Ala Val Leu Leu Thr Val Ala Ala Ala Asp
1               5                   10                  15

Ser Gly Ile Ser Pro Arg Ala Val Trp Gln Phe Arg Lys Met Ile Lys
                20                  25                  30

Cys Val Ile Pro Gly Ser Asp Pro Phe Leu Glu Tyr Asn Asn Tyr Gly
            35                  40                  45

Cys Tyr Cys Gly Leu Gly Gly Ser Gly Thr Pro Val Asp Glu Leu Asp
        50                  55                  60

Lys Cys Cys Gln Thr His Asp Asn Cys Tyr Asp Gln Ala Lys Lys Leu
65                  70                  75                  80

Asp Ser Cys Lys Phe Leu Leu Asp Asn Pro Tyr Thr His Thr Tyr Ser
                85                  90                  95

Tyr Ser Cys Ser Gly Ser Ala Ile Thr Cys Ser Ser Lys Asn Lys Glu
            100                 105                 110
```

-continued

```
Cys Glu Ala Phe Ile Cys Asn Cys Asp Arg Asn Ala Ala Ile Cys Phe
        115                 120                 125

Ser Lys Ala Pro Tyr Asn Lys Ala His Lys Asn Leu Asp Thr Lys Lys
    130                 135                 140

Tyr Cys Gln Ser
145

<210> SEQ ID NO 3
<211> LENGTH: 19
<212> TYPE: DNA
<213> ORGANISM: Artificial
<220> FEATURE:
<223> OTHER INFORMATION: Inhibitory nucleic acid molecule

<400> SEQUENCE: 3
atgaaactcc ttgtgctag                                                19

<210> SEQ ID NO 4
<211> LENGTH: 14
<212> TYPE: DNA
<213> ORGANISM: Artificial
<220> FEATURE:
<223> OTHER INFORMATION: Inhibitory nucleic acid molecule

<400> SEQUENCE: 4
acagcggcat cagc                                                     14

<210> SEQ ID NO 5
<211> LENGTH: 17
<212> TYPE: DNA
<213> ORGANISM: Artificial
<220> FEATURE:
<223> OTHER INFORMATION: Inhibitory nucleic acid molecule

<400> SEQUENCE: 5
ttccgcaaaa tgatcaa                                                  17

<210> SEQ ID NO 6
<211> LENGTH: 16
<212> TYPE: DNA
<213> ORGANISM: Artificial
<220> FEATURE:
<223> OTHER INFORMATION: Inhibitory nucleic acid molecule

<400> SEQUENCE: 6
cccggggagt gacccc                                                   16

<210> SEQ ID NO 7
<211> LENGTH: 20
<212> TYPE: DNA
<213> ORGANISM: Artificial
<220> FEATURE:
<223> OTHER INFORMATION: Inhibitory nucleic acid molecule

<400> SEQUENCE: 7
tacggctgct actgtggctt                                               20

<210> SEQ ID NO 8
<211> LENGTH: 23
<212> TYPE: DNA
<213> ORGANISM: Artificial
<220> FEATURE:
<223> OTHER INFORMATION: Inhibitory nucleic acid molecule

<400> SEQUENCE: 8
```

-continued gacacatgac aactgctacg acc                         23

<210> SEQ ID NO 9
<211> LENGTH: 22
<212> TYPE: DNA
<213> ORGANISM: Artificial
<220> FEATURE:
<223> OTHER INFORMATION: Inhibitory nucleic acid molecule

<400> SEQUENCE: 9
acccacacct attcatactc gt                          22

<210> SEQ ID NO 10
<211> LENGTH: 16
<212> TYPE: DNA
<213> ORGANISM: Artificial
<220> FEATURE:
<223> OTHER INFORMATION: Inhibitory nucleic acid molecule

<400> SEQUENCE: 10
atcacctgta gcagca                                 16

<210> SEQ ID NO 11
<211> LENGTH: 19
<212> TYPE: DNA
<213> ORGANISM: Artificial
<220> FEATURE:
<223> OTHER INFORMATION: Inhibitory nucleic acid molecule

<400> SEQUENCE: 11
agctccatat aacaaggca                              19

<210> SEQ ID NO 12
<211> LENGTH: 18
<212> TYPE: DNA
<213> ORGANISM: Artificial
<220> FEATURE:
<223> OTHER INFORMATION: Inhibitory nucleic acid molecule

<400> SEQUENCE: 12
caagaagtat tgtcagag                               18

<210> SEQ ID NO 13
<211> LENGTH: 6
<212> TYPE: PRT
<213> ORGANISM: Artificial
<220> FEATURE:
<223> OTHER INFORMATION: Immunogenic peptide

<400> SEQUENCE: 13

Asn Asn Tyr Gly Cys Tyr
1               5

<210> SEQ ID NO 14
<211> LENGTH: 6
<212> TYPE: PRT
<213> ORGANISM: Artificial
<220> FEATURE:
<223> OTHER INFORMATION: Immunogenic peptide

<400> SEQUENCE: 14

Cys Tyr Cys Gly Leu Gly
1               5

<210> SEQ ID NO 15

```
<211> LENGTH: 14
<212> TYPE: PRT
<213> ORGANISM: Artificial
<220> FEATURE:
<223> OTHER INFORMATION: Immunogenic peptide

<400> SEQUENCE: 15

Tyr Asn Asn Tyr Gly Cys Tyr Cys Gly Leu Gly Gly Ser Gly
1               5                   10

<210> SEQ ID NO 16
<211> LENGTH: 20
<212> TYPE: PRT
<213> ORGANISM: Artificial
<220> FEATURE:
<223> OTHER INFORMATION: Immunogenic peptide

<400> SEQUENCE: 16

Phe Leu Glu Tyr Asn Asn Tyr Gly Cys Tyr Cys Gly Leu Gly Gly Ser
1               5                   10                  15

Gly Thr Pro Val
            20

<210> SEQ ID NO 17
<211> LENGTH: 5
<212> TYPE: PRT
<213> ORGANISM: Artificial
<220> FEATURE:
<223> OTHER INFORMATION: Immunogenic peptide

<400> SEQUENCE: 17

Gln Thr His Asp Asn
1               5

<210> SEQ ID NO 18
<211> LENGTH: 7
<212> TYPE: PRT
<213> ORGANISM: Artificial
<220> FEATURE:
<223> OTHER INFORMATION: Immunogenic peptide

<400> SEQUENCE: 18

Cys Gln Thr His Asp Asn Cys
1               5

<210> SEQ ID NO 19
<211> LENGTH: 9
<212> TYPE: PRT
<213> ORGANISM: Artificial
<220> FEATURE:
<223> OTHER INFORMATION: Immunogenic peptide

<400> SEQUENCE: 19

Glu Cys Glu Ala Phe Ile Cys Asn Cys
1               5

<210> SEQ ID NO 20
<211> LENGTH: 6
<212> TYPE: PRT
<213> ORGANISM: Artificial
<220> FEATURE:
<223> OTHER INFORMATION: Immunogenic peptide

<400> SEQUENCE: 20

Asp Arg Asn Ala Ala Ile
1               5
```

<210> SEQ ID NO 21
<211> LENGTH: 20
<212> TYPE: PRT
<213> ORGANISM: Artificial
<220> FEATURE:
<223> OTHER INFORMATION: Immunogenic peptide

<400> SEQUENCE: 21

```
Asp Arg Asn Ala Ala Ile Cys Phe Ser Lys Ala Pro Tyr Asn Lys Ala
1               5                   10                  15

His Lys Asn Leu
            20
```

<210> SEQ ID NO 22
<211> LENGTH: 1487
<212> TYPE: PRT
<213> ORGANISM: Artificial
<220> FEATURE:
<223> OTHER INFORMATION: soluble receptor

<400> SEQUENCE: 22

```
Met Val Gln Trp Leu Ala Met Leu Gln Leu Trp Leu Gln Gln Leu
1               5                   10                  15

Leu Leu Leu Gly Ile His Gln Gly Ile Ala Gln Asp Leu Thr His Ile
                20                  25                  30

Gln Glu Pro Ser Leu Glu Trp Arg Asp Lys Gly Ile Phe Ile Ile Gln
            35                  40                  45

Ser Glu Ser Leu Lys Thr Cys Ile Gln Ala Gly Lys Ser Val Leu Thr
50                  55                  60

Leu Glu Asn Cys Lys Gln Pro Asn Glu His Met Leu Trp Lys Trp Val
65                  70                  75                  80

Ser Asp Asp His Leu Phe Asn Val Gly Gly Ser Gly Cys Leu Gly Leu
                85                  90                  95

Asn Ile Ser Ala Leu Glu Gln Pro Leu Lys Leu Tyr Glu Cys Asp Ser
            100                 105                 110

Thr Leu Ile Ser Leu Arg Trp His Cys Asp Arg Lys Met Ile Glu Gly
        115                 120                 125

Pro Leu Gln Tyr Lys Val Gln Val Lys Ser Asp Asn Thr Val Val Ala
    130                 135                 140

Arg Lys Gln Ile His Arg Trp Ile Ala Tyr Thr Ser Ser Gly Gly Asp
145                 150                 155                 160

Ile Cys Glu His Pro Ser Arg Asp Leu Tyr Thr Leu Lys Gly Asn Ala
                165                 170                 175

His Gly Met Pro Cys Val Phe Pro Phe Gln Phe Lys Gly His Trp His
            180                 185                 190

His Asp Cys Ile Arg Glu Gly Gln Lys Glu His Leu Leu Trp Cys Ala
        195                 200                 205

Thr Thr Ser Arg Tyr Glu Glu Asp Glu Lys Trp Gly Phe Cys Pro Asp
    210                 215                 220

Pro Thr Ser Met Lys Val Phe Cys Asp Ala Thr Trp Gln Arg Asn Gly
225                 230                 235                 240

Ser Ser Arg Ile Cys Tyr Gln Phe Asn Leu Leu Ser Ser Leu Ser Trp
                245                 250                 255

Asn Gln Ala His Ser Ser Cys Leu Met Gln Gly Gly Ala Leu Leu Ser
            260                 265                 270

Ile Ala Asp Glu Asp Glu Glu Asp Phe Ile Arg Lys His Leu Ser Lys
        275                 280                 285
```

-continued

Val Val Lys Glu Val Trp Ile Gly Leu Asn Gln Leu Asp Glu Lys Ala
290                 295                 300

Gly Trp Gln Trp Ser Asp Gly Thr Pro Leu Ser Tyr Leu Asn Trp Ser
305                 310                 315                 320

Gln Glu Ile Thr Pro Gly Pro Phe Val Glu His His Cys Gly Thr Leu
                325                 330                 335

Glu Val Val Ser Ala Ala Trp Arg Ser Arg Asp Cys Glu Ser Thr Leu
                340                 345                 350

Pro Tyr Ile Cys Lys Arg Asp Leu Asn His Thr Ala Gln Gly Ile Leu
                355                 360                 365

Glu Lys Asp Ser Trp Lys Tyr His Ala Thr His Cys Asp Pro Asp Trp
370                 375                 380

Thr Pro Phe Asn Arg Lys Cys Tyr Lys Leu Lys Lys Asp Arg Lys Ser
385                 390                 395                 400

Trp Leu Gly Ala Leu His Ser Cys Gln Ser Asn Asp Ser Val Leu Met
                405                 410                 415

Asp Val Ala Ser Leu Ala Glu Val Glu Phe Leu Val Ser Leu Leu Arg
                420                 425                 430

Asp Glu Asn Ala Ser Glu Thr Trp Ile Gly Leu Ser Ser Asn Lys Ile
                435                 440                 445

Pro Val Ser Phe Glu Trp Ser Ser Gly Ser Ser Val Ile Phe Thr Asn
450                 455                 460

Trp Tyr Pro Leu Glu Pro Arg Ile Leu Pro Asn Arg Arg Gln Leu Cys
465                 470                 475                 480

Val Ser Ala Glu Glu Ser Asp Gly Arg Trp Lys Val Lys Asp Cys Lys
                485                 490                 495

Glu Arg Leu Phe Tyr Ile Cys Lys Lys Ala Gly Gln Val Pro Ala Asp
                500                 505                 510

Glu Gln Ser Gly Cys Pro Ala Gly Trp Glu Arg His Gly Arg Phe Cys
                515                 520                 525

Tyr Lys Ile Asp Thr Val Leu Arg Ser Phe Glu Glu Ala Ser Ser Gly
                530                 535                 540

Tyr Tyr Cys Ser Pro Ala Leu Leu Thr Ile Thr Ser Arg Phe Glu Gln
545                 550                 555                 560

Ala Phe Ile Thr Ser Leu Ile Ser Ser Val Ala Glu Lys Asp Ser Tyr
                565                 570                 575

Phe Trp Ile Ala Leu Gln Asp Gln Asn Asn Thr Gly Glu Tyr Thr Trp
                580                 585                 590

Lys Thr Val Gly Gln Arg Glu Pro Val Gln Tyr Thr Tyr Trp Asn Thr
                595                 600                 605

Arg Gln Pro Ser Asn Arg Gly Gly Cys Val Val Val Arg Gly Gly Ser
610                 615                 620

Ser Leu Gly Arg Trp Glu Val Lys Asp Cys Ser Asp Phe Lys Ala Met
625                 630                 635                 640

Ser Leu Cys Lys Thr Pro Val Lys Ile Trp Glu Lys Thr Glu Leu Glu
                645                 650                 655

Glu Arg Trp Pro Phe His Pro Cys Tyr Met Asp Trp Glu Ser Ala Thr
                660                 665                 670

Gly Leu Ala Ser Cys Phe Lys Val Phe His Ser Glu Lys Val Leu Met
                675                 680                 685

Lys Arg Ser Trp Arg Glu Ala Glu Ala Phe Cys Glu Glu Phe Gly Ala
690                 695                 700

His Leu Ala Ser Phe Ala His Ile Glu Glu Glu Asn Phe Val Asn Glu
705                710                715                720

Leu Leu His Ser Lys Phe Asn Trp Thr Gln Glu Arg Gln Phe Trp Ile
            725                730                735

Gly Phe Asn Arg Arg Asn Pro Leu Asn Ala Gly Ser Trp Ala Trp Ser
            740                745                750

Asp Gly Ser Pro Val Val Ser Ser Phe Leu Asp Asn Ala Tyr Phe Glu
            755                760                765

Glu Asp Ala Lys Asn Cys Ala Val Tyr Lys Ala Asn Lys Thr Leu Leu
770                775                780

Pro Ser Asn Cys Ala Ser Lys His Glu Trp Ile Cys Arg Ile Pro Arg
785                790                795                800

Asp Val Arg Pro Lys Phe Pro Asp Trp Tyr Gln Tyr Asp Ala Pro Trp
            805                810                815

Leu Phe Tyr Gln Asn Ala Glu Tyr Leu Phe His Thr His Pro Ala Glu
            820                825                830

Trp Ala Thr Phe Glu Phe Val Cys Gly Trp Leu Arg Ser Asp Phe Leu
            835                840                845

Thr Ile Tyr Ser Ala Gln Glu Gln Glu Phe Ile His Ser Lys Ile Lys
850                855                860

Gly Leu Thr Lys Tyr Gly Val Lys Trp Trp Ile Gly Leu Glu Glu Gly
865                870                875                880

Gly Ala Arg Asp Gln Ile Gln Trp Ser Asn Gly Ser Pro Val Ile Phe
            885                890                895

Gln Asn Trp Asp Lys Gly Arg Glu Glu Arg Val Asp Ser Gln Arg Lys
            900                905                910

Arg Cys Val Phe Ile Ser Ser Ile Thr Gly Leu Trp Gly Thr Glu Asn
            915                920                925

Cys Ser Val Pro Leu Pro Ser Ile Cys Lys Arg Val Lys Ile Trp Val
930                935                940

Ile Glu Lys Glu Lys Pro Pro Thr Gln Pro Gly Thr Cys Pro Lys Gly
945                950                955                960

Trp Leu Tyr Phe Asn Tyr Lys Cys Phe Leu Val Thr Ile Pro Lys Asp
            965                970                975

Pro Arg Glu Leu Lys Thr Trp Thr Gly Ala Gln Glu Phe Cys Val Ala
            980                985                990

Lys Gly Gly Thr Leu Val Ser Ile Lys Ser Glu Leu Glu Gln Ala Phe
            995                1000                1005

Ile Thr Met Asn Leu Phe Gly Gln Thr Thr Asn Val Trp Ile Gly
    1010                1015                1020

Leu Gln Ser Thr Asn His Glu Lys Trp Val Asn Gly Lys Pro Leu
    1025                1030                1035

Val Tyr Ser Asn Trp Ser Pro Ser Asp Ile Ile Asn Ile Pro Ser
    1040                1045                1050

Tyr Asn Thr Thr Glu Phe Gln Lys His Ile Pro Leu Cys Ala Leu
    1055                1060                1065

Met Ser Ser Asn Pro Asn Phe His Phe Thr Gly Lys Trp Tyr Phe
    1070                1075                1080

Asp Asp Cys Gly Lys Glu Gly Tyr Gly Phe Val Cys Glu Lys Met
    1085                1090                1095

Gln Asp Thr Leu Glu His His Val Asn Val Ser Asp Thr Ser Ala
    1100                1105                1110

Ile Pro Ser Thr Leu Glu Tyr Gly Asn Arg Thr Tyr Lys Ile Ile

```
                1115                1120                1125
Arg Gly Asn Met Thr Trp Tyr Ala Ala Gly Lys Ser Cys Arg Met
            1130                1135                1140

His Arg Ala Glu Leu Ala Ser Ile Pro Asp Ala Phe His Gln Ala
            1145                1150                1155

Phe Leu Thr Val Leu Leu Ser Arg Leu Gly His Thr His Trp Ile
            1160                1165                1170

Gly Leu Ser Thr Thr Asp Asn Gly Gln Thr Phe Asp Trp Ser Asp
            1175                1180                1185

Gly Thr Lys Ser Pro Phe Thr Tyr Trp Lys Asp Glu Glu Ser Ala
            1190                1195                1200

Phe Leu Gly Asp Cys Ala Phe Ala Asp Thr Asn Gly Arg Trp His
            1205                1210                1215

Ser Thr Ala Cys Glu Ser Phe Leu Gln Gly Ala Ile Cys His Val
            1220                1225                1230

Val Thr Glu Thr Lys Ala Phe Glu His Pro Gly Leu Cys Ser Glu
            1235                1240                1245

Thr Ser Val Pro Trp Ile Lys Phe Lys Gly Asn Cys Tyr Ser Phe
            1250                1255                1260

Ser Thr Val Leu Asp Ser Arg Ser Phe Glu Asp Ala His Glu Phe
            1265                1270                1275

Cys Lys Ser Glu Gly Ser Asn Leu Leu Ala Ile Arg Asp Ala Ala
            1280                1285                1290

Glu Asn Ser Phe Leu Leu Glu Glu Leu Leu Ala Phe Gly Ser Ser
            1295                1300                1305

Val Gln Met Val Trp Leu Asn Ala Gln Phe Asp Asn Asn Lys
            1310                1315                1320

Thr Leu Arg Trp Phe Asp Gly Thr Pro Thr Glu Gln Ser Asn Trp
            1325                1330                1335

Gly Leu Arg Lys Pro Asp Met Asp His Leu Lys Pro His Pro Cys
            1340                1345                1350

Val Val Leu Arg Ile Pro Glu Gly Ile Trp His Phe Thr Pro Cys
            1355                1360                1365

Glu Asp Lys Lys Gly Phe Ile Cys Lys Met Glu Ala Gly Ile Pro
            1370                1375                1380

Ala Val Thr Ala Gln Pro Glu Lys Gly Leu Ser His Ser Ile Val
            1385                1390                1395

Pro Val Thr Val Thr Leu Thr Leu Ile Ile Ala Leu Gly Ile Phe
            1400                1405                1410

Met Leu Cys Phe Trp Ile Tyr Lys Gln Lys Ser Asp Ile Phe Gln
            1415                1420                1425

Arg Leu Thr Gly Ser Arg Gly Ser Tyr Tyr Pro Thr Leu Asn Phe
            1430                1435                1440

Ser Thr Ala His Leu Glu Glu Asn Ile Leu Ile Ser Asp Leu Glu
            1445                1450                1455

Lys Asn Thr Asn Asp Glu Glu Val Arg Asp Ala Pro Ala Thr Glu
            1460                1465                1470

Ser Lys Arg Gly His Lys Gly Arg Pro Ile Cys Ile Ser Pro
            1475                1480                1485

<210> SEQ ID NO 23
<211> LENGTH: 1326
<212> TYPE: PRT
<213> ORGANISM: Artificial
```

<220> FEATURE:
<223> OTHER INFORMATION: soluble receptor

<400> SEQUENCE: 23

Met Leu Leu Ser Pro Ser Leu Leu Leu Leu Leu Gly Gly Ala
1               5                   10                  15

Ala Gly Cys Ala Glu Gly Val Ala Ala Leu Thr Pro Glu Arg Leu
        20                  25                  30

Leu Glu Trp Gln Asp Lys Gly Ile Phe Val Ile Gln Ser Glu Ser Leu
            35                  40                  45

Lys Lys Cys Ile Gln Ala Gly Lys Ser Val Leu Thr Leu Gly Arg Thr
50                  55                  60

Gly Ser Lys Gln Ala Asn Lys His Met Leu Trp Lys Trp Val Ser Asn
65                  70                  75                  80

His Gly Leu Phe Asn Ile Gly Gly Ser Gly Cys Leu Gly Leu Asn Phe
                85                  90                  95

Ser Ala Pro Glu Gln Pro Leu Ser Leu Tyr Glu Cys Asp Ser Thr Leu
            100                 105                 110

Val Ser Leu Arg Trp Arg Cys Asn Arg Lys Met Ile Thr Gly Pro Leu
        115                 120                 125

Gln Tyr Ser Val Gln Val Ala His Asp Asn Thr Val Val Ala Ser Arg
    130                 135                 140

Lys Tyr Ile His Lys Trp Ile Ser Tyr Gly Ser Gly Gly Gly Asp Ile
145                 150                 155                 160

Cys Glu Tyr Leu His Lys Asp Leu His Thr Ile Lys Gly Asn Thr His
                165                 170                 175

Gly Met Pro Cys Met Phe Pro Phe Gln Tyr Asn His Gln Trp His His
            180                 185                 190

Glu Cys Thr Arg Glu Gly Arg Glu Asp Asp Leu Leu Trp Cys Ala Thr
        195                 200                 205

Thr Ser Arg Tyr Glu Arg Asp Glu Lys Trp Gly Phe Cys Pro Asp Pro
    210                 215                 220

Thr Ser Ala Glu Val Gly Cys Asp Thr Ile Trp Glu Lys Asp Leu Asn
225                 230                 235                 240

Ser His Ile Cys Tyr Gln Phe Asn Leu Leu Ser Ser Leu Ser Trp Ser
                245                 250                 255

Glu Ala His Ser Ser Cys Gln Met Gln Gly Gly Thr Leu Leu Ser Ile
            260                 265                 270

Thr Asp Glu Thr Glu Glu Asn Phe Ile Arg Glu His Met Ser Ser Lys
        275                 280                 285

Thr Val Glu Val Trp Val Gly Leu Asn Gln Leu Asp Glu Asp Ala Gly
    290                 295                 300

Trp Gln Trp Ser Asp Gly Thr Pro Leu Asn Tyr Leu Asn Trp Ser Pro
305                 310                 315                 320

Glu Val Asn Phe Glu Pro Phe Val Glu Asp His Cys Gly Thr Phe Ser
                325                 330                 335

Ser Phe Met Pro Ser Ala Trp Arg Ser Arg Asp Cys Glu Ser Thr Leu
            340                 345                 350

Pro Tyr Ile Cys Lys Lys Tyr Leu Asn His Ile Asp His Glu Ile Val
        355                 360                 365

Glu Lys Asp Ala Trp Lys Tyr Tyr Ala Thr His Cys Glu Pro Gly Trp
    370                 375                 380

Asn Pro Tyr Asn Arg Asn Cys Tyr Lys Leu Gln Lys Glu Glu Lys Thr
385                 390                 395                 400

-continued

Trp His Glu Ala Leu Arg Ser Cys Gln Ala Asp Asn Ser Ala Leu Ile
            405                 410                 415

Asp Ile Thr Ser Leu Ala Glu Val Glu Phe Leu Val Thr Leu Leu Gly
            420                 425                 430

Asp Glu Asn Ala Ser Glu Thr Trp Ile Gly Leu Ser Ser Asn Lys Ile
            435                 440                 445

Pro Val Ser Phe Glu Trp Ser Asn Asp Ser Ser Val Ile Phe Thr Asn
            450                 455                 460

Trp His Thr Leu Glu Pro His Ile Phe Pro Asn Arg Ser Gln Leu Cys
465                 470                 475                 480

Val Ser Ala Glu Gln Ser Glu Gly His Trp Lys Val Lys Asn Cys Glu
            485                 490                 495

Glu Arg Leu Phe Tyr Ile Cys Lys Lys Ala Gly His Val Leu Ser Asp
            500                 505                 510

Ala Glu Ser Gly Cys Gln Glu Gly Trp Glu Glu Thr Cys Gly Phe Cys
            515                 520                 525

Tyr Lys Ile Asp Thr Val Leu Arg Ser Phe Asp Gln Ala Ser Ser Gly
            530                 535                 540

Tyr Tyr Cys Pro Pro Ala Leu Val Thr Ile Thr Asn Arg Phe Glu Gln
545                 550                 555                 560

Ala Phe Ile Thr Ser Leu Ile Ser Ser Val Val Lys Met Lys Asp Ser
            565                 570                 575

Tyr Phe Trp Ile Ala Leu Gln Asp Gln Asn Asp Thr Gly Glu Tyr Thr
            580                 585                 590

Trp Lys Pro Val Gly Gln Lys Pro Glu Pro Val Gln Tyr Thr His Trp
            595                 600                 605

Asn Thr His Gln Pro Arg Tyr Ser Gly Gly Cys Val Ala Met Arg Gly
            610                 615                 620

Arg His Pro Leu Gly Arg Trp Glu Val Lys His Cys Arg His Phe Lys
625                 630                 635                 640

Ala Met Ser Leu Cys Lys Gln Pro Val Glu Asn Gln Glu Lys Ala Glu
            645                 650                 655

Tyr Glu Glu Arg Trp Pro Phe His Pro Cys Tyr Leu Asp Trp Glu Ser
            660                 665                 670

Glu Pro Gly Leu Ala Ser Cys Phe Lys Val Phe His Ser Glu Lys Val
            675                 680                 685

Leu Met Lys Arg Thr Trp Arg Glu Ala Glu Ala Phe Cys Glu Glu Phe
            690                 695                 700

Gly Ala His Leu Ala Ser Phe Ala His Ile Glu Glu Asn Phe Val
705                 710                 715                 720

Asn Glu Leu Leu His Pro Lys Phe Asn Trp Thr Glu Glu Arg Gln Phe
            725                 730                 735

Trp Ile Gly Phe Asn Lys Arg Asn Pro Leu Asn Ala Gly Ser Trp Glu
            740                 745                 750

Trp Ser Asp Arg Thr Pro Val Val Ser Ser Phe Leu Asp Asn Thr Tyr
            755                 760                 765

Phe Gly Glu Asp Ala Arg Asn Cys Ala Val Tyr Lys Pro Asn Lys Thr
            770                 775                 780

Leu Leu Pro Leu His Cys Gly Ser Lys Arg Glu Trp Ile Cys Lys Ile
785                 790                 795                 800

Pro Arg Asp Val Lys Pro Lys Ile Pro Phe Trp Tyr Gln Tyr Asp Val
            805                 810                 815

```
Pro Trp Leu Phe Tyr Gln Asp Ala Glu Tyr Leu Phe His Thr Phe Ala
            820                 825                 830

Ser Glu Trp Leu Asn Phe Glu Phe Val Cys Ser Trp Leu His Ser Asp
            835                 840                 845

Leu Leu Thr Ile His Ser Ala His Glu Gln Glu Phe Ile His Ser Lys
            850                 855                 860

Ile Lys Ala Leu Ser Lys Tyr Gly Ala Ser Trp Trp Ile Gly Leu Gln
865                 870                 875                 880

Glu Glu Arg Ala Asn Asp Glu Phe Arg Trp Arg Asp Gly Thr Pro Val
                885                 890                 895

Ile Tyr Gln Asn Trp Asp Thr Gly Arg Glu Arg Thr Val Asn Asn Gln
            900                 905                 910

Ser Gln Arg Cys Gly Phe Ile Ser Ser Ile Thr Gly Leu Trp Gly Ser
            915                 920                 925

Glu Glu Cys Ser Val Ser Met Pro Ser Ile Cys Lys Arg Lys Lys Val
            930                 935                 940

Trp Leu Ile Glu Lys Lys Asp Thr Pro Lys Gln His Gly Thr Cys
945                 950                 955                 960

Pro Lys Gly Trp Leu Tyr Phe Asn Tyr Lys Cys Leu Leu Asn Ile
            965                 970                 975

Pro Lys Asp Pro Ser Ser Trp Lys Asn Trp Thr His Ala Gln His Phe
            980                 985                 990

Cys Ala Glu Glu Gly Gly Thr Leu  Val Ala Ile Glu Ser  Glu Val Glu
            995                  1000                 1005

Gln Ala  Phe Ile Thr Met Asn  Leu Phe Gly Gln Thr  Thr Ser Val
        1010                 1015                 1020

Trp Ile  Gly Leu Gln Asn Asp  Asp Tyr Glu Thr Trp  Leu Asn Gly
        1025                 1030                 1035

Lys Pro  Val Val Tyr Ser Asn  Trp Ser Pro Phe Asp  Ile Ile Asn
        1040                 1045                 1050

Ile Pro  Ser His Asn Thr Thr  Glu Val Gln Lys His  Ile Pro Leu
        1055                 1060                 1065

Cys Ala  Leu Leu Ser Ser Asn  Pro Asn Phe His Phe  Thr Gly Lys
        1070                 1075                 1080

Trp Tyr  Phe Glu Asp Cys Gly  Lys Glu Gly Tyr Gly  Phe Val Cys
        1085                 1090                 1095

Glu Lys  Met Gln Asp Thr Ser  Gly His Gly Val Asn  Thr Ser Asp
        1100                 1105                 1110

Met Tyr  Pro Met Pro Asn Thr  Leu Glu Tyr Gly Asn  Arg Thr Tyr
        1115                 1120                 1125

Lys Ile  Ile Asn Ala Asn Met  Thr Trp Tyr Ala Ala  Ile Lys Thr
        1130                 1135                 1140

Cys Leu  Met His Lys Ala Gln  Leu Val Ser Ile Thr  Asp Gln Tyr
        1145                 1150                 1155

His Gln  Ser Phe Leu Thr Val  Val Leu Asn Arg Leu  Gly Tyr Ala
        1160                 1165                 1170

His Trp  Ile Gly Leu Phe Thr  Thr Asp Asn Gly Leu  Asn Phe Asp
        1175                 1180                 1185

Trp Ser  Asp Gly Thr Lys Ser  Ser Phe Thr Phe Trp  Lys Asp Glu
        1190                 1195                 1200

Glu Ser  Ser Leu Leu Gly Asp  Cys Val Phe Ala Asp  Ser Asn Gly
        1205                 1210                 1215

Arg Trp  His Ser Thr Ala Cys  Asp Ser Phe Leu Gln  Gly Ala Ile
```

```
                1220                1225                1230

Cys His Val Pro Pro Glu Thr Arg Gln Ser Glu His Pro Glu Leu
    1235                1240                1245

Cys Ser Glu Thr Ser Ile Pro Trp Ile Lys Phe Lys Ser Asn Cys
    1250                1255                1260

Tyr Lys Phe Ser Thr Val Leu Asp Ser Met Ser Phe Glu Ala Ala
    1265                1270                1275

His Glu Phe Cys Lys Lys Glu Gly Ser Asn Leu Leu Thr Ile Lys
    1280                1285                1290

Asp Glu Ala Glu Asn Ala Phe Leu Leu Glu Glu Leu Phe Ala Phe
    1295                1300                1305

Gly Ser Ser Val Gln Met Val Trp Leu Asn Ala Gln Phe Asp Gly
    1310                1315                1320

Asn Ser Lys
    1325

<210> SEQ ID NO 24
<211> LENGTH: 48
<212> TYPE: PRT
<213> ORGANISM: Artificial
<220> FEATURE:
<223> OTHER INFORMATION: inhibitor peptide

<400> SEQUENCE: 24

Leu Ser Leu Tyr Glu Cys Asp Ser Thr Leu Val Ser Leu Arg Trp Arg
1               5                   10                  15

Cys Asn Arg Lys Met Ile Thr Gly Pro Leu Gln Tyr Ser Val Gln Val
            20                  25                  30

Ala His Asp Asn Thr Val Val Ala Ser Arg Lys Tyr Ile His Lys Trp
        35                  40                  45

<210> SEQ ID NO 25
<211> LENGTH: 17
<212> TYPE: PRT
<213> ORGANISM: Artificial
<220> FEATURE:
<223> OTHER INFORMATION: inhibitor peptide

<400> SEQUENCE: 25

Trp Glu Lys Asp Leu Asn Ser His Ile Cys Tyr Gln Phe Asn Leu Leu
1               5                   10                  15

Ser

<210> SEQ ID NO 26
<211> LENGTH: 24
<212> TYPE: PRT
<213> ORGANISM: Artificial
<220> FEATURE:
<223> OTHER INFORMATION: inhibitor peptide

<400> SEQUENCE: 26

Asp Cys Glu Ser Thr Leu Pro Tyr Ile Cys Lys Lys Tyr Leu Asn His
1               5                   10                  15

Ile Asp His Glu Ile Val Glu Lys
            20

<210> SEQ ID NO 27
<211> LENGTH: 33
<212> TYPE: PRT
<213> ORGANISM: Artificial
<220> FEATURE:
```

<223> OTHER INFORMATION: inhibitor peptide

<400> SEQUENCE: 27

Gln Tyr Lys Val Gln Val Lys Ser Asp Asn Thr Val Val Ala Arg Lys
1               5                   10                  15
Gln Ile His Arg Trp Ile Ala Tyr Thr Ser Ser Gly Gly Asp Ile Cys
            20                  25                  30
Glu

<210> SEQ ID NO 28
<211> LENGTH: 28
<212> TYPE: PRT
<213> ORGANISM: Artificial
<220> FEATURE:
<223> OTHER INFORMATION: inhibitor peptide

<400> SEQUENCE: 28

Leu Ser Tyr Leu Asn Trp Ser Gln Glu Ile Thr Pro Gly Pro Phe Val
1               5                   10                  15
Glu His His Cys Gly Thr Leu Glu Val Val Ser Ala
            20                  25

<210> SEQ ID NO 29
<211> LENGTH: 23
<212> TYPE: PRT
<213> ORGANISM: Artificial
<220> FEATURE:
<223> OTHER INFORMATION: inhibitor peptide

<400> SEQUENCE: 29

Ser Arg Phe Glu Gln Ala Phe Ile Thr Ser Leu Ile Ser Ser Val Ala
1               5                   10                  15
Glu Lys Asp Ser Tyr Phe Trp
            20

<210> SEQ ID NO 30
<211> LENGTH: 29
<212> TYPE: PRT
<213> ORGANISM: Artificial
<220> FEATURE:
<223> OTHER INFORMATION: inhibitor peptide

<400> SEQUENCE: 30

Trp Ile Cys Arg Ile Pro Arg Asp Val Arg Pro Lys Phe Pro Asp Trp
1               5                   10                  15
Tyr Gln Tyr Asp Ala Pro Trp Leu Phe Tyr Gln Asn Ala
            20                  25

<210> SEQ ID NO 31
<211> LENGTH: 30
<212> TYPE: PRT
<213> ORGANISM: Artificial
<220> FEATURE:
<223> OTHER INFORMATION: inhibitor peptide

<400> SEQUENCE: 31

Ala Phe His Gln Ala Phe Leu Thr Val Leu Leu Ser Arg Leu Gly His
1               5                   10                  15
Thr His Trp Ile Gly Leu Ser Thr Thr Asp Asn Gly Gln Thr
            20                  25                  30

THERAPEUTIC METHODS AND COMPOSITIONS

CROSS-REFERENCE TO RELATED APPLICATIONS

This application is the U.S. national stage application of International Patent Application No. PCT/EP2014/078969, filed Dec. 22, 2014, which claims the benefit of U.S. Provisional Patent Application No. 61/920,137, filed Dec. 23, 2013 and U.S. Provisional Patent Application No. 62/017,457, filed Jun. 26, 2014.

The Sequence Listing for this application is labeled "Seq-List.txt" which was created on Jun. 14, 2016 and is 33 KB. The entire content of the sequence listing is incorporated herein by reference in its entirety.

FIELD OF THE INVENTION

The present invention relates to compositions and methods for modulating the immune system in a subject in need thereof. The invention more particularly discloses the existence and characterization of a key endogenous factor of the immune response and provides novel therapeutic and diagnostic methods and compositions based on a modulation of this factor. The invention particularly provides compositions and methods suitable to stimulate or inhibit CD4 T cell-mediated immune responses in a subject, as well as methods and compositions for monitoring immunodeficiency, including immunodeficiency associated with human immunodeficiency virus (HIV) infection. Also provided are methods and compositions to diagnose and assay CD4 T-cell-defects that persist after antiretroviral therapy, as well as methods to develop drugs able to specifically treat this immunodeficiency.

INTRODUCTION

CD4 T lymphocytes play a pre-eminent role in controlling the immune system (both cellular and humoral responses) and are critical in various disease conditions.

During the immunological disease associated with HIV pathogenesis, less than 0.5% of all CD4 T cells are actually infected (as measured in the peripheral blood), but the great majority of CD4 T cells shows major regulatory dysfunction. Uninfected CD4 T lymphocytes progressively lose their function, become anergic, and their numbers decrease resulting in CD4 lymphopenia. Anergy and lymphopenia are the hallmarks of the immunodeficiency characterizing HIV-infected patients. The mechanisms behind these phenomena have never been fully elucidated (1).

Immune activation and inflammation also play a critical role in HIV pathogenesis (2, 3). The inventors have previously demonstrated that a decrease in responsiveness to interleukin-2 (IL-2), leading to CD4 anergy (4), and a reduction in responsiveness to interleukin-7 (IL-7) which, by disrupting the IL-7/CD4 regulatory loop, participates in the mechanisms leading to CD4 lymphopenia (5). The mechanisms involved have been attributed to defects in the Janus kinase (Jak)/Signal Tranducer and Activator of Transcription (STAT) pathway (6, 7). Similar results have been obtained by other laboratories (8, 9). In this regard, compartmentalization of the IL-7 receptor (IL-7R) is required to initiate normal CD4 T cell responses (10). Upon IL-7 binding, the two chains of the IL-7R (IL-7R alpha and gamma-c) are first driven into membrane microdomains (MMD). These are cellular compartments which, like lipid rafts, are rich in cholesterol and sphingomyelin, but they also contain very significant amounts of structural and functional proteins (11). IL-7R complexes induce a reorganization of the cytoskeleton which then interacts with its meshwork. These two successive steps would be required for initiation of the Jak/STAT pathway (12).

The present inventors have investigated the mechanisms behind the unresponsiveness of CD4 T lymphocytes in viremic HIV-infected patients (VP). The experiments provided herein demonstrate that chronic activation of CD4 T lymphocytes drives them into an aberrant state of activation/differentiation which renders them refractory to certain physiological signals such as those delivered by interleukin-7. Furthermore, the present invention reports the identification, isolation and characterization, from human plasma, of the protein responsible for this aberrant state of CD4 T cell activation. For the first time, the invention thus discloses that immunosuppression can be mediated by an endogenous circulating protein which, upon expression, is able to induce alteration and inactivation of CD4-T cells and, upon inhibition, can stimulate the immune system in a subject.

Based in part on these remarkable findings, the invention now provides new methods, compositions and compounds for modulating the immune system, particularly for modulating the immune system in subjects having altered immunity (e.g.; immuno-depressed or pathologic immune reactions). The invention further provides novel methods for treating immune disorders by modulating CD4 T cells. The invention is particularly suited for treating immunodeficiencies linked to CD4 T cell impairment, such as immunodeficiency syndrome associated with HIV-infection. The invention also provides reagents and methods for characterizing the aberrant activation state, reactiveness to IL7 and/or for monitoring immunoresponse impaired in HIV infected patients. Response of CD4 T cells can be evaluated in untreated or treated patients with antiretroviral drugs, and qualify their response to treatment and evaluate the competency of their CD4 T cells.

SUMMARY OF THE INVENTION

An object of the invention relates to a method for modulating an immune response in a subject, comprising exposing the subject to a compound that modulates the amount (e.g., expression) or activity of GIBsPLA2.

A further object of the invention relates to a method of treatment of an immune disorder in a subject, comprising exposing the subject to a compound that modulates the amount (e.g., expression) or activity of GIBsPLA2.

A further object of the invention relates to a method of treatment of an immune disorder in a subject, comprising modulating the amount (e.g., expression) or activity of GIBsPLA2 in the subject.

Another object of the invention relates to the use of a compound that modulates the amount (e.g., expression) or activity of GIBsPLA2 for the manufacture of a medicament for modulating an immune response or for treating an immune disorder in a subject.

Another object of the invention relates to a GIBsPLA2 modulator for use in a method of modulating an immune response or of treating an immune disorder in a subject.

Another object of the invention relates to a GIBsPLA2 modulator for use to modulate white blood cells in a subject.

In a first embodiment, the invention is used to induce or stimulate an immune response in the subject, and comprises inhibiting GIBsPLA2 in said subject, or exposing the subject to a GIBsPLA2 inhibitor. Such embodiment is particularly suited to treat immuno-deficient subjects or subject in need of stimulated immunity (e.g., infectious diseases, cancer, etc.).

A particular object of the invention thus resides in a method of stimulating an immune response in a subject, comprising inhibiting GIBsPLA2 in said subject or exposing the subject to a GIBsPLA2 inhibitor.

A further object of the invention relates to a method of treating an infectious disease in a subject, comprising inhibiting GIBsPLA2 in said subject or exposing the subject to a GIBsPLA2 inhibitor.

A more particular embodiment of the invention relates to a method of treating AIDS in a HIV-infected subject, comprising inhibiting GIBsPLA2 in said subject or exposing the subject to a GIBsPLA2 inhibitor.

In a particular embodiment, exposing the subject to an inhibitor comprises administering the inhibitor to the subject. In another embodiment, exposing the subject to an inhibitor comprises vaccinating the subject against GIBsPLA2.

In this regard, in a particular embodiment, the invention relates to a method for stimulating the immune system of a subject in need thereof, the method comprising vaccinating the subject against GIBsPLA2.

In another particular embodiment, the invention relates to a GIBsPLA2 antigen for use to vaccinate a subject in need thereof.

In another aspect, the invention is used to reduce or suppress an unwanted or deleterious immune response in the subject, and comprises causing or increasing GIBsPLA2 in said subject, or exposing the subject to a GIBsPLA2 agonist or activator. Such embodiment is particularly suited to treat subjects having abnormal and/or pathologic immune responses (e.g., auto-immune diseases, inflammation, urticaria, eczema, allergies, asthma, etc.).

In a further aspect, the invention provides methods for diagnosing human immunodeficiency associated with CD4 T cell alteration. In some embodiments the methods comprise (a) providing a sample containing a body fluid, preferably plasma from a subject, and (b) detecting the presence of GIBsPLA2 in the sample. In some embodiments of the methods the immunodeficiency is immunodeficiency associated with human immunodeficiency virus (HIV) infection. In some embodiments the method comprises contacting the sample with an antibody specific for GIBsPLA2. In some embodiments of the methods the presence of GIBsPLA2 in the sample is detected by an enzyme-linked immunosorbent assay (ELISA).

In another aspect, the invention provides methods for identifying candidate immunodeficiency therapeutic agents. In some embodiments the immunodeficiency is associated with CD4 T cell alteration. In some embodiments of the methods, the human immunodeficiency associated with CD4 T cell alteration is caused by viral infection, particularly human immunodeficiency virus (HIV) infection. In some embodiments the methods comprise: (a) contacting CD4 T lymphocytes with GIBsPLA2 in the presence of an agent, (b) measuring GIBsPLA2-induced CD4 T cell activation, and (c) comparing the level of GIBsPLA2-induced CD4 T cell activation in the presence of the agent with the level of GIBsPLA2-induced CD4 T cell activation in the absence of the agent. In some embodiments of the methods, if the level of GIBsPLA2-induced CD4 T cell activation in the presence of the agent is lower than the level of GIBsPLA2-induced CD4 T cell activation in the absence of the agent, then the agent is identified as a candidate immunodeficiency therapeutic agent. In some embodiments of the methods, if the level of GIBsPLA2-induced CD4 T cell activation in the presence of the agent is not lower than the level of GIBsPLA2-induced CD4 T cell activation in the absence of the agent, then the agent is identified as a candidate immunosuppressing therapeutic agent. In some embodiments the methods comprise measuring GIBsPLA2-induced CD4 T cell activation by determining the number of MMD per CD4 T cell. In some embodiments the methods comprise measuring GIBsPLA2-induced CD4 T cell activation by determining the mean diameter of MMD on CD4 T cells. In some embodiments the methods comprise measuring GIBsPLA2-induced CD4 T cell activation by determining the IL-7 responsiveness of CD4 T cells.

In another aspect, the invention relates to a pharmaceutical composition comprising a GIBsPLA2 modulator and a pharmaceutically acceptable carrier or excipient. In a preferred embodiment, the GIBsPLA2 modulator is a GIBsPLA2 inhibitor, more preferably selected from an antibody or a fragment or derivative thereof, an inhibitory nucleic acid, a peptide or a small drug. In another particular embodiment, the GIBsPLA2 modulator is a GIBsPLA2 agonist or activator, more particularly a GIBsPLA2 protein.

In another aspect, the invention relates to a vaccine composition comprising a GIBsPLA2 antigen (e.g., an immunogenic GIBsPLA2 protein or an epitope-containing fragment thereof), a pharmaceutically acceptable carrier or excipient and, optionally, an adjuvant. In a preferred embodiment, the GIBsPLA2 antigen is a GIBsPLA2 protein or a fragment thereof treated to (i) increase its immunogenicity in human subjects and/or to (ii) reduce its biological activity.

The invention may be used in any mammal. It is particularly suited for use in human subjects. It may be used to increase the immune response in any mammal, and it is particularly adapted to induce potent CD4-T cell activity in immuno-depressed subjects.

BRIEF DESCRIPTION OF THE DRAWINGS

FIGS. 1*a* to 1*e* shows that, before any stimulation, CD4 T cells from VP show an aberrant state of activation with many large membrane microdomains that are unaffected by IL-7.

(a) Membrane microdomains (MMD) were labelled with cholera toxin subunit B (CtxB-AF488) and analyzed by STED microscopy. From top to bottom, purified CD4 T cells from HD, VP and PHA-activated (40 μg/ml, 30 min) HD T cells. For each group the top half of a representative CD4 T-cell before and after IL-7 stimulation (2 nM, 15 min) is shown from Z-stack image series. CD4 T lymphocytes were also treated with cholesterol oxidase (COase, 31 μM, 25 min) plus sphyngomyelinase (SMase, 2.7 μM, 5 min) before stimulation by IL-7.

(b, c) MMD were counted on the entire surface of the purified CD4 T cells. An average of 50 cells were examined. (b) HD cells before (HDc: NS) and after IL-7 stimulation (HDc: IL-7). (c) VP cells before (VPc: NS) and after IL-7 stimulation VP (VPc: IL-7), PHA-activated HD cells before (HDc: PHA) and after IL-7 stimulation (HDc: PHA/IL-7).

(d, e) MMD size was measured at the surface of purified CD4 T cells (d) IL-7-stimulated HD cells (HDc: IL-7), (e) IL-7-stimulated VP cells (VPc: IL-7) and IL-7-stimulated PHA-pre-activated HD cells (HDc: IL-7).

FIGS. 2*a* to 2*c* show that IL-7R chains from VP CD4 T-cells are embedded in detergent-resistant microdomains (DRM) that are unaffected by IL-7. Purified CD4 T lymphocytes were lysed (0.5% Triton X-100) and 200 μl of the lysate was loaded on a 5-40% sucrose gradient. After 16 h of centrifugation (50 krpm) at 4° C., 18 fractions were collected (#1 left=tube top=5% sucrose; #18 right=tube bottom=40% sucrose). Each fraction was analyzed on SDS-PAGE (7% acrylamide-bis). Flottilin, IL-7R alpha and gamma-c were detected by immunoblotting (10).

(a) Flottilin was used as a marker to indicate low density fractions corresponding to DRM and high-density fractions outside rafts.

(b) IL-7Ralpha and (c) gamma-c bands are shown for purified non-stimulated HD CD4 T-cells (HDc: NS), IL-7-stimulated HD cells (HDc:IL-7), non stimulated VP cells (VPc:NS) and PHA-activated HD cells (HDc:PHA).

FIGS. 3a to 3e show that IL-7R function is altered in membrane microdomains of VP CD4 T-cells.

Figure 7:
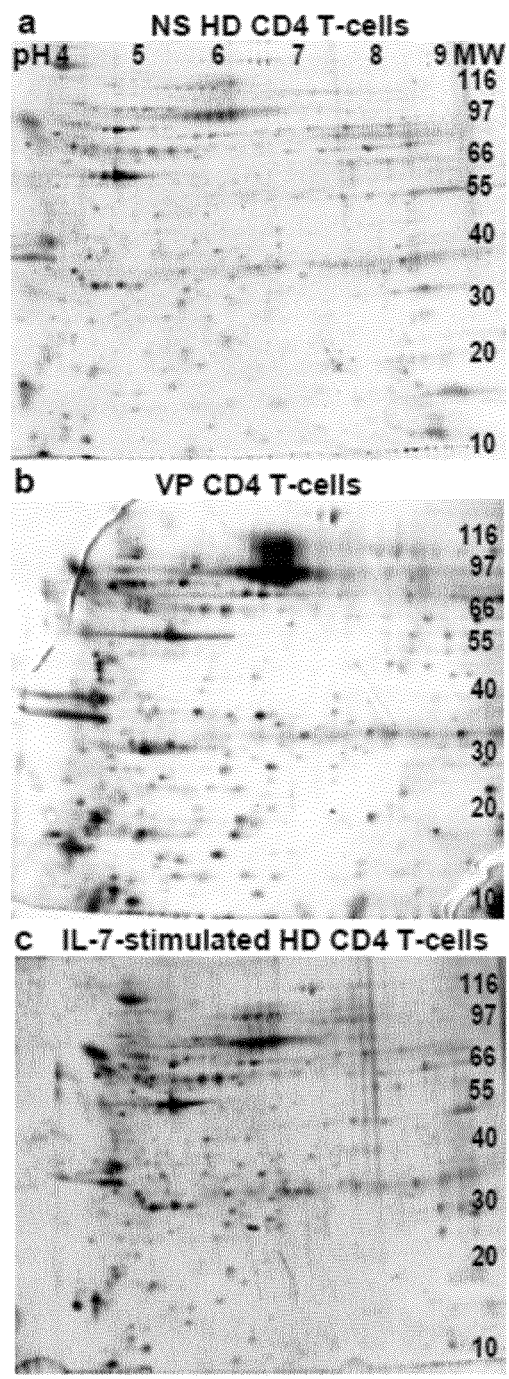

(a) Two-dimensional effective diffusion rates $D_{eff}$ for IL-7Ralpha were measured as developed in FIG. 7. Diffusion rates were also measured after adding various drugs: COase (31 µM, 30 min) plus SMase (2.7 µM, 5 min) (CO/SM), Col (10 µM, 30 min) plus CytD (20 µM, 30 min) (CytD/Col), or in the presence of all these inhibitors (all). CD4 T cells from HD (HDc) and VP (VPc) were studied, as were PHA-activated HD CD4 T cells (HDc: PHA). Bars indicate SEM from 5 independent experiments. More experimental data are given in FIG. 8.

(b) IL-7-induced phosphorylation and nuclear translocation of STAT5 were followed using rabbit phospho-STAT5 labelled with goat anti-rabbit-Atto642 and analyzed by pulsed-STED microscopy (0.5 µm slices). The experiments involved purified non stimulated HD CD4 T cells (HDc: NS), IL-7-stimulated HD CD4 T cells (HDc: IL-7), non stimulated VP CD4 T cells (VPc: NS), IL-7-stimulated VP CD4 T cells (VPc:IL-7), PHA-activated HD CD4 T cells (HDc:PHA) and PHA-activated HD CD4 T cells stimulated by IL-7 (HDc:PHA/IL-7). The effects of colchicine plus cytochalasin D are shown in the left panel.

(c, d, e) After IL-7 stimulation, the kinetics of phospho-STAT5 appearance in the cytoplasm and accumulation in the nucleus were measured using ImageJ software. (c) HD CD4 T cells (black line) and HD CD4 T cells treated with Col plus CytD (blue line), (d) VP CD4 T cells (red line) and (e) PHA-activated HD CD4 T cells (green line).

FIGS. 4a to 4d show that plasma from VP induces an aberrant activation pattern in HD CD4 T cells as measured by the number of MMD.

(a) Representative images of HD CD4 T cells treated with plasma (10%) from VP (HDc: VPp), HIC (HDc: HICp) or ART patients (HDc: ARTp) are shown. MMD were stained with cholera toxin (CtxB-AF488). For each group the top half of a representative CD4 T-cell from Z-stack images before (left) and after IL-7 stimulation (2 nM, 15 min) (right) is shown.

(b) MMD induced at the surface of CD4 T-cells (HDc) by plasmas (10%) from 5 different VP (VPp1 to VPp5). Results were obtained from the analysis of 50 cells before (white) and after (blue) IL-7 stimulation. Mean values and quartiles are shown.

(c) Comparison of the effects of plasmas from HD (HDp), VP (VPp), HIC (HICp) and ART patients (ARTp) after (blue) and before (white) IL-7 stimulation.

(d) Dose (0.01% to 10%)-response obtained with the plasmas described in c. The number of MMD induced at the surface of HDc CD4 T-cells is shown. The effect of VP plasma is shown as a plain red line.

FIGS. 5a to 5d show that plasma from VP inhibits IL-7-induced STAT5 phosphorylation and nuclear translocation of phospho-STAT5 in HD CD4 T lymphocytes.

(a) Before IL-7 stimulation, purified HD CD4 T cells were pre-incubated with plasma (10%). IL-7-induced phosphorylation and nuclear translocation of phospho-STAT5 were followed by pulsed-STED microscopy (0.5 µm slice). The following plasmas (10%) were studied: control (HDc: NS), VP (HDc: VPp), HIC (HDc: HICp) and ART patients (HDc: ARTp).

(b) Analysis of phospho-STAT5 recovered in the cytoplasm (blue) and nucleus (red) of IL-7-stimulated HD CD4 T-cells pre-treated with plasmas from 5 different VP (10%).

(c) Comparison of the effects of plasma (10%) pre-incubation on IL-7-stimulated HD CD4 T cells. Plasma were from HD (HDp), VP (VPp), HIC (HICp) and ART patients (ARTp)

(d) Dose (0.01%-10%)-response obtained with the plasmas as measured by the inhibition of phospho-STAT5 nuclear translocation in IL-7-stimulated HD CD4 T-cells. The effect of VP plasma is shown as a plain red line.

FIGS. 6a to 6d show molecular characterization of the Refractory state Inducing Factor (RIF) recovered from VP plasma.

(a) Treatment of VP plasma by trypsin, DNase, RNase and PNGase. RIF activity was followed by measuring the number of MMD and effects on IL-7-induced nuclear phospho-STAT5 in HD CD4 T-cells.

(b) RIF MW was measured by gel filtration on a Sephadex G100 column. RIF activity on HD CD4 T-cells was followed by measuring the numbers of MMD induced by the different fractions of the column (thick red curve). Each fraction was also tested for the presence of viral proteins by dot blot using polyclonal antibodies from VP plasma. Background obtained with HD plasma has been subtracted. Experiments were repeated three times.

(c) RIF MW was also measured after gel filtration on a Sephadex G100 column and its activity followed by inhibition of IL-7-induced phospho-STAT5 as measured by FACS. Percentages of maximum IL-7-induced phospho-STAT5 were recorded. The amount of protein in each fraction is also reported. Experiments were repeated twice.

(d) Isoelectric point was measured as follows. RIF eluted from the Sephadex G100 column was loaded onto an anion (MonoQ) or cation (MonoS) exchange column. RIF activity was eluted by pH-step buffers. The number of MMD on HD CD4 T-cells was plotted against pH.

FIGS. 7a to 7c show a 2D gel analysis of the IL-7 signalosome in purified CD4 T cells from HD, VP and IL-7-stimulated HD cells. (a) non-stimulated (NS) HD CD4 T-cells. (b) VP CD4 T-cells. (c) IL-7-stimulated HD CD4 T-cells.

FIGS. 8a to 8g show an analysis of the diffusion rate of IL-7Ralpha at the surface of purified CD4 T cells from HD, VP and PHA-stimulated HD cells. (a, d) at the surface of HD CD4 T-cells, (b, e) at the surface of VP CD4 T cells, (c, f) at the surface of HD CD4 T cells pre-activated with PHA (1 µg/ml). (g) Scheme of the mechanism of IL-7Ralpha diffusion embedded in MMD before and after treatment by MMD inhibitors or cytoskeleton inhibitors.

FIGS. 9a to 9d show a schematic representation of the hypothetical mode of action of RIF on HD CD4 T cells and mechanism of IL-7 unresponsiveness. RIF induces abnormal MMD which are non functional. The IL-7 signalosome is therefore altered and the cells remain unresponsive to the cytokine, as in VP CD4 T cells. Aberrant activation patterns and signalling defects in RIF-induced HD CD4 T cells and in VP CD4 T cells are undistinguishable. The left part of the scheme illustrates the different steps in the mechanisms of IL-7 signal transduction in HD (10, 12).

(a) In resting CD4 T cells, before IL-7 recognition, the IL-7R chains are associated but their intracytoplasmic domains are far apart and the signaling molecules Jak1 and Jak3 are not interacting.

(b) In IL-7-activated CD4 T cells, the IL-7R is compartmentalized in normal MMD (90 nm in diameter) and the signalosome becomes functional. After cytoskeleton organization, STAT5A and STAT5B are phosphorylated in contact with the IL-7R/Jak1/Jak3 complexes then migrate to the nucleus by moving along the microtubules as previously discussed (12).

The right part of the scheme illustrates the hypothetical mechanism of action of RIF. The proposed mechanism of action is derived from preliminary data and comparison of RIF-induced defects with the alterations characterized in purified CD4 T cells from VP (unpublished data).

(c) RIF induces many large abnormal MMDs. IL-7Rs are embedded in abnormal MMDs and their ability to induce a functional signalosome is altered.

(d) RIF-treated HD CD4 T cells are unresponsive to IL-7. Jak1 and Jak3 phosphorylate STAT5, although with reduced kinetics, but phospho-STAT5 do not migrate into the nucleus due to the lack of cytoskeleton and microtubules organization.

Panels a, b, c and d show STED microscopy images of MMD labelled with CtxB: AF488 (half pile of Z-stack from CW-STED). Panels b and d show tubulin stained with rabbit anti-tubulin/goat anti-rabbit-Atto642, actin stained with mouse anti-actin/goat-anti-mouse-Chr494 and phospho-STAT5 stained with rabbit anti-phospho-STAT5/goat-anti-rabbit-Atto642. Pulsed-STED microscopy shows a 0.5 µm slice of methanol-permeabilized CD4 T-cells. After IL-7 stimulation, actin in the MMD cytoplasmic area of RIF-treated HD CD4 T lymphocytes fails to concentrate as structured pads and does not form a cortex surrounding the nucleus, unlike in HD. Furthermore, the tubulin in these RIF-treated HD CD4 T cells, like in VP CD4 T cells, fails to form microtubules which have been hypothesized as being critical rods bridging the cytoplasm and nuclear membrane and thereby essential for STAT5 nuclear translocation.

Summary of the defects: Circled numbers 1, 2, 3 and 4 indicate the different defective steps related to the aberrant activation pattern and IL-7 unresponsiveness in RIF-treated HD T cells: (1) abnormal protein pattern of signalling complexes as described by 2D-gels, (2) abnormal membrane structures such as large MMD as seen by STED microscopy, (3) abnormal cytoskeleton organization as measured by diffusion kinetics and STED microscopy, and (4) abnormal signalling intermediate and inhibition of phospho-STAT5 nuclear translocation as shown by STED microscopy.

Figure 10:
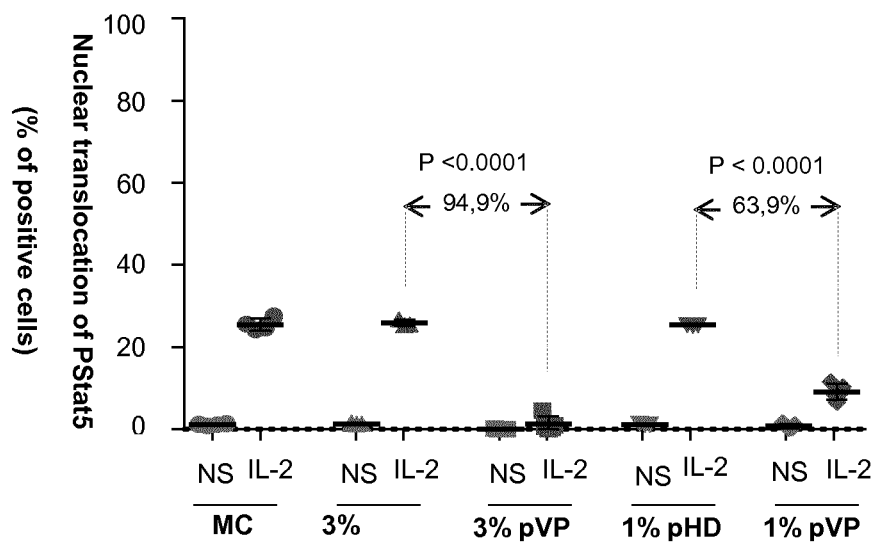
Figure 10:
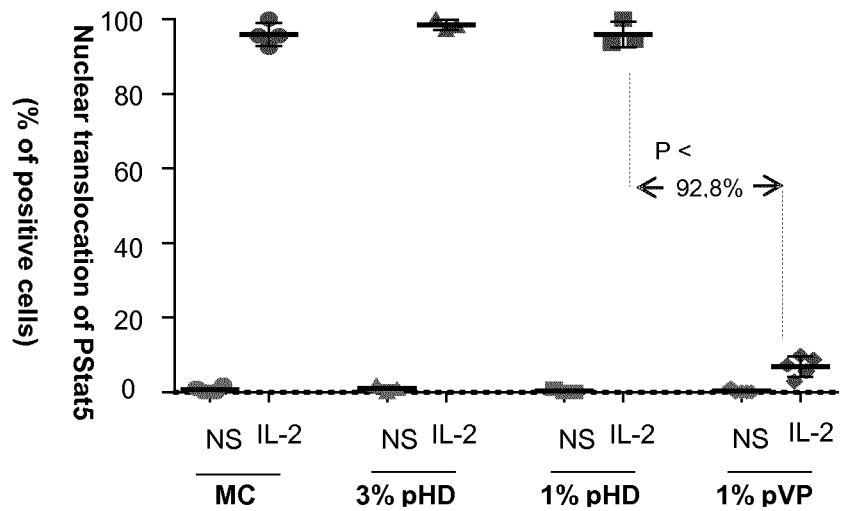

FIG. 10: PLA2sGIB inhibits IL-2 induced PStat5 nuclear translocation in CD4 T cells of healthy donors (HD): Resting CD4 T cells purified from 4 healthy donors were treated for 30 minutes at 37° C. with 3% or 1% of plasma from 5 VP (VP63, VP68, VP69, VP74 and VP75) and from 3 HD used as control. When indicated they were stimulated with 2 nM IL-2 for 15 minutes at 37° C. The percentage of cells positive for nuclear PStat5, with mean and SD, in whole CD4 T cells (a) and in CD4+ CD25+ T cells (b), before (blue points) and after IL-2 stimulation (red points) are shown. Intracellular localisation of PStat5 was observed using Laser Scanning Confocal Microscopy (LSM 700, Zeiss) after indirect staining with rabbit anti human PStat5 (pY694) followed by donkey anti rabbit IgG-Die light 405. Total CD4 T cells were stained with goat anti human b-Tubulin followed by donkey anti goat IgG-AF555. CD25+CD4 T cells were targeted with a mouse anti human CD25 followed by donkey anti mouse IgG-AF488.

Figure 11:
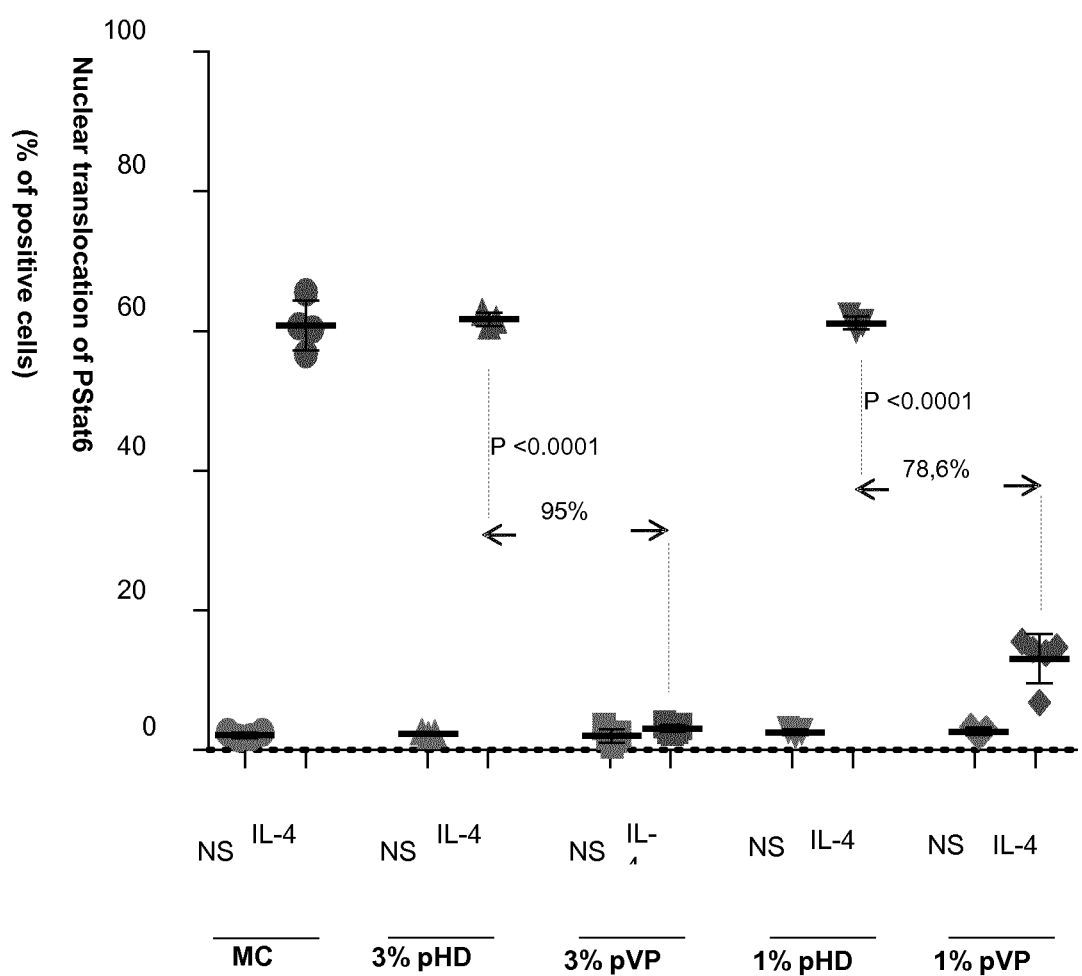

FIG. 11: PLA2sGIB inhibits IL-4 induced PStat6 nuclear translocation in CD4 T cells of healthy donors (HD): Resting CD4 T cells purified from 4 healthy donors were treated for 30 minutes at 37° C. with 3% or 1% of plasma from 5 VP (VP63, VP68, VP69, VP74 and VP75) and from 3 HD used as control. When indicated they were stimulated with 2 nM IL-4 for 15 minutes at 37° C. The percentage of cells positive for nuclear PStat6, with mean and SD, in whole CD4 T cells, before (blue points) and after IL-2 stimulation (red points) are shown. Intracellular localisation of PStat6 was observed using Laser Scanning Confocal Microscopy (LSM 700, Zeiss) after indirect staining with rabbit anti human PStat6 (pY694) followed by goat anti rabbit IgG-AF488. Total CD4 T cells were stained with mouse anti human a-Tubulin followed by goat anti mouse IgG-AF647.

Figure 12:
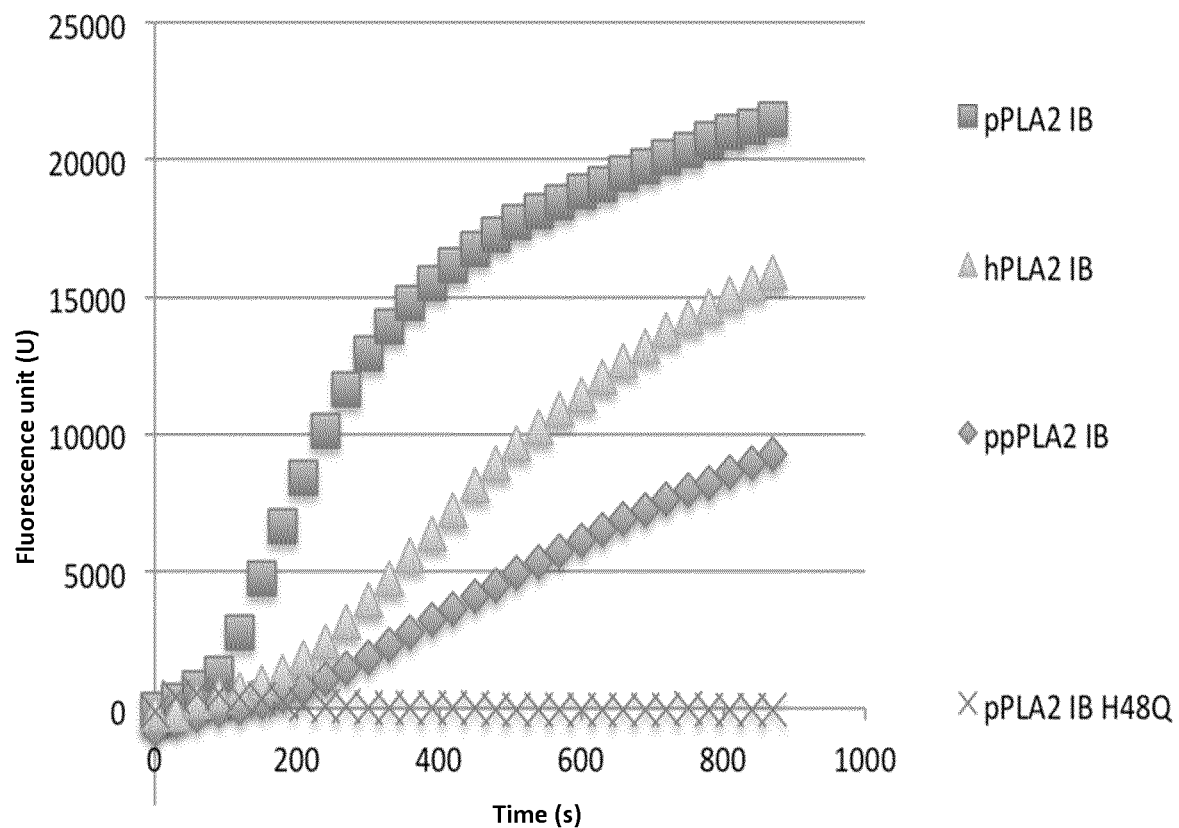

FIG. 12: Absence of activity of mutant pPLA2GIB H48Q.

Figure 13:
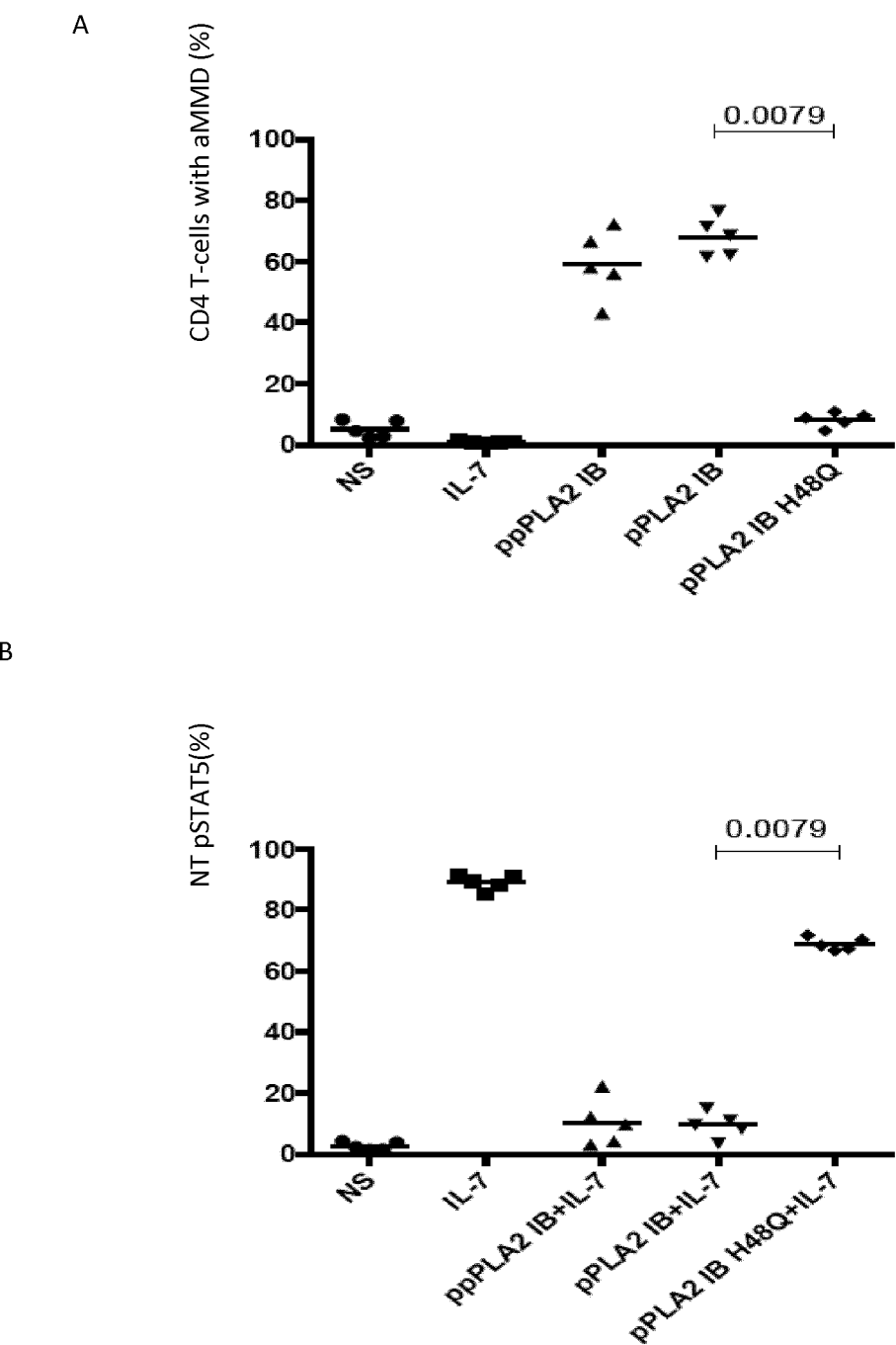

FIG. 13: Comparison of the activity of wild type cloned porcine PLA2 GIB and of its mutant H48Q. A: induction of abnormal Membrane Microdomains (aMMD); B: effect on the IL-7 induced Nuclear Translocation of phosphoSTAT5 (NT of pSTAT5).

Figure 14:
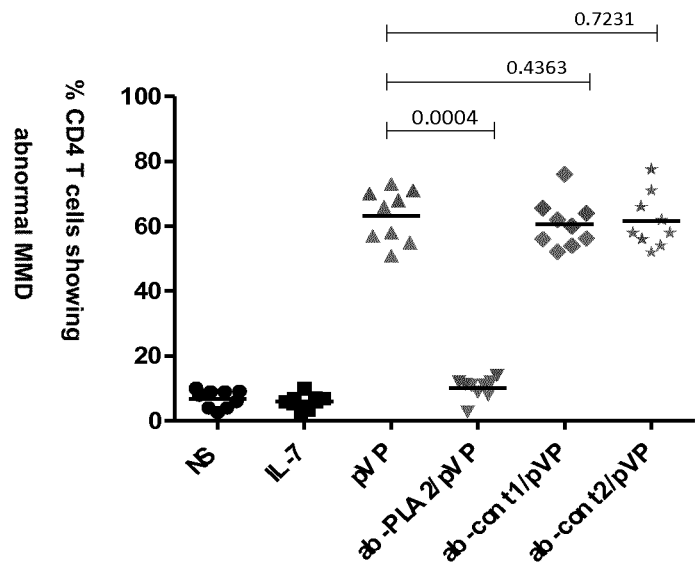
Figure 14:
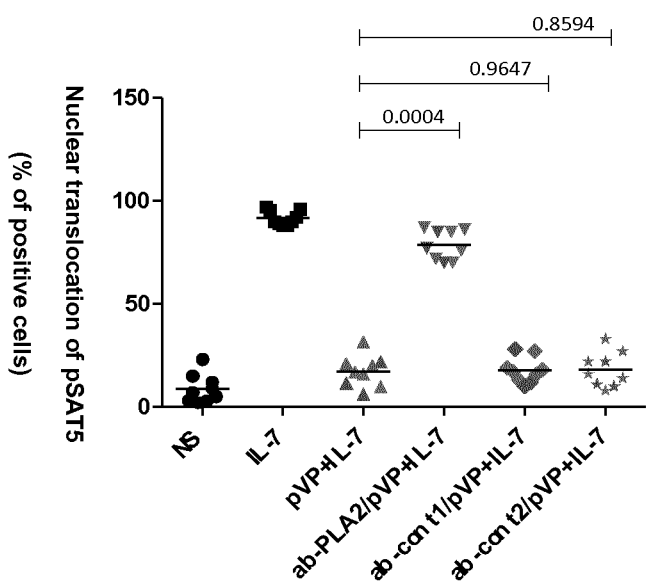

FIG. 14 shows the treatment of plasma from viremic patients with goat anti-PLA2 G1B antibodies coupled to sepharose beads. Green: VP68; pink: VP69; blue: VP LH. After treatment (30 min at room temperature) the plasmas were tested:

a. The percentage of CD4 T cells showing abnormal MMD/cell was measured after staining with Cholera toxin B (CtxB-AF488)
b. The nuclear translocation of pSTAT5 was measured after IL-7 stimulation and the percentage of positive nucleus counted.

Figure 15:
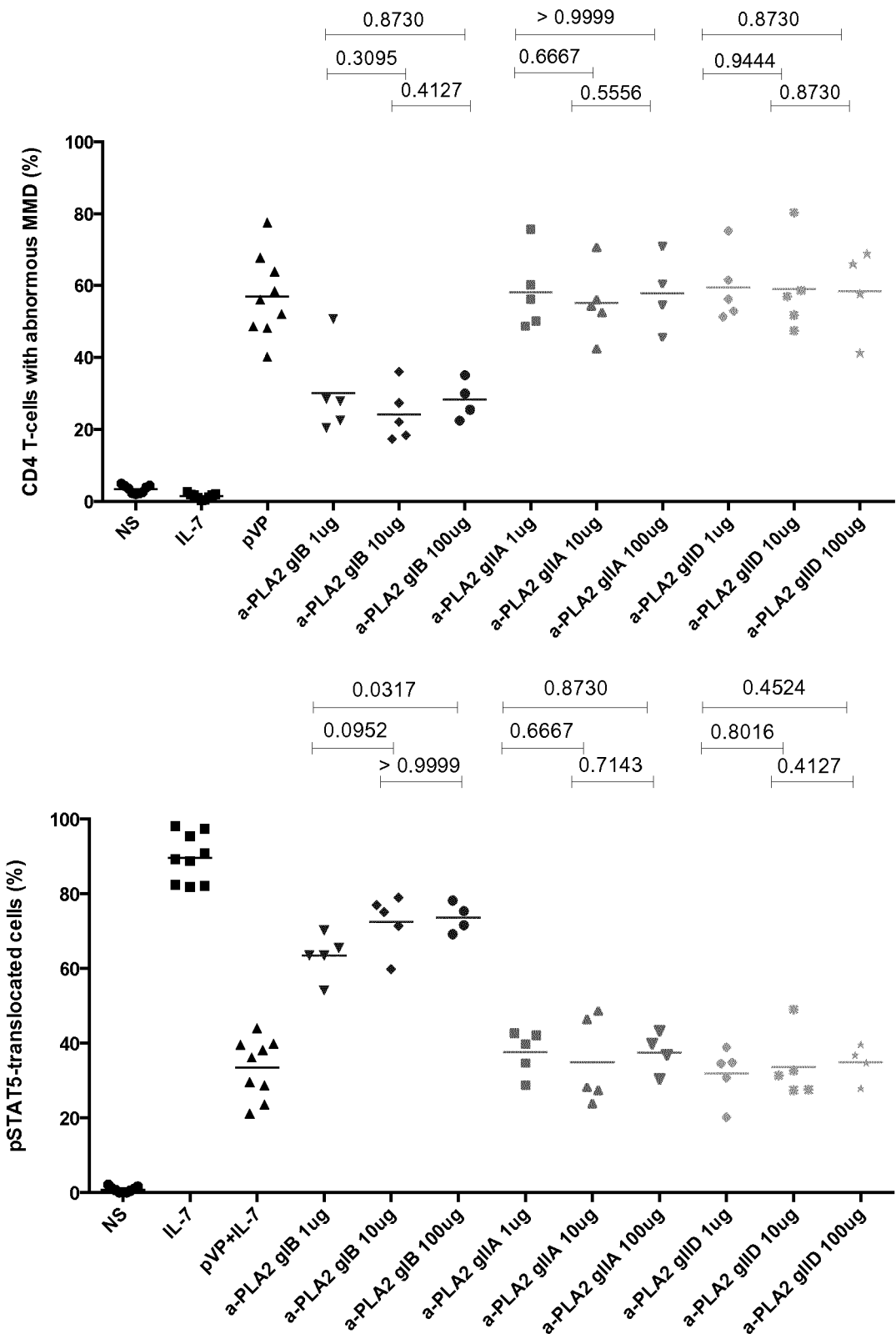

FIG. 15: Effect of anti-PLA2 GIB antibodies on the induction of aMMD and inhibition of NT pSTAT5.

Figure 16:
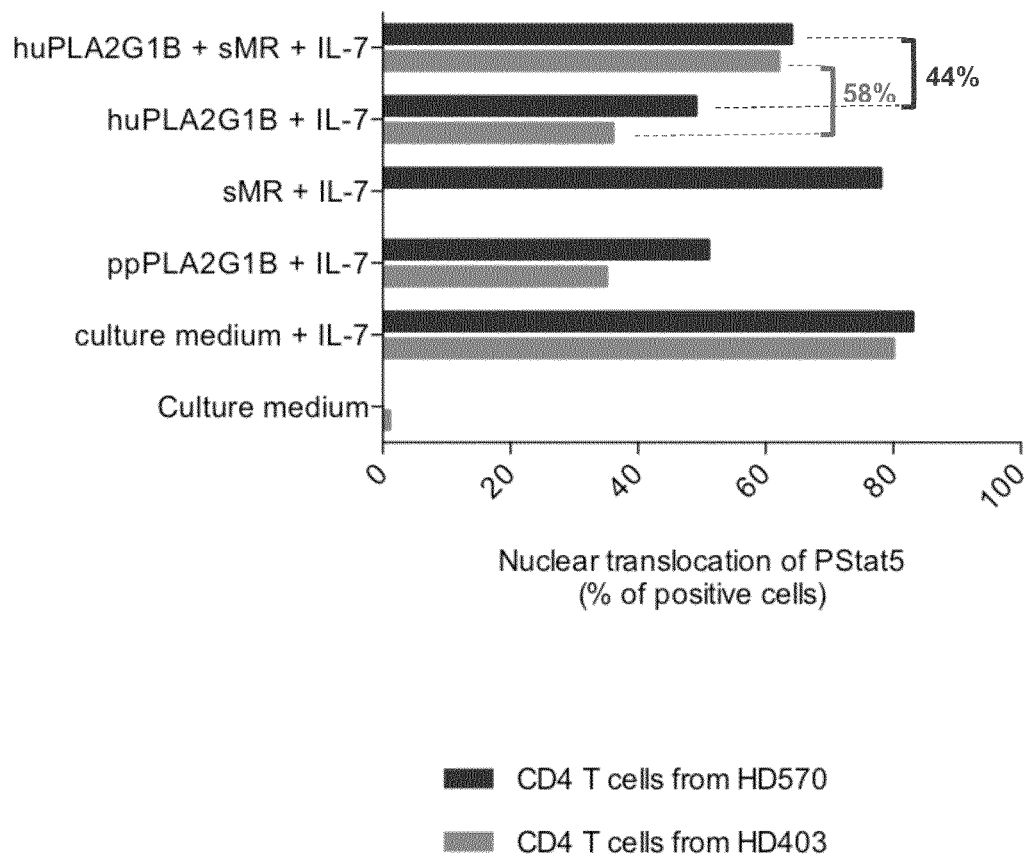

FIG. 16: Soluble PLA2G1B mouse receptor (sMR) inhibits the activity of human PLA2G1B (huPLA2G1B) on the response to IL-7 of CD4 T cells from healthy donors, expressed as the percent of cells positive for nuclear translocation of PStat5. The restoration of the response is calculated as:

$$100 \times (\% \text{ Pos cell}_{huG1B+sMR} - \% \text{ Pos cell}_{huG1B})/(\% \text{ Pos cell}_{culture\ medium} - \% \text{ Pos cell}_{huG1B})$$

Figure 17:
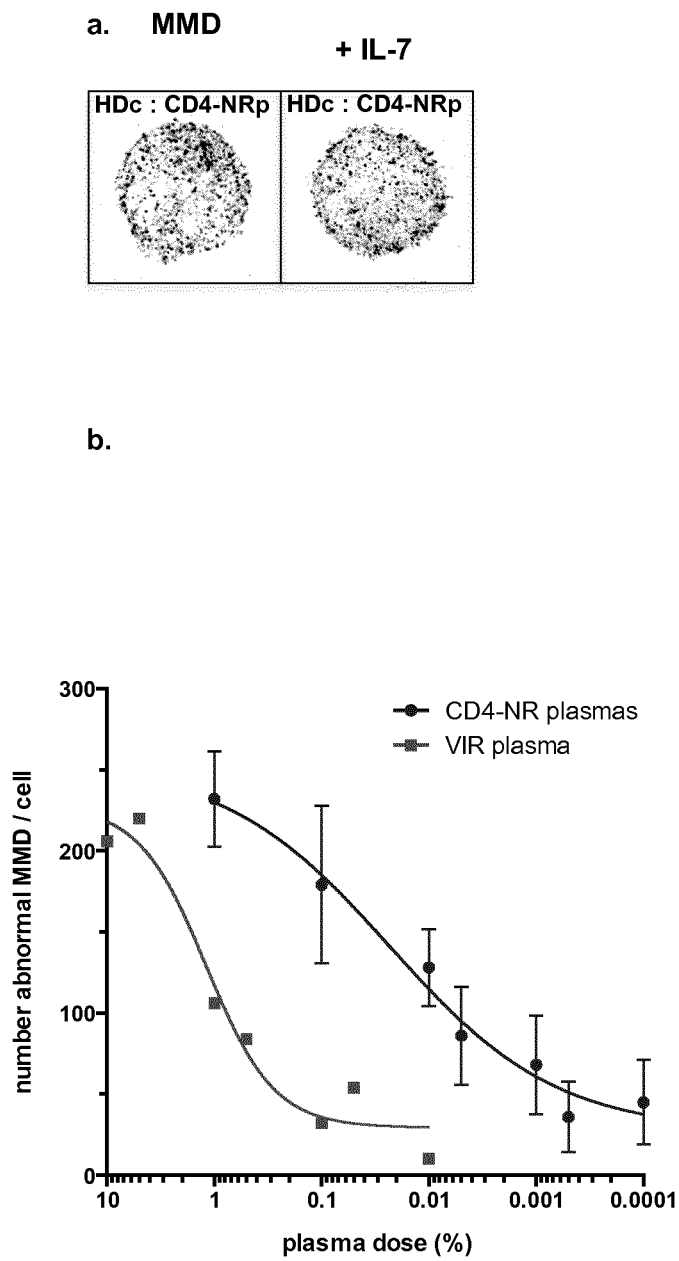

FIG. 17 shows the plasma from CD4 non-responder (CD4-NR) patients induce aberrant MMD in HD CD4 T cells—(a) Images of HD CD4 T cells treated with plasma (1%) from CD4-NR patient obtained using Structured Illumination Microscopy (SIM). MMD were stained with cholera toxin B (CtxB-AF488). Projection of Z-stacks images of a representative CD4 T cell is shown. After IL-7 stimulation (2 nM, 15 min) there is no modification of the image (right). (b) Dose curve response (0.0001% to 1%) obtained with plasmas from 5 CD4-NR patients (blue curve, mean and SD) and from a representative viremic patient (red curve). The number of abnormal MMD induced at the surface of HD CD4 T cells.

DETAILED DESCRIPTION OF THE INVENTION

The present invention relates to compositions and methods for modulating the immune system in a subject in need thereof. The invention more particularly discloses the identification of GIBsPLA2 as a key endogenous factor of the immune response and provides novel therapeutic and diagnostic methods and compositions based on a modulation of this factor.

A hypothesis of the present invention was that chronic activation of the immune system in HIV-infected patients is abnormal and drives CD4 T cells into an aberrant state of activation/differentiation that is unresponsive to the gamma-c cytokines involved in controlling many aspects of immune defenses and homeostasis of the CD4 compartment, despite the fact that more than 99.5% of CD4 T cells from the peripheral compartment are uninfected. This hypothesis was evaluated by the inventors and the present invention ellucidates the nature and significance of this aberrant state of activation.

More specifically, in a first aspect, the present invention demonstrates that the characteristics of this state may be summarized as follows: 1) before any stimulation, all the CD4 T cells in Viremic HIV-infected patients (VP) possess numerous large MMD on their surface, 2) these abnormal MMD sequester all the cell's IL-7Ralpha and gamma-c chains and 3) this sequestering of the chains in abnormal MMD alters their ability to induce the formation of a functional signalosome, 4) leading to a slowdown and a reduction of STAT5 phosphorylation and 5) a reduction of phospho-STAT5 nuclear import. This abnormal pattern of pre-existing MMD on the surface of VP CD4 T lymphocytes has multiple consequences and is a basic mechanism explaining the various manifestations of the immunodeficiency in HIV-infected patients. Loss of IL-7 responsiveness is an important factor that partly explains the CD4 lymphopenia observed. The persistent loss of these cells in VP—due to their sensitivity to apoptosis and their destruction by low-level but continuous virus proliferation—cannot be compensated despite increased levels of IL-7. In addition, since abnormal MMD sequester all the gamma-c chains in a non functional state, this blocks the function of the other cytokines in this family.

The present invention further discloses the identification of the key endogenous factor responsible for this abnormal state of the immune system in infected subjects and, more generally, responsible for a drastic modulation of the immune response in various pathophysiological conditions. Plasma samples from VP were indeed shown to contain an activity—termed RIF—which is able to induce aberrant activation of Healthy Donors (HD) CD4 T lymphocytes. RIF was found in all the plasma samples of the VP examined. The pathophysiological significance of this activity was demonstrated by its absence in HIV Controller (HIC) patients where the IL-7/IL-7R system is normal and immune activation is beneficial. RIF is also absent in the plasma of ART patients who have diminished their immune activation, restored IL-7R function and recovered CD4 counts >500/ mm$^3$ (5).

RIF thus represents a major factor that controls the immune response, particularly through a modulation of CD4 T lymphocytes. It is remarkable that RIF induces an aberrant pattern of activation in HD CD4 T cells that is undistinguishable from that observed directly ex vivo in purified VP CD4 T cells. The invention further shows that RIF is the secreted phospholipase A2 from Group I B ("PLA2 GIB"). The results disclosed in this application show that (i) over expression of PLA2 GIB leads to a potent immunosuppression and that (ii) inhibition of PLA2 GIB leads to a remarkable increase or stimulation of immune function. GIBsPLA2 inhibitors were able to correct the inappropriate state of the immune cells in plasma from subjects and can thus be used to treat (e.g., prevent, correct) immunodeficiency or immune disorders in mammals. GIBsPLA2 inhibition can also induce, stimulate, or help maintaining CD4 T cell counts and function, and thereby help stimulate efficient immune responses in patients. In particular, in HIV-infected patients, ART might be spared, or could be suspended, were an equilibrium to be reached between patient immune defenses and the virus. Were ART, given very early after infection as suggested by recent studies, to be combined with RIF inhibitors, this would prevent any RIF-induced alteration of the immune system. In addition, in the context of some current failures of ART, patients with low CD4 counts after prolonged ART may benefit from these inhibitors. Accordingly, the invention provides methods for treating a subject by modulating GIBsPLA2 expression or activity in the subject. More particularly, the invention provides a method for modulating an immune response in a subject in need thereof, comprising modulating GIBsPLA2 activity or expression in said subject.

The data provided in the examples also demonstrate that the presence of RIF in the plasma of a subject indicates the HIV-induced pathogenesis state of CD4 T cells. Accordingly, this invention provides methods of monitoring and/or diagnosing HIV infection in a subject by detecting the level of RIF in the plasma of the subject, among other things.

The data provided in the examples further demonstrate that the number and/or size of membrane microdomains (MMD) on the T-cells of a subject indicates the HIV-induced pathogenesis state of CD4 T cells. Accordingly, this disclosure also provides methods of monitoring and/or diagnosing HIV infection in a subject by measuring the number and/or size of membrane microdomains (MMD) on the T-cells of the subject, among other things.

The data provided in the examples also indicate a role for RIF in creating and/or maintaining the CD4 T cell disease state in HIV infected subjects. Accordingly, this disclosure also provides methods for identifying a candidate HIV therapeutic agent that include measuring RIF-induced CD4 T cell activation in the presence of an agent. In some embodiments the methods comprise comparing the level of RIF-induced CD4 T cell activation in the presence of the agent with the level of RIF-induced CD4 T cell activation in the absence of the agent.

Definitions

The term "sequence identity" as applied to nucleic acid or protein sequences, refers to the quantification (usually percentage) of nucleotide or amino acid residue matches between at least two sequences aligned using a standardized algorithm such as Smith-Waterman alignment (Smith and Waterman (1981) J Mol Biol 147:195-197), CLUSTALW (Thompson et al. (1994) Nucleic Acids Res 22:4673-4680), or BLAST2 (Altschul et al. (1997) Nucleic Acids Res 25:3389-3402). BLAST2 may be used in a standardized and reproducible way to insert gaps in one of the sequences in order to optimize alignment and to achieve a more meaningful comparison between them.

As used herein, "treatment" or "treat" refers to clinical intervention in an attempt to alter the natural course of the individual being treated, and can be performed either for preventive or curative purpose. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, compositions and methods of the invention are used to delay development of a disease or disorder or to slow the progression of a disease or disorder.

The term "isolated", as used herein, refers to molecules (e.g., nucleic or amino acid) that are removed from a component of their natural environment, isolated or separated, and are at least 60% free, preferably 75% free, and most preferably 90% free from other components with which they are naturally associated. An "isolated" polypeptide (or protein) is for instance a polypeptide separated from a component of its natural environment and, preferably purified to greater than 90% or 95% purity as determined by, for example, electrophoretic (e.g., SDS-PAGE, isoelectric focusing (IEF), capillary electrophoresis) or chromatographic (e.g., ion exchange or reverse phase HPLC) migration. An "isolated" nucleic acid refers to a nucleic acid molecule separated from a component of its natural environment and/or assembled in a different construct (e.g., a vector, expression cassette, recombinant host, etc.).

"Nucleic acid encoding an anti-GIBsPLA2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

A "subject" refers to a mammal. Examples of mammals include humans and non-human animals such as, without limitation, domesticated animals (e.g., cows, sheep, cats, dogs, and horses), non-human primates (such as monkeys), rabbits, and rodents (e.g., mice and rats).

The "modulation of an immune response" designates, within the context of the invention, any modification of the amount or activity or ratio of immune cells, preferably white blood cells (e.g., T lymphocytes, B lymphocytes, NK, NKT cells, macrophages, dendritic cells). In a particular embodiment, modulating an immune response includes modulating the amount or activity of T lymphocytes, preferably of CD4-T lymphocytes.

Refractory State Inducing Factor (RIF) or Phospholipase A2 Group IB

The term RIF is used interchangeably with Phospholipase A2 group IB, GIBsPLA2 (or PLA2 GIB). Phospholipase A2 group D3 is a secreted protein having a MW of from about 15 kDa and an isoelectric point of from about 6.5 to about 8.0.

Within the context of the present invention, the term "GIBsPLA2" or "phospholipase A2 group TB" designates any native GIBsPLA2 protein from any vertebrate source, including mammals such as primates (e.g. humans) and rodents (e.g., mice and rats), unless otherwise indicated. The term encompasses "full-length," unprocessed GIBsPLA2, as well as any form of GIBsPLA2 that results from processing inside or outside a cell. The term also encompasses naturally-occurring variants of GIBsPLA2, e.g., splice variants or allelic variants.

The amino acid sequence of an exemplary human GIBsPLA2 is shown below (SEQ ID NO: 2).

```
MKLLVLAVLL TVAAADSGIS PRAVWQFRKM IKCVIPGSDP

FLEYNNYGCY CGLGGSGTPV DELDKCCQTH DNCYDQAKKL

DSCKFLLDNP YTHTYSYSCS GSAITCSSKN KECEAFICNC

DRNAAICFSK APYNKAHKNL DTKKYCQS
```

Amino acids 1 to 15 of SEQ ID NO: 2 (underlined) are a signal sequence, and amino acids 16 to 22 of SEQ ID NO: 2 (in bold) are a propeptide sequence. The mature protein corresponds to amino acid residues 23-148 of SEQ ID NO: 2, which is an exemplary processed human GIBsPLA2 protein.

Naturally-occurring variants include any protein comprising the sequence of SEQ ID NO: 2, or the sequence of amino acid residues 23-148 of SEQ ID NO: 2, with one or more amino acid substitution, addition and/or deletion of one or several (typically 1, 2 or 3) amino acid residues, preferably not more than 10 distinct amino acid substitution(s), addition(s), and/or deletion(s) of one or several (typically 1, 2 or 3) amino acid residues. Typical naturally-occurring variants retain a biological activity of SEQ ID NO: 2.

In this regard, in some embodiments, GIBsPLA2 has at least one activity selected from induction of formation of membrane microdomains (MMD) in CD4 T cells from healthy subjects, or rendering CD4 T cells of healthy subjects refractory to interleukin signaling, such as refractory to IL-2 signaling or refractory to IL-7 signaling.

In some embodiments inducing formation of MMD comprises increasing the number of MMD on CD4 T cells of healthy subjects to at least about 80 per cell, at least about 90 per cell, at least about 100 per cell, at least about 110 per cell, or at least about 120 per cell. In a non-limiting preferred embodiment, inducing formation of MMD comprises increasing the number of MMD on CD4 T cells of healthy subjects to more than 100 MMD per cell.

In some embodiments inducing formation of MMD comprises stimulating formation of larger MMD than would otherwise be present on the CD4 T cells. In some embodiments inducing formation of larger MMD comprises stimulating formation MMD having a diameter of at least 100 nm, at least 110 nm, at least 120 nm, at least 130 nm, or at least 140 nm. In a non-limiting preferred embodiment, inducing formation of larger MMD comprises stimulating formation of MMD having a diameter larger than 120 nm.

In some embodiments rendering CD4 T cells of healthy subjects refractory to interleukin-7 signaling comprises a reduction of STAT5A and/or B phosphorylation in said cells by at least about 10%, at least about 20%, at least about 30%, or at least about 40%. In some embodiments rendering CD4 T cells of healthy subjects refractory to interleukin-7 signaling comprises reducing the rate of nuclear translocation of phospho-STAT5A and/or phospho-STAT5B by at least about 20%, at least about 30%, at least about 40%, or at least about 50%.

GIBsPLA2 activity may be measured by any suitable method known in the art, as illustrated in the examples, or later developed. GIBsPLA2 activity may be measured in a plasma sample such as for example a fractionated plasma sample, using e.g., ligand recruitment assays, immunoassays and/or enzymatic assays.

In a particular embodiment, the term GIBsPLA2 designates a human protein, particularly a protein comprising or having SEQ ID NO: 2, or a naturally-occurring variant thereof. GIBsPLA2 according to this disclosure may be isolated, purified, and/or recombinant. In certain embodiments, the invention may use, instead or in addition to a GIBsPLA2 protein, a nucleic acid encoding GIBsPLA2. The nucleic acid may be DNA or RNA, single- or double-stranded.

An exemplary nucleic acid sequence encoding a GIBs-PLA2 is shown in SEQ ID NO: 1 below.

```
ATGAAACTCCTTGTGCTAGCTGTGCTGCTCACAGTGGCCGCCGCCGACAG
CGGCATCAGCCCTCGGGCCGTGTGGCAGTTCCGCAAAATGATCAAGTGCG
TGATCCCGGGGAGTGACCCCTTCTTGGAATACAACAACTACGGCTGCTAC
TGTGGCTTGGGGGGCTCAGGCACCCCCGTGGATGAACTGGACAAGTGCTG
CCAGACACATGACAACTGCTACGACCAGGCCAAGAAGCTGGACAGCTGTA
AATTTCTGCTGGACAACCCGTACACCCACACCTATTCATACTCGTGCTCT
GGCTCGGCAATCACCTGTAGCAGCAAAAACAAAGAGTGTGAGGCCTTCAT
TTGCAACTGCGACCGCAACGCTGCCATCTGCTTTTCAAAAGCTCCATATA
ACAAGGCACACAAGAACCTGGACACCAAGAAGTATTGTCAGAGTTGA
```

Alternative nucleic acid molecules encoding a GIBsPLA2 include any variant of SEQ ID NO:1 resulting from the degeneracy of the genetic code, as well as any sequence which hybridizes to SEQ ID NO: 1 under stringent conditions, more preferably having at least 80%, 85%, 90%, 95% or more sequence identity to SEQ ID NO; 1, and encoding a GIBsPLA2 protein.

Method of Production of GIBsPLA2

GIBsPLA2 can be produced by any conventionally known protein expression method and purification method. For example: (i) a method for synthesizing peptides; (ii) a method for purifying and isolating them from the living body or cultured cells; or (iii) a method for producing them with the use of genetic recombination techniques; and combinations thereof and the like (for example, the standard techniques described for example in Molecular Cloning (Sambrook, J., Fritsch, E. F., Maniatis, T., Cold Spring Harbor Laboratory Press) (1989) and Current Protocols in Molecular Biology (Ausubel, F. M., John Wiley and Sons, Inc. (1989)).

In a particular embodiment, the invention relates to a method for producing GIBsPLA2 by expression of a coding nucleic acid in a host cell, and collection or purification of GIBsPLA2. In this regard, the invention also described recombinant host cells comprising a nucleic acid encoding a GIBsPLA2. Such cells may be prokaryotic (such as bacteria) or eukaryotic (such as yeast cells, insect cells, plant cells or mammalian cells). The nucleic acid may be placed under the control of any suitable regulatory sequence, such as a promoter, terminator, and the like. Alternatively, the nucleic acid may be inserted in the host cell in a location where expression is driven by an endogenous promoter. Techniques for inserting nucleic acids in cells are well known in the art.

GIBsPLA2 Modulation

The invention provides novel methods which comprise a modulation of GIBsPLA2 in a subject in need thereof. The term "modulation" designates any modification of the level (e.g., expression) or activity of GIBsPLA2 in a subject. Also, modulation designates either an increase or a decrease GIBsPLA2 level or activity. A modulation more preferably designates a change by at least 10%, 20%, 30%, 40%, 50%, 60%, 70%, 80% or more as compared to non-modulated situation. As a result, inhibiting GIBsPLA2 designates reducing by at least 10%, 20%, 30%, 40%, 50%, 60%, 70%, 80% or more GIBsPLA2 level or activity, as well as completely blocking or suppressing GIBsPLA2 level or activity. Conversely, stimulating GIBsPLA2 designates increasing by at least 10%, 20%, 30%, 40%, 50%, 60%, 70%, 80% or more GIBsPLA2 level or activity. Depending on the situation, the modulation may be transient, sustained or permanent. Also modulating the activity includes modulating the amount of GIBsPLA2 in the subject, particularly in body fluids, modulating the potency of the protein (for instance by modulating the level of co-factors or substrate in the subject), and modulating the level or activity of degradation products produced by GIBsPLA2.

GIBsPLA2 Inhibition

In a particular embodiment, the invention provides compositions and methods for inhibiting GIBsPLA2 in a subject. GIBsPLA2 inhibition may be obtained by the use of GIBsPLA2 inhibitors, i.e., any compound that inhibit the expression or activity of GIBsPLA2. GIBsPLA2 inhibitors include expression inhibitors, antagonists, sequestrators, or target masking compounds. Preferred types of GIBsPLA2 inhibitors include GIBsPLA2 ligands (covalent or non-covalent), anti-GIBsPLA2 antibodies (and fragments and derivatives thereof), nucleic acids encoding anti-GIBsPLA2 antibodies (or fragments and derivatives thereof), inhibitory nucleic acids, peptides, or small drugs, or combination(s) thereof. Alternatively, or in addition, GIBsPLA2 inhibition can be obtained by vaccinating a subject against a GIBsPLA2 antigen, so that antibodies are produced by the subject in need of PLA2-GIB inhibition.

Antibodies against GIBsPLA2

Specific examples of GIBsPLA2 inhibitors are antibodies that specifically bind to GIBsPLA2.

Antibodies can be synthetic, monoclonal, or polyclonal and can be made by techniques well known in the art. Such antibodies specifically bind via the antigen-binding sites of the antibody (as opposed to non-specific binding). GIBsPLA2 polypeptides, fragments, variants, fusion proteins, etc., can be employed as immunogens in producing antibodies immunoreactive therewith. More specifically, the polypeptides, fragments, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Both polyclonal and monoclonal antibodies can be prepared by conventional techniques.

Preferred antibodies of the invention are directed to a GIBsPLA2 epitope, and/or have been generated by immunization with a polypeptide comprising a GIBsPLA2 epitope selected from: the mature GIBsPLA2 protein, a fragment of GIBsPLA2 comprising at least 8 consecutive amino acid residues of SEQ ID NO: 2 (or the corresponding residues of a natural variant of SEQ ID NO: 2), said fragment comprising at least amino acid 70, amino acid 121, amino acid 50, amino acid 52, amino acid 54, amino acid 71, or a combination thereof. Preferred antibodies of the invention bind an epitope comprised between amino acid residues 50-71 of SEQ ID NO: 2 or the corresponding residues of a natural variant of SEQ ID NO: 2.

The term "antibodies" is meant to include polyclonal antibodies, monoclonal antibodies, fragments thereof, such as F(ab')2 and Fab fragments, single-chain variable fragments (scFvs), single-domain antibody fragments (VHHs or Nanobodies), bivalent antibody fragments (diabodies), as well as any recombinantly and synthetically produced binding partners, human antibodies or humanized antibodies.

Antibodies are defined to be specifically binding preferably if they bind to GIBsPLA2 with a Ka of greater than or equal to about $10^7$ M−1. Affinities of antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, donkeys, goats, sheep, dogs, chickens, rabbits, mice, or rats, using procedures that are well known in the art. In general, purified GIBsPLA2 or a peptide based on the amino acid sequence of GIBsPLA2 that is appropriately conjugated is administered to the host animal typically through parenteral injection. The immunogenicity of GIBsPLA2 can be enhanced through the use of an adjuvant, for example, Freund's complete or incomplete adjuvant. Following booster immunizations, small samples of serum are collected and tested for reactivity to GIBsPLA2 polypeptide. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresi s (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: A New Dimension in Biological Analyses, Plenum Press, Kennett, McKeam, and Bechtol (eds.), 1980.

For example, the host animals, such as mice, can be injected intraperitoneally at least once and preferably at least twice at about 3 week intervals with isolated and purified wild-type or mutant GIBsPLA2 protein or conjugated GIBsPLA2 peptide, optionally in the presence of adjuvant. Mouse sera are then assayed by conventional dot blot technique or antibody capture (ABC) to determine which animal is best to fuse. Approximately two to three weeks later, the mice are given an intravenous boost of protein or peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled GIBsPLA2 polypeptide, is added to each well followed by incubation. Positive wells can be subsequently detected. Positive clones can be grown in bulk culture and supernatants are subsequently purified over a Protein A column (Pharmacia).

The monoclonal antibodies of the disclosure can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present disclosure include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May, 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

For therapeutic applications, "human" monoclonal antibodies having human constant and variable regions are often preferred so as to minimize the immune response of a patient against the antibody. Such antibodies can be generated by immunizing transgenic animals which contain human immunoglobulin genes. See Jakobovits et al. Ann NY Acad Sci 764:525-535 (1995).

Human monoclonal antibodies against GIBsPLA2 polypeptides can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) J. Mol. Biol. 222:581 597; and Griffiths et al. (1993) EMBO J 12:725 734. In addition, a combinatorial library of antibody variable regions can be generated by mutating a known human antibody. For example, a variable region of a human antibody known to bind GIBsPLA2, can be mutated by, for example, using randomly altered mutagenized oligonucleotides, to generate a library of mutated variable regions which can then be screened to bind to GIBsPLA2. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) Proc. Nat'l Acad. Sci. USA 89:4457 4461.

An immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) Bio/Technology 9:1370 1372; Hay et al. (1992) Hum Antibod Hybridomas 3:81 85; Huse et al. (1989) Science 246:1275 1281; Griffiths et al. (1993) supra; Hawkins et al. (1992) J Mol Biol 226:889 896; Clackson et al. (1991) Nature 352:624 628; Gram et al. (1992) PNAS 89:3576 3580; Garrad et al. (1991) Bio/Technology 9:1373 1377; Hoogenboom et al. (1991) Nuc Acid Res 19:4133 4137; and Barbas et al. (1991) PNAS 88:7978 7982. Once displayed on the surface of a display package (e.g., filamentous phage), the antibody library is screened to identify and isolate packages that express an antibody that binds a GIBsPLA2 polypeptide. In a preferred embodiment, the primary screening of the library involves panning with an immobilized GIBsPLA2 polypeptide and display packages expressing antibodies that bind immobilized GIBsPLA2 polypeptide are selected.

In a particular embodiment, the invention relates to a composition comprising an anti-GIBsPLA2 antibody (or a fragment or derivative thereof) and a pharmaceutically acceptable excipient.

Existing anti-Phospholipase A2-GIB monoclonal antibodies include Mab CH-7 (Labome), MAB5018 (Labome), EPR5186 (Genetex); LS-C138332 (Lifespan) or CABT-17153MH (creative biomart). Examples of polyclonal antibodies include for instance N1C3 from GeneTex. As indicated above, preferred anti-GIBsPLA2 antibodies of the invention bind mature GIBsPLA2, even more preferably an epitope comprised in a domain of GIBsPLA2 comprising an amino acid selected from amino acid 70, amino acid 121, amino acid 50, amino acid 52, amino acid 54, amino acid 71, or a combination thereof. Preferred antibodies of the invention bind an epitope comprised between amino acid residues 50-71 of SEQ ID NO: 2 or the corresponding residues of a natural variant of SEQ ID NO: 2.

In an alternative embodiment, the invention relates to and uses a composition comprising a nucleic acid encoding an anti-GIBsPLA2 antibody (or a fragment or derivative thereof) and a pharmaceutically acceptable excipient.

Inhibitory Nucleic Acids

In an alternative embodiment, the GIBsPLA2 inhibitor is an inhibitory nucleic acid, i.e., any nucleic acid molecule which inhibits GIBsPLA2 gene or protein expression. Preferred inhibitory nucleic acids include antisense nucleic acids, short interfering RNAs (siRNAs), small hairpin RNAs (shRNA), microRNAs, aptamers, or ribozymes. In a particular embodiment, the inhibitory nucleic acid is a small interfering RNA that prevents translation of GIBsPLA2 mRNA. In another particular embodiment, the inhibitory nucleic acid is an antisense oligonucleotide that prevents translation of GIBsPLA2 mRNA. In another particular embodiment, the inhibitory nucleic acid is a small hairpin RNA that prevents translation of GIBsPLA2 mRNA.

siRNA comprise a sense nucleic acid sequence and an anti-sense nucleic acid sequence of the polynucleotide of interest. siRNA are constructed such that a single transcript (double stranded RNA) have both the sense and complementary antisense sequences from the target gene. The nucleotide sequence of siRNAs may be designed using an siRNA design computer program available from, for example, the Ambion website on the world wide web.

In some embodiments, the length of the antisense oligonucleotide or siRNAs is less than or equal to 10 nucleotides. In some embodiments, the length of the antisense oligonucleotides and siRNAs is as long as the naturally occurring transcript. In some embodiments, the antisense oligonucleotides and siRNAs have 18-30 nucleotides. In some embodiments, the antisense oligonucleotides and siRNAs are less than 25 nucleotides in length.

Preferred inhibitory nucleic acid molecules comprise a domain having a nucleotide sequence that is perfectly complementary to a region of a GIBsPLA2 gene or RNA. Such a domain contains typically from 4 to 20 nucleotides, allowing specific hybridization and optimal inhibition the gene transcription or RNA translation. The sequence of the inhibitory nucleic acids may be derived directly from the sequence of a gene encoding GIBsPLA2, such as SEQ ID NO: 1. Alternatively, or in addition, inhibitory nucleic acids may hybridize to a regulatory element in a GIBsPLA2 gene or RNA, such as a promoter, a splicing site, etc., and prevent effective regulation thereof.

Specific examples of inhibitory nucleic acid molecules of the present invention include isolated single strand nucleic acid molecules consisting of from 10 to 50 consecutive nucleotides of SEQ ID NO: 1. Specific examples of inhibitory nucleic acid molecules of the invention are antisense nucleic acids consisting of the following nucleotide sequence or the perfectly complementary strand thereof:

(SEQ ID NO: 3)
ATGAAACTCCTTGTGCTAG (SEQ ID NO: 4)
ACAGCGGCATCAGC

-continued

```
                                           (SEQ ID NO: 5)
TTCCGCAAAATGATCAA (SEQ ID NO: 6)
CCCGGGGAGTGACCCC (SEQ ID NO: 7)
TACGGCTGCTACTGTGGCTT (SEQ ID NO: 8)
GACACATGACAACTGCTACGACC (SEQ ID NO: 9)
ACCCACACCTATTCATACTCGT (SEQ ID NO: 10)
ATCACCTGTAGCAGCA (SEQ ID NO: 11)
AGCTCCATATAACAAGGCA (SEQ ID NO: 12)
CAAGAAGTATTGTCAGAG
```

Peptide and Small Drugs

In an alternative embodiment, the GIBsPLA2 inhibitor is a peptide or small drug that inhibits the activity of GIBsPLA2. The peptide or small drug is typically a molecule that selectively binds GIBsPLA2, or a substrate of GIBsPLA2, or a co-factor of GIBsPLA2, or a degradation product or metabolite of GIBsPLA2 pathway.

Peptides preferably contain from 3 to 20 amino acid residues, and their sequence may be identical to a domain of GIBsPLA2 (bait peptide) or to a domain of a GIBsPLA2 substrate, co-factor, degradation product or metabolite. Preferred peptides of the invention contain from 4 to 30 consecutive amino acid residues of SEQ ID NO: 2 (or of a corresponding sequence of a natural variant of SEQ ID NO: 2). Most preferred peptides of the invention comprise from 5 to 25 consecutive amino acid residues of SEQ ID NO: 2 (or of a corresponding sequence of a natural variant of SEQ ID NO: 2) and further comprise at least one of the following amino acid residues of SEQ ID NO: 2 (or of a corresponding sequence of a natural variant of SEQ ID NO: 2): amino acid 70, amino acid 121, amino acid 50, amino acid 52, amino acid 54, amino acid 71, or a combination thereof. Specific examples of peptides of the invention are peptides of less than 25 amino acids comprising anyone of the following sequences:

```
                                           (SEQ ID NO: 13)
NNYGCY (SEQ ID NO: 14)
CYCGLG (SEQ ID NO: 15)
YNNYGCYCGLGGSG (SEQ ID NO: 16)
FLEYNNYGCYCGLGGSGTPV (SEQ ID NO: 17)
QTHDN (SEQ ID NO: 18)
CQTHDNC (SEQ ID NO: 19)
ECEAFICNC (SEQ ID NO: 20)
DRNAAI (SEQ ID NO: 21)
DRNAAICFSKAPYNKAHKNL
```

The peptides of the invention can comprise peptide, non-peptide and/or modified peptide bonds. In a particular embodiment, the peptides comprise at least one peptidomimetic bond selected from intercalation of a methylene (—CH$_2$—) or phosphate (—PO$_2$—) group, secondary amine (—NH—) or oxygen (—O—), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, methyleneoxy, cetomethylene, esters, phosphinates, phosphinics, or phosphonamides. Also, the peptides may comprise a protected N-ter and/or C-ter function, for example, by acylation, and/or amidation and/or esterification.

The peptides of the invention may be produced by techniques known per se in the art such as chemical, biological, and/or genetic synthesis.

Each of these peptides, in isolated form, represents a particular object of the present invention.

Preferred small drugs are hydrocarbon compounds that selectively bind GIBsPLA2.

Small drugs and peptides are preferably obtainable by a method comprising: (i) contacting a test compound with GIBsPLA2 or a fragment thereof, (ii) selecting a test compound which binds GIBsPLA2 or said fragment thereof, and (iii) selecting a compound of (ii) which inhibits an activity of GIBsPLA2. Such a method represents a particular object of the invention.

Small drugs and peptides are also obtainable by a method comprising: (i) contacting a test compound with a GIBsPLA2 substrate, co-factor, or degradation product, or a fragment thereof, (ii) selecting a test compound which binds to said GIBsPLA2 substrate, co-factor, or degradation product, or a fragment thereof, and (iii) selecting a compound of (ii) which inhibits an activity of GIBsPLA2. Such a method represents a particular object of the invention.

GIBsPLA2 Soluble Receptors

In an alternative embodiment, the GIBsPLA2 inhibitor is a soluble form of a GIBsPLA2 receptor. Such soluble receptor compounds are able to bind GIBsPLA2, thereby inhibiting its activity by acting as a bait or masking agent.

A specific embodiment of such inhibitors is a soluble form of a human or murine GIBsPLA2 receptor, or a GIBsPLA2-binding fragment thereof.

The amino acid sequences of murine and human soluble receptors are depicted in SEQ ID NOs: 22 and 23, respectively. The term soluble receptor thus encompasses any GIBsPLA2-binding polypeptide comprising all or a fragment of the sequence of SEQ ID NO: 22 or 23.

A GIBsPLA2-binding fragment designates any fragment of such a polypeptide comprising preferably at least 5 consecutive amino acid residues thereof, more preferably at least 8, 10, or 12, which binds PLA2GIB specifically. Specific binding of the receptor molecule indicates that the receptor molecule binds to PLA2GIB with higher affinity (e.g., by at least 5 fold) than to PLA2-IIA or IID. A fragment as defined above most preferably comprises less than 50 amino acid residues.

Examples of GIBsPLA2-binding polypeptides are, without limitation, polypeptides comprising at least one of the following amino acid sequences:

```
LSLYECDSTLVSLRWRCNRKMITGPLQYSVQVAHDNTVVASRKYIHKW         (SEQ ID NO: 24)

WEKDLNSHICYQFNLLS                                        (SEQ ID NO: 25)

DCESTLPYICKKYLNHIDHEIVEK                                 (SEQ ID NO: 26)

QYKVQVKSDNTVVARKQIHRWIAYTSSGGDICE                        (SEQ ID NO: 27)

LSYLNWSQEITPGPFVEHHCGTLEVVSA                             (SEQ ID NO: 28)

SRFEQAFITSLISSVAEKDSYFW                                  (SEQ ID NO: 29)

WICRIPRDVRPKFPDWYQYDAPWLFYQNA                            (SEQ ID NO: 30)

AFHQAFLTVLLSRLGHTHWIGLSTTDNGQT                           (SEQ ID NO: 31)
```

SEQ ID NOs: 24-26 derive from the sequence of human soluble PLA2GIB receptor, while SEQ ID NOs: 27-31 derive from the sequence of murine soluble PLA2GIB receptor.

Vaccination

In an alternative (or cumulative) embodiment, inhibition of GIBsPLA2 in a subject is obtained by vaccinating (or immunizing) the subject with a GIBsPLA2 antigen. As a result of such a vaccination or immunization, the subject produces antibodies (or cells) which inhibit GIBsPLA2. In particular, injection(s) of a GIBsPLA2 antigen (e.g., an immunogenic GIBsPLA2 essentially devoid of biological activity) can generate antibodies in the treated subject. These antibodies will protect against an excess of GIBsPLA2 expression and can be used along as immunotherapy or a vaccine prophyllaxy.

An object of the invention thus resides in a method of vaccinating a subject comprising administering to the subject a GIBsPLA2 antigen.

A further object of the invention relates to a GIBsPLA2 antigen for use to vaccinate a subject in need thereof.

In a particular embodiment, the GIBsPLA2 antigen used for vaccination is an inactivated immunogenic molecule that induces an immune response against GIBsPLA2 in a subject. Inactivation may be obtained e.g., by chemically or physically altering GIBsPLA2 or by mutating or truncating the protein, or both; and immunogenicity may be obtained as a result of the inactivation and/or by further conjugating the protein to a suitable carrier or hapten, such as KLH, HSA, polylysine, a viral anatoxin, or the like, and/or by polymerization, or the like. The antigen may thus be chemically or physically modified, e.g., to improve its immunogenicity.

In a preferred embodiment, the GIBsPLA2 antigen of the invention comprises GIBsPLA2 or an epitope-containing fragment or mimotope thereof.

In a particular embodiment, the GIBsPLA2 antigen comprises a full length GIBsPLA2 protein. In a further particular embodiment, the GIBsPLA2 antigen comprises a protein comprising SEQ ID NO: 2, or a sequence having at least 90% identity to SEQ ID NO: 2.

In an alternative embodiment, the GIBsPLA2 antigen comprises a fragment of a GIBsPLA2 protein comprising at least 6 consecutive amino acid residues and containing an immunogenic epitope, or a mimotope thereof. In a preferred embodiment, the GIBsPLA2 antigen comprises at least from 6 to 20 amino acid residues. Preferred peptides of the invention contain from 4 to 30 consecutive amino acid residues of SEQ ID NO: 2 (or of a corresponding sequence of a natural variant of SEQ ID NO: 2). Most preferred peptides of the invention comprise from 5 to 25 consecutive amino acid residues of SEQ ID NO: 2 (or of a corresponding sequence of a natural variant of SEQ ID NO: 2) and further comprise at least one of the following amino acid residues of SEQ ID NO: 2 (or of a corresponding sequence of a natural variant of SEQ ID NO: 2): amino acid 70, amino acid 121, amino acid 50, amino acid 52, amino acid 54, amino acid 71, or a combination thereof. Specific examples of peptides of the invention are peptides of less than 50 amino acids comprising anyone of the following sequences:

```
NNYGCY                          (SEQ ID NO: 13)

CYCGLG                          (SEQ ID NO: 14)

YNNYGCYCGLGGSG                  (SEQ ID NO: 15)

FLEYNNYGCYCGLGGSGTPV            (SEQ ID NO: 16)

QTHDN                           (SEQ ID NO: 17)

CQTHDNC                         (SEQ ID NO: 18)

ECEAFICNC                       (SEQ ID NO: 19)

DRNAAI                          (SEQ ID NO: 20)

DRNAAICFSKAPYNKAHKNL            (SEQ ID NO: 21)
```

The GIBsPLA2 antigen may be in various forms such as in free form, polymerized, chemically or physically modified, and/or coupled (i.e., linked) to a carrier molecule. Coupling to a carrier may increase the immunogenicity and (further) suppress the biological activity of the GIBsPLA2 polypeptide. In this regard, the carrier molecule may be any carrier molecule or protein conventionally used in immunology such as for instance KLH (Keyhole limpet hemocyanin), ovalbumin, bovine serum albumin (BSA), a viral or bacterial anatoxin such as toxoid tetanos, toxoid diphteric B cholera toxin, mutants thereof such as diphtheria toxin CRM 197, an outer membrane vesicle protein, a polylysine molecule, or a virus like particle (VLP). In a preferred embodiment, the carrier is KLH or CRM197 or a VLP.

Coupling of GIBsPLA2 to a carrier may be performed by covalent chemistry using linking chemical groups or reactions, such as for instance glutaraldehyde, biotin, etc. Preferably, the conjugate or the GIBsPLA2 protein or fragment or mimotope is submitted to treatment with formaldehyde in order to complete inactivation of GIBsPLA2.

In a particular embodiment, the GIBsPLA2 antigen comprises a full length GIBsPLA2 protein, optionally coupled to a carrier protein. In a preferred embodiment, the GIBsPLA2 antigen comprises a protein comprising SEQ ID NO: 2, or a sequence having at least 90% identity to SEQ ID NO: 2, coupled to a carrier protein.

In another particular embodiment, the GIBsPLA2 antigen comprises an immunogenic peptide or mimotope of GIBsPLA2, optionally coupled to a carrier protein. In a more preferred embodiment, the GIBsPLA2 antigen comprises a polypeptide of at least 10 amino acids long comprising at least one of the following amino acid residues of SEQ ID NO: 2 (or of a corresponding sequence of a natural variant of SEQ ID NO: 2): amino acid 70, amino acid 121, amino acid 50, amino acid 52, amino acid 54, amino acid 71, or a combination thereof, optionally coupled to a carrier molecule.

The immunogenicity of the GIBsPLA2 antigen may be tested by various methods, such as by immunization of a non-human animal grafted with human immune cells, followed by verification of the presence of antibodies, or by sandwich ELISA using human or humanized antibodies. The lack of biological activity may be verified by any of the activity tests described in the application. In a preferred embodiment, the GIBsPLA2 antigen has less than 20%, more preferably less than 15%, 10%, 5% or even 1% of the activity of a wild-type GIBsPLA2 protein in an in vitro method of (i) induction of formation of membrane microdomains (MMD) in CD4 T cells or (ii) in rendering CD4 T cells refractory to IL-2 signaling or refractory to IL-7 signaling.

In a particular embodiment, the invention relates to an inactivated and immunogenic GIBsPLA2.

In a further particular embodiment, the invention relates to a GIBsPLA2 protein or a fragment or mimotope thereof conjugated to a carrier molecule, preferably to KLH.

In a further aspect, the invention relates to a vaccine comprising a GIBsPLA2 antigen, a suitable excipient and, optionally, a suitable adjuvant.

Such molecules and conjugates and vaccines represent potent agents for use to immunize subjects, thereby causing a sustained GIBsPLA2 inhibition. Upon repetition, such methods can be used to cause a permanent GIBsPLA2 inhibition.

A further object of the invention relates to of a method for inducing the production of antibodies that neutralize the activity of endogenous GIBsPLA2 in a subject in need thereof, the method comprising administering to said subject a therapeutically effective amount of a GIBsPLA2 antigen or vaccine.

Administration of an antigen or vaccine of the invention may be by any suitable route, such as by injection, preferably intramuscular, subcutaneous, transdermal, intravenous or intraarterial; by nasal, oral, mucosal or rectal administration.

The GIBsPLA2 antigen or vaccine may be used for treating any disease linked to an over-production of GIBsPLA2. More specifically, this invention relates to a method for treating a disease linked to an over-production of GIBsPLA2 in a subject in need thereof, comprising administering to the subject a therapeutically effective amount of a GIBsPLA2 antigen or of a vaccine composition comprising a GIBsPLA2 antigen.

GIBsPLA2 Agonists or Activators

The term GIBsPLA2 "agonist", within the context of the present invention, encompasses any substance having, or mediating or up-regulating GIBsPLA2 activity such as, without limitation, a peptide, a polypeptide, a recombinant protein, a conjugate, a natural or artificial ligand, a degradation product, a homolog, a nucleic acid, DNA, RNA, an aptamer, etc., or a combination thereof. The term "agonist" encompasses both full and partial agonists. A particular example of a GIBsPLA2 agonist is a GIBsPLA2 protein or a nucleic acid encoding a GIBsPLA2 protein.

In a particular embodiment, the invention relates to methods for inhibiting an immune response in a subject, comprising administering to the subject a GIBsPLA2 protein or a nucleic acid encoding a GIBsPLA2 protein.

Compositions

The invention also relates to compositions comprising a GIBsPLA2 modulator or antigen as herein described as an active ingredient, and preferably a pharmaceutically acceptable carrier.

A "pharmaceutical composition" refers to a formulation of a compound of the invention (active ingredient) and a medium generally accepted in the art for the delivery of biologically active compounds to the subject in need thereof. Such a carrier includes all pharmaceutically acceptable carriers, diluents, medium or supports therefore. Conventional pharmaceutical practice may be employed to provide suitable formulations or compositions to subjects, for example in unit dosage form.

The compounds or compositions according to the invention may be formulated in the form of ointment, gel, paste, liquid solutions, suspensions, tablets, gelatin capsules, capsules, suppository, powders, nasal drops, or aerosol, preferably in the form of an injectable solution or suspension. For injections, the compounds are generally packaged in the form of liquid suspensions, which may be injected via syringes or perfusions, for example. In this respect, the compounds are generally dissolved in saline, physiological, isotonic or buffered solutions, compatible with pharmaceutical use and known to the person skilled in the art. Thus, the compositions may contain one or more agents or excipients selected from dispersants, solubilizers, stabilizers, preservatives, etc. Agents or excipients that can be used in liquid and/or injectable formulations are notably methylcellulose, hydroxymethylcellulose, carboxymethylcellulose, polysorbate 80, mannitol, gelatin, lactose, vegetable oils, acacia, etc. The carrier can also be selected for example from methyl-beta-cyclodextrin, a polymer of acrylic acid (such as carbopol), a mixture of polyethylene glycol and polypropylene glycol, monoethanolamine and hydroxymethyl cellulose.

The compositions generally comprise an effective amount of a compound of the invention, e.g., an amount that is effective to modulate GIBsPLA2. Generally, the compositions according to the invention comprise from about 1 µg to 1000 mg of a GIBsPLA2 modulator, such as from 0.001-0.01, 0.01-0.1, 0.05-100, 0.05-10, 0.05-5, 0.05-1, 0.1-100, 0.1-1.0, 0.1-5, 1.0-10, 5-10, 10-20, 20-50, and 50-100 mg, for example between 0.05 and 100 mg, preferably between 0.05 and 5 mg, for example 0.05, 0.1, 0.2, 0.3, 0.4, 0.5, 1, 2, 3, 4 or 5 mg. The dosage may be adjusted by the skilled person depending on the modulator and the disease.

The compositions of the invention can further comprise one or more additional active compounds, for simultaneous or sequential use.

The invention also relates to a method for preparing a pharmaceutical composition, comprising mixing a GIBsPLA2 modulator as previously described and a pharmaceutically acceptable excipient, and formulating the composition in any suitable form or container (syringe, ampoule, flask, bottle, pouch, etc).

The invention also relates to a kit comprising (i) a composition comprising a GIBsPLA2 modulator as previously described, (ii) at least one container, and optionally (iii) written instructions for using the kit.

Diseases

The compounds and compositions of the invention may be used to treat any disease related to an inappropriate (e.g., defective or improper) immune response, particularly to an inappropriate CD4 T cell activity, as well as any disease where an increased immunity may ameliorate the subject condition. These diseases are sometime referred to as "immune disorders" in the present application. This includes immunodefective situations (e.g., caused by viral infection, pathogenic infection, cancer, etc.), autoimmune diseases, grafts, diabetes, inflammatory diseases, cancers, allergies, asthma, psoriasis, urticaria, eczema and the like.

Immunodeficiencies and Associated Disorders

In a first aspect, the invention is based on an inhibition of GIBsPLA2 in a subject, thereby increasing or restoring an immune activity, particularly a CD4-T cell-mediated activity.

In a particular embodiment, the invention is therefore directed to methods for stimulating an immune response in a subject in need thereof, comprising inhibiting GIBsPLA2 in said subject.

In a particular embodiment, the invention is directed to methods for modulating white blood cells in a subject in need thereof, comprising inhibiting GIBsPLA2 in said subject.

Examples of diseases that can benefit from GIBsPLA2 inhibitors are all diseases with an immunodeficiency such as HIV-mediated immunodeficiency. In this regard, in a particular embodiment, the invention is directed to methods for treating an immunodeficiency or an associated disorder in a subject in need thereof, comprising inhibiting GIBsPLA2 in said subject.

In another particular embodiment, the invention is directed to a GIBsPLA2 inhibitor for use for treating an immunodeficiency or an associated disorder in a subject in need thereof.

Immunodeficiencies and associated disorders designate any condition or pathology characterized by and/or caused by a reduced immune function or response in a subject. Immunodeficiencies may be caused by e.g., viral infection (e.g., HIV, hepatitis B, etc.), bacterial infection, cancer, or other pathological conditions. The term "immunodeficiency-associated disorder" therefore designates any disease caused by or associated with an immunodeficiency. The invention is particularly suitable for treating immunodeficiencies related to CD4-T cells, and associated diseases. The present application indeed demonstrates that the biological effects of GIBsPLA2 are involved in CD4 T cell disease state. Accordingly, blocking the activity of GIBsPLA2 has a therapeutic benefit in subjects with altered response to cytokine causing immunodeficiency as often observed in patients infected with HIV.

Accordingly, in a particular embodiment, the invention relates to methods of treating HIV infection in a subject by inhibiting GIBsPLA2 in the subject, preferably by administering a GIBsPLA2 inhibitor or vaccine to the subject. In some embodiments the subject is an early HIV patient and the methods results in increasing the probability that the patient is a HIV controller. In some embodiments the subject is a patient with low immunoreconstitution after antiretroviral treatment and/or with severe idiopathic CD4 T lymphopenia (ICL). The invention also relates to a method for increasing CD4-T cell activity in a HIV-infected subject by inhibiting GIBsPLA2 in the subject, preferably by administering a GIBsPLA2 inhibitor or vaccine to the subject.

In another embodiment, the invention relates to methods of treating acute and/or chronic inflammation and processes derived from inflammatory reactions in a subject by injecting GIBsPLA2 in the subject, either directly or associated with anti-inflammatory drugs.

The invention also provides methods for treating cancer by increasing an immune response in the subject, comprising inhibiting GIBsPLA2 in the subject, preferably by administering a GIBsPLA2 inhibitor or vaccine to the subject. The invention also provides methods of treating CD4 T cell-linked immunodeficiency associated with cancer in a subject by inhibiting GIBsPLA2 in the subject, preferably by administering a GIBsPLA2 inhibitor or vaccine to the subject.

Pathologic Immune Responses and Associated Diseases

The invention may be used to treat any disease related to an inappropriate (e.g., pathologic or improper) immune response or to an undesirable (hyper)activity or (hyper) activation of the immune system, particularly to an inappropriate CD4 T cell activity. These diseases include, for instance, autoimmune diseases, grafts, diabetes, allergies, asthma, psoriasis, urticaria, eczema and the like.

In a further aspect, the invention is thus based on an activation or induction of GIBsPLA2 in a subject, thereby inhibiting an immune activity, particularly a CD4-T cell-mediated activity.

In a particular embodiment, the invention is therefore directed to methods for inhibiting an immune response in a subject in need thereof, comprising inducing or activating GIBsPLA2 in said subject.

In a particular embodiment, the invention is directed to methods for inhibiting white blood cells in a subject in need thereof, comprising inhibiting GIBsPLA2 in said subject.

In another particular embodiment, the invention is directed to methods for treating disorder caused by an undesirable immune response in a subject in need thereof, comprising inducing or activating GIBsPLA2 in said subject.

Inducing or activating GIBsPLA2 in a subject preferably comprises administering to the subject a GIBsPLA2 agonist, for example a GIBsPLA2 protein or a functional fragment thereof.

In another particular embodiment, the invention is directed to a GIBsPLA2 agonist or activator for use for treating a disorder caused by an undesirable immune response in a subject in need thereof.

Examples of diseases that can benefit from G1BsPLA2 agonists are autoimmune disorders, cancers, viral diseases, bacterial infections, etc.

In a particular embodiment, the invention is directed to methods for treating an auto-immune disorder in a subject in need thereof, comprising stimulating or inducing GIBsPLA2 in said subject.

In another particular embodiment, the invention is directed to a compound or a composition of the invention for use in treating an auto-immune disorder in a subject in need thereof.

In a particular embodiment, the invention is directed to methods for treating a cancer in a subject in need thereof, comprising stimulating or inducing GIBsPLA2 in said subject.

In another particular embodiment, the invention is directed to a compound or a composition of the invention for use in treating cancer in a subject in need thereof.

Another particular embodiment of the invention relates to a method for treating (e.g., reducing or preventing or inhibiting) graft rejection, or for treating graft vs host disease in a transplanted subject, comprising stimulating or inducing GIBsPLA2 in said subject. A further object of the invention is a method for improving allogeneic graft tolerance in a subject comprising stimulating or inducing GIBsPLA2 in said subject.

Anti-Microbial Activity

The present application also provides, in a further aspect, a method for killing microbes using GIBsPLA2. By acting directly on the membranes, GIBsPLA2 can destroy or kill bacteria, enveloped viruses, parasites and the like.

In acute infections or in infections, GIBsPLA2 may be used either alone or associated with antibiotics, anti-viral, anti-retroviral and anti-parasite drugs. In the case of microbes resistant to known anti-microbial drugs, GIBsPLA2 may represent an alternative therapy. It can be used in very short term treatment, e.g., in very dangerous and acute clinical situations.

Specific examples of diseases that can benefit from treatment by G1BsPLA2 according to the invention are all the clinical situations with an hyper activity of the immune system or a chronic inflammation such as Multiple sclerosis, Myasthenia gravis, Autoimmune neuropathies such as Guillain-Barré, Autoimmune uveitis, Uveitis, Autoimmune hemolytic anemia, Pernicious anemia, Autoimmune thrombocytopenia, Temporal arteritis, Anti-phospholipid syndrome, Vasculitides such as Wegener's granulomatosis, Behcet's disease, Atherosclerosis, Psoriasis, Dermatitis herpetiformis, Pemphigus vulgaris, Vitiligo, Pemphigus Vulgaris, Mycosis Fungoides, Allergic Contact Dermatitis, Atopic Dermatitis, Lichen Planus, PLEVA, eczema, Crohn's Disease, Ulcerative colitis, Primary biliary cirrhosis, Autoimmune hepatitis, Type 1 diabetes mellitus, Addison's Disease, Grave's Disease, Hashimoto's thyroiditis, Autoimmune oophoritis and orchitis, Autoimmune Thyroiditis, Rheumatoid arthritis, Systemic lupus erythematosus, Scleroderma, Polymyositis, Dermatomyositis, Spondyloarthropathies such as ankylosing spondylitis, or Sjogren's Syndrome.

The duration, dosages and frequency of administering compounds or compositions of the invention may be adapted according to the subject and disease. The treatment may be used alone or in combination with other active ingredients, either simultaneously or separately or sequentially.

The compounds or compositions according to the invention may be administered in various ways or routes such as, without limitation, by systemic injection, intramuscular, intravenous, intraperitoneal, cutaneous, subcutaneous, dermic, transdermic, intrathecal, ocular (for example corneal) or rectal way, or by a topic administration on an inflammation site, and preferably by intramuscular or intravenous injection.

A typical regimen comprises a single or repeated administration of an effective amount of a GIBsPLA2 modulator over a period of one or several days, up to one year, and including between one week and about six months. It is understood that the dosage of a pharmaceutical compound or composition of the invention administered in vivo will be dependent upon the age, health, sex, and weight of the recipient (subject), kind of concurrent treatment, if any, frequency of treatment, and the nature of the pharmaceutical effect desired. The ranges of effectives doses provided herein are not intended to be limiting and represent preferred dose ranges. However, the most preferred dosage will be tailored to the individual subject, as is understood and determinable by one skilled in the relevant arts (see, e.g., Berkowet et al., eds., The Merck Manual, 16$^{th}$ edition, Merck and Co., Rahway, N.J., 1992; Goodmanetna., eds., Goodman and Cilman's The pharmacological Basis of Therapeutics, 10$^{th}$ edition, Pergamon Press, Inc., Elmsford, N.Y., (2001)).

Diagnosis

The invention also provides methods for detecting an immune defect in a subject based on a detection of the presence or amount or absence of GIBsPLA2 in a sample from a subject. The method of the invention may be carried out using a variety of detection technologies or platforms known per se in the art such as, without limitation Capture assay, Sandwich assay, Competition assay, Radio-immuno assays, Enzyme labels with substrates that generate colored, fluorescent, chemiluminescent, or electrochemically-active products, Fluorescence, fluorescent polarization, Chemiluminescence, Optical and colorimetric, Electrochemiluminescence, Time-resolved fluorescence, Surface plasmon resonance, Evanescent wave, Multiwell plate (ELISA), Individual assay, Multiplex assay, Latex bead—multiplex assay, Microarray (Laminar surface)—multiplex assay, Glass, Plate based assays or Strip based assays.

In a particular embodiment, the method comprises determining the presence, or amount, or absence of a polymorphism in the GIBsPLA2 gene, RNA or protein. Our results show that GIBsPLA2 is subject to high polymorphism and that this correlates to the physiological status of subjects. The invention thus comprises (i) determining the presence, or amount, or absence of a particular polymorphic isoform of GIBsPLA2, and/or (ii) determining the global rate of polymorphism of GIBsPLA2 in a subject, said data being correlated to the physiological status of the subject. In particular, specific isoforms may be characteristic of the predisposition, presence or onset in a subject of a disorder as described above. Such determination may also be used in personalized medicine, to adjust treatment.

Methods of Monitoring and/or Diagnosing Immunodeficiency Associated with CD4 T Cell Defects Comprising Detecting GIBsPLA2

Methods of monitoring and/or diagnosing immunodeficiency associated to CD4 T cell defects in particular in human immunodeficiency virus (HIV) infection in a subject, are provided by this disclosure. In some embodiments the methods comprise (a) providing a sample containing a body fluid, preferably plasma from a subject, and (b) detecting a level of GIBsPLA2 in the sample above a threshold. The presence of GIBsPLA2 in the sample may be detected by any method known in the art, such as for example by a method comprising an enzymatic assay, a ligand-capture assay and/or an immunoassay.

In some embodiments the method comprises obtaining a sample comprising plasma from a subject and determining whether the plasma has at least one activity selected from inducing formation of abnormal membrane microdomains (MMD) in CD4 T cells from healthy subjects and rendering CD4 T cells of healthy subject refractory to interleukin-7 (IL-7) signaling. If the plasma from the subject comprises such an activity then the subject is in some embodiments determined to have a CD4 T cell-linked immunodeficiency as often observed in HIV-infected patients but not only. If the plasma fraction does not comprise such an activity then the subject is in some embodiments determined to have low exposure to immunodeficiency associated to the alteration of T CD4 cells to cytokine-regulated homeostasis.

In some embodiments the subject is determined to have an HIV infection. In contrast, if the protein fraction does not comprise such an activity then the subject is in some embodiments determined to not have an immunodeficiency associated to CD4 T cell defects as disclosed herein. In some embodiments the subject is determined to not have an HIV infection.

In some embodiments the methods comprise contacting the sample comprising a body fluid, preferably plasma, from the subject with an antibody specific for GIBsPLA2 and determining the presence or absence of an immunological reaction. In some embodiments the presence or absence of an immunological reaction is determined by a method comprising an enzyme-linked immunosorbent assay (ELISA). The presence of an immunological reaction between the antibody specific for GIBsPLA2 and the sample indicates the presence of GIBsPLA2 in the sample, which in turn indicates that the subject has an immunodeficiency associated to CD4 T cell defects. In some embodiments the subject is determined to have an HIV infection. In contrast, the absence of an immunological reaction between the antibody specific for GIBsPLA2 and the sample indicates that the subject does not have an immunodeficiency associated to CD4 T cell defects as disclosed herein. In some embodiments the subject is determined to not have an HIV infection.

In some embodiments the assay for the presence of GIBsPLA2 in the sample is qualitative. In some embodiments the assay for the presence of GIBsPLA2 in the sample is quantitative.

In some embodiments the methods comprise comparing the results of the assay to the results of a similar assay of a control sample comprising plasma of a subject who does not have an immunodeficiency associated to CD4 T cell defects. In some embodiments the methods comprise comparing the results of the assay to the results of a similar assay of a sample comprising plasma of the same subject harvested earlier.

Methods of Monitoring and/or Diagnosing Immunodeficiency Associated with CD4 T Cell Alteration Comprising Characterizing Membrane Microdomains on CD4 T Cells The data in the examples demonstrate that HIV-infected patients present formation of distinctive membrane microdomains (MMD) on the surface of CD4 T cells although very few cells are really infected by HIV. Accordingly, this disclosure also provides methods for diagnosing immunodeficiency associated with CD4 T cell alteration, such as for example immunodeficiency caused by human immunodeficiency virus (HIV) infection in a subject. In some embodiments the methods comprise: (a) isolating CD4 T lymphocytes from a subject, and (b) measuring the number and/or size of membrane microdomains (MMD) on the T-cells. In some embodiments the methods further comprise at least one of (c) measuring the amount of phospho-STAT5 in the T-cells and (d) assaying the nuclear import fraction of phospho-STAT5 in the T-cells. In some embodiments the number and/or size of MMD on the T-cells is measured in the absence of interleukin. In some embodiments the number and/or size of MMD on the T-cells is measured in the absence of IL-2. In some embodiments the number and/or size of MMD on the T-cells is measured in the absence of IL-7. In some embodiments the number and/or size of MMD on the T-cells is measured in the presence of a subthreshold level of interleukin.

In some embodiments if the number of MMD on the T cells isolated from the subject is at least a threshold that indicates that the subject has immunodeficiency associated with CD4 T cell alteration. In some embodiments it indicates that the subject has an HIV infection. In some embodiments if the number of MMD on the T cells isolated from the subject is not at least a threshold that indicates that the subject does not have immunodeficiency associated with CD4 T cell alteration as disclosed herein. In some embodiments it means that the subject does not have an impaired CD-4 T cell response to cytokine signaling. In some embodiments it means that the subject does not have an impaired CD-4 T cell response to interleukin-7. In some embodiments it indicates that the subject does not have an HIV infection. In some embodiments the threshold is at least about 80 per cell, at least about 90 per cell, at least about 100 per cell, at least about 110 per cell, or at least about 120 per cell. In a non-limiting preferred embodiment, the threshold is at about 100 per cell. In some embodiments if the MMD on the T cells isolated from the subject have a diameter of at least a threshold that indicates that the subject has an HIV infection. In some embodiments if the MMD on the T cells isolated from the subject do not have diameter of at least a threshold that indicates that the subject does not have an impaired response to interleukin-7 and more generally to cytokines. In some embodiments it indicates that the subject does not have an HIV infection. In some embodiments the threshold is a diameter of at least 100 nm, at least 110 nm, at least 120 nm, at least 130 nm, or at least 140 nm. In a non-limiting preferred embodiment, the threshold is a diameter of at least about 120 nm.

Because RIF may alter the responsiveness of CD4 T cells to IL-7 by aggregating membrane receptors in abnormally large MMD, responses to other gamma-c and cytokines may be affected as well and RIF might be also associated to other pathologies involving altered CD4 T cell response.

Methods of Identifying Candidate Therapeutic Agents

This invention also provides methods for identifying a candidate therapeutic agent, comprising: (a) contacting CD4 T lymphocytes with GIBsPLA2 in the presence of an agent, and (b) measuring GIBsPLA2-induced CD4 T cell activation. In some embodiments the methods comprise (c) comparing the level of GIBsPLA2-induced CD4 T cell activation in the presence of the agent with the level of GIBsPLA2-induced CD4 T cell activation in the absence of the agent. In some embodiments, if the level of GIBsPLA2-induced CD4 T cell activation in the presence of the agent is lower than the level of GIBsPLA2-induced CD4 T cell activation in the absence of the agent, then the agent is identified as a candidate immunodeficiency therapeutic agent. In some embodiments the agent is identified as a candidate HIV therapeutic agent. In some embodiments, if the level of GIBsPLA2-induced CD4 T cell activation in the presence of the agent is higher than the level of GIBsPLA2-induced CD4 T cell activation in the absence of the agent then the agent is identified as a candidate immunosuppressive therapeutic agent.

In some embodiments, measuring GIBsPLA2-induced CD4 T cell activation comprises determining the number of MMD per CD4 T cell.

In some embodiments, measuring GIBsPLA2-induced CD4 T cell activation comprises determining the mean diameter of MMD on CD4 T cells.

In some embodiments, measuring GIBsPLA2-induced CD4 T cell activation comprises determining the IL-7 responsiveness of CD4 T cells assayed by STAT5 phosphorylation and/or nuclear import.

As used herein an "agent" may be any chemical entity under evaluation as a potential therapeutic. In some embodiments the agent is an organic molecule. In some embodiments the agent comprises from 2 to 100 carbon atoms, such as from 2 to 50 carbon atoms, 5 to 50 carbon atoms, or 10 to 50 carbon atoms. In some embodiments the agent is a peptide, a protein, a glyco-protein, or a lipoprotein. In some embodiments the agent is an antibody.

In some embodiments the agent has not been previously determined to have a biological activity implying an utility as a therapeutic agent for treatment of immunodeficiency, such as that often associated with HIV infection. In some embodiments the agent has been previously determined to have a biological activity implying an utility as a therapeutic agent for treatment of immunodeficiency such as that often associated with HIV infection.

As used herein, a "candidate immunodeficiency therapeutic agent" or a "candidate HIV therapeutic agent" is an agent that inhibits the ability of RIF to activate CD4 T cells in at least one assay. Consistent with the data reported herein, the ability of an agent to inhibit the ability of GIBsPLA2 to activate CD4 T cells in at least one assay is a useful way to identify agents that are likely to be therapeutically useful for treating immunodeficiencies including immunodeficiencies associated with HIV infections. Accordingly, it is also a useful way to identify agents that are likely to be therapeutically useful for treating HIV infection. Of course, as with all therapeutic molecules further characterization will be required. However, this does not detract from the utility of candidate HIV therapeutic agents of this disclosure.

Further aspects and advantages of the invention are disclosed in the following experimental section, which shall be considered as illustrative.

EXAMPLES

1. Materials and Methods 1.1. Patients

VP included in the study had been HIV-positive for more than one year. They had never received any antiretroviral drugs and had a viral load >10,000 RNA copies/ml with a CD4 count >200/µl at the time of blood collection (ANRS EP 33 and EP20 studies). All blood samples from VP were drawn at the Centre Hospitalier de Gonesse. Blood from HD was provided by the Etablissement Français du Sang (Centre Necker-Cabanel, Paris). Plasma samples from ART patients were drawn from individuals who had been receiving treatment for at least one year. Their viral load had been undetectable for at least 6 months and their CD4 counts >500/µl at the time of blood collection. Plasma samples from HIC patients were drawn from individuals with an undetectable viral load 10 years after infection. Plasma samples were collected at Centre d'Infectiologie Necker-Pasteur.

1.2. Analysis of Membrane Microdomains (MMD), Receptor Diffusion Rates and Phospho-STAT5 Cellular Compartmentalization in Purified CD4 T Lymphocytes CD4 T-cells were purified by negative selection as already described (10) then activated with 2 nM recombinant glycosylated human IL-7 (Cytheris) or 40 µg PHA (Sigma). The confocal and STED microscopy used to study cell surface microdomains (MMD) and phospho-STAT5 cellular compartment distribution has already been described (10, 12). FCS analysis of protein diffusion at the surface of living cells has also been described (10, 12

1.3. Preparation and Analysis of Detergent-Resistant Microdomains (DRM)

The preparation of Triton-X100 lysates of CD4 T lymphocytes from HD or VP, followed by centrifugation through sucrose gradients and Western blot analysis of the fractions collected, has been previously described (12). mAb specific for flotillin, IL-7Ralpha and gamma c were used to detect the corresponding bands by Western blots (12).

1.4. Characterization of RIF from VP Plasma 1.4.1. Bioassays

The MMD induction assay was as follows: VP plasma (5 or 10%) was first incubated (20 min) in medium with purified HD CD4 T cells. The cells were then plated on polylysine-coated glass slides for 10 min then activated by 15 min IL-7 (2 nM) or not for control (NS), then fixed by PFA (PFA, 1.5%, 15 min at 37° C. followed by 15 min at room temperature) equilibrated one hour in PBS/SVF 5% before being stained by cholera toxin B (CtxB-AF488). MMD were counted by STED microscopy.

The assay for inhibition of STAT phosphorylation and nuclear translocation was as follows: VP plasma (5 or 10%) was first incubated with purified HD CD4 T cells (20 min) before stimulation by IL-7 (2 nM, 15 min.). Cells were then plated on polylysine-coated glass slides for 10 min then activated by 15 min IL-7 (2 nM) or not for control (NS), then fixed by PFA (PFA, 1.5%, 15 min at 37° C. followed by 15 min at room temperature) and permeabilization by methanol (90% at −20° C.). Cells were equilibrated one hour in PBS/SVF 5% then phospho-STAT5 was then stained by rabbit anti-STAT5 labelled with goat anti-rabbit-Atto642 and analyzed by FACS or STED microscopy.

1.4.2. Enzyme Treatments

The effects of enzyme digestion on RIF activity were evaluated by treating VP plasma filtered on a 30 kDa membrane. Plasma compounds with MW<10 kDa were used as negative controls. Effects of porcine trypsin (1 U/ml for 30 min at 37° C., followed by PMSF inhibition and buffer exchange with Millipore 5 kDa-membrane centrifugal filters), or DNAse I (1 U/ml for 30 min at 37° C.), or RNAse (1 U/ml for 30 min at 37° C.) or Peptide N-glycanase (1 U/ml for 30 min at 37° C.) were tested. All preparations were analyzed at 10% final concentration.

1.4.3. MW Determination or RIF Purification

Size exclusion chromatography was performed by loading 1.6 ml of plasma onto a 85-ml Sephadex G100 column pre-equilibrated with ammonium carbonate (0.1M) or PBS, then collecting 0.8 ml fractions of the eluate. The column was calibrated using a protein set (GE-Healthcare). Protein concentration was measured by the Bradford method. VP plasma previously filtered on a 100 kDa membrane and total VP plasma were tested and gave identical results. Fractions between 13-17 kDa were collected, which contain semi-purifed RIF.

1.4.4 Isoelectric Point Determination

Anion or cation exchange chromatography was performed on MonoQ or MonoS 1ml columns (GE-Healthcare) with elution by successive pH steps (ammonium carbonate/ammonium acetate buffers). The pH of each eluated fraction was measured and these were then adjusted to pH 7.4 before testing of their biological effects. RIF activity was measured in the corresponding fractions immediately after elution.

1.4.5 MS Analysis

Samples from gel filtration (G100) were lyophilized then resuspended, pooled and proteolysed with porcine trypsin, according to methods known per se in the art. Proteolytic peptides were then separated in 12 fractions by chromatography through C18 column eluted in ammonium acetate. The 12 fractions were separated through C18 eluted in reverse phase (acetonitrile) and directly injected by electrospray in an orbitrap Velos (Thermo Scientific) for MS analysis with secondary Ar-fragmentation then MS/MS for the 10 higher-intensity peaks per MS scan.

Standard Mascot and X-Tandem programs were used. For each protein of database subsets, 3 criteria were computed:
i-score: Computation of theoretical specificity of every peptides from trypsin digestion of a single protein in the NextProt database enriched with mature proteins with signal peptide cleavage (number of unique peptides/protein): number of specific peptides overall human sequences (all), sequences with a N-term signal peptide (sec) per protein Computation of the theoretical occurrence of peptides compatible with peaks from all MS scan series (theoretical peptide matching peaks/protein)

Computation of the theoretical coverage of protein sequence with peak-matching peptides For each protein ap score was determined as a computation of all three scores.

Example 1: Aberrant Activation of CD4 T Lymphocytes from VP as Measured by the Presence of Abnormal Membrane Microdomains (MMD)

This example describes the investigation of new molecular and cellular parameters that explain some of the abnormal responses seen in the CD4 T lymphocytes of chronically HIV-infected patients. Chronic activation of the immune system is usually measured by assessing the over expression of cell surface molecules such as CD38, HLA-DR and CD25 that are considered as the main markers of CD4 dysfunction (15). However, despite many efforts, these data have remained blurred, and the phenotype of the CD4 T cells cannot directly explain their immune defects.

STED microscopy and labeling with cholera toxin B (CtxB-AF488) were used to detect the presence of MMD (12). Before any stimulation, the surface of CD4 T lymphocytes purified from VP was found to bear far more MMD than quiescent CD4 T lymphocytes purified from HD (FIG. 1a). And most importantly, all the CD4 T cells from VP showed increased numbers of MMD. This abnormal pattern was not the consequence of stimulation by IL-7 in VP plasma since average IL-7 concentrations in this plasma (0.4 pM) were only 100th the Kd of the IL-7R (13, 14). When purified CD4 T cells from HD were stimulated by IL-7, large numbers of MMD were observed. By contrast, the MMD pattern of CD4 T cells from VP was unaffected by IL-7 (FIG. 1a). This abnormal activation coupled with the absence of any response to IL-7 can be mimicked by a non physiological stimulus such as with phytohemagglutinin (PHA) (FIG. 1a).

These various abnormal MMD were then counted. Around 150-200 MMD were observed per CD4 T cell from VP, as with PHA-stimulated HD CD4 T cells (FIG. 1c). Here again, the results obtained showed that all CD4 T cells from VP expressed MMD, including all the major CD4 subpopulations (FIG. 1c). IL-7 failed to increase MMD numbers in VP. By contrast, MMD numbers in HD CD4 T cells increased from a background level of around 10 MMD/cell to 300 after IL-7 stimulation. A study of MMD size was also conducted (FIGS. 1d and e). This showed that the MMD on CD4 T cells from VP and on PHA-stimulated HD CD4 T cells were far larger (250 nm) than those from HD CD4 T cells stimulated by IL-7 (90 nm).

Example 2: All IL-7R Alpha and Gamma-c Chains are Sequestered in Abnormal Detergent-Resistant Membrane Microdomains (DRM) Isolated from VP CD4 T Cells Resting HD CD4 T cells were analyzed to verify that IL-7R alpha and gamma-c chains are located in high-density fractions outside MMD. When these HD CD4 T cells are stimulated by IL-7, these two chains are located in low-density fractions corresponding to detergent-resistant MMD or DRM containing all the proteins sequestered in MMD (FIG. 2).

Figure 2:
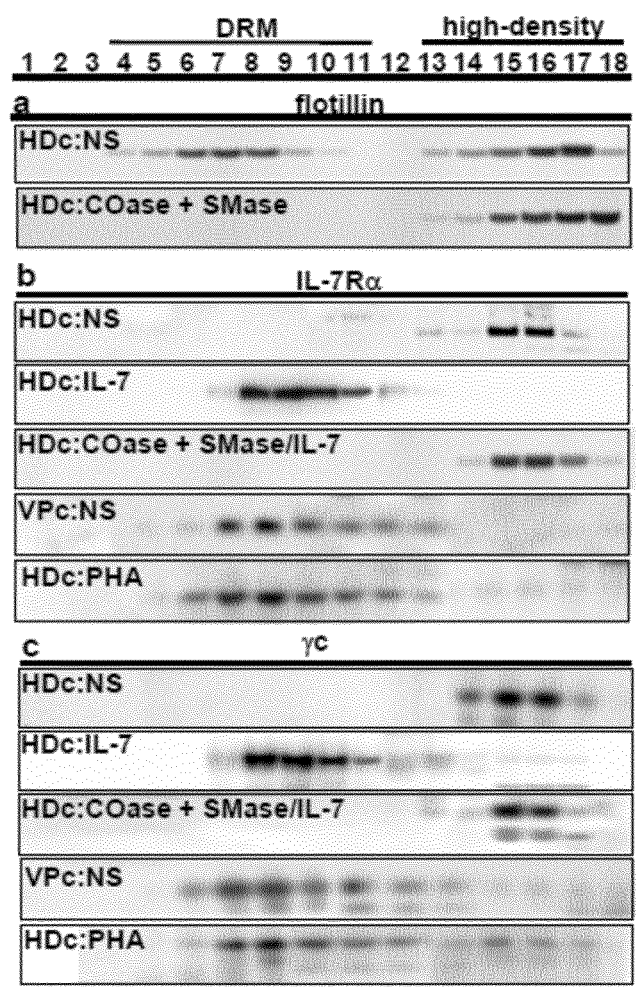

When the study was repeated on CD4 T cells purified from VP, the pattern was different (FIG. 2). Before any stimulation, all the IL-7R alpha and gamma-c chains were already sequestered in DRM; none were located in the high-density fractions corresponding to free receptors outside the MMD. Furthermore, pre-stimulation of the CD4 T cells by IL-7, before DRM preparation, did not affect this pattern (data not shown). Here again, pre-stimulation of HD CD4 T cells by non physiological PHA reproduced this pathological situation. This confirms the data in FIG. 1 and demonstrates that the CD4 T cells in VP are subject to aberrant activation prior to any stimulation. In addition, these abnormal MMD contain all the IL-7R chains (FIG. 2).

Example 3: 2D Gel Analysis of the IL-7 Signalosome in Purified CD4 T Cells from HD, VP and IL-7-Stimulated HD Cells. Characterization of the Aberrant State of Activation by the Protein Pattern Recovered after Immunoprecipitation 2D-electrophoresis was used to demonstrate that the composition of the IL-7 signalosome in VP was abnormal and different from that in quiescent and IL-7-activated HD CD4 T cells (FIGS. 7a, 7b and 7c).

Proteins were immunoprecipitated with anti-IL-7Ralpha (mouse mAb 40131, R&D System) immobilized on protein G-Sepharose 4G from purified CD4 T-cell lysate and separated on 2D-PAGE (IEF on pH 3-10 gel stripes followed by SDS-gel with 12% acrylamide-bis). pH and MW (kDa) scales are displayed. Gels were stained with Sypro-Ruby. The gels shown are representative of 8 NS/IL-7 pairs obtained from HD and 3 gels from VP.

(FIG. 7a) non-stimulated (NS) HD CD4 T-cells.

(FIG. 7b) VP CD4 T-cells. More spots were observed in Sypro Ruby-stained 2D-gels prepared from VP than from HD. In addition we observed that common spots were more intense when 2D-gels were prepared with VP extracts.

(FIG. 7c) IL-7-stimulated HD CD4 T-cells. The pattern in HD CD4 T cells stimulated by IL-7 differs from that in VP CD4 T cells. This further supports the proposal that the aberrant activation found in VP is not the consequence of IL-7 stimulation that could take place in organs with high levels of IL-7, for example in IL-7-producing organs.

It may be concluded from this analysis that IL-7R chains in VP CD4 T cells are not only part of abnormal MMD but also that they interact with protein complexes different from those found in the normal IL-7 signalosome.

Figure 8:
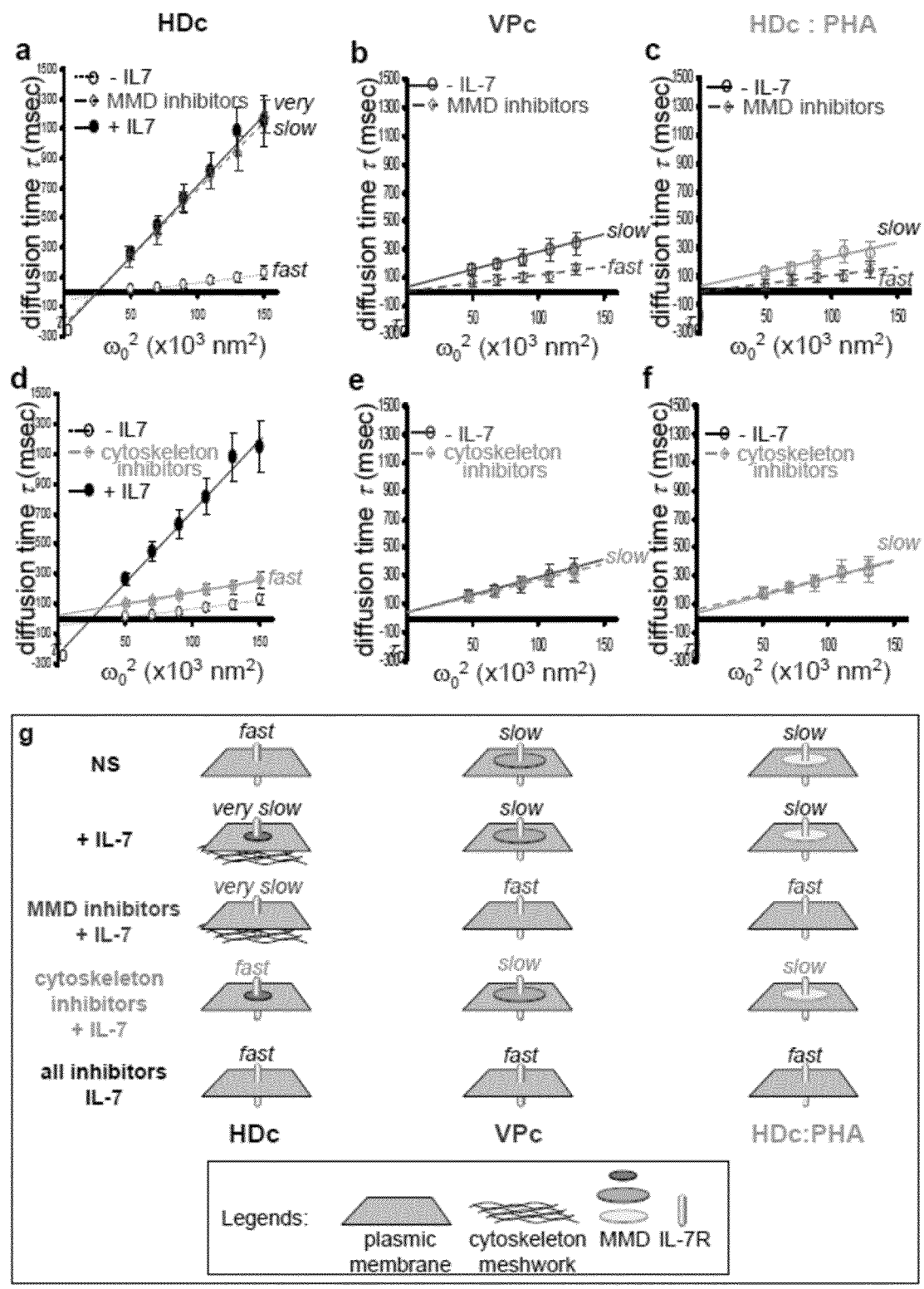
Figure 9:
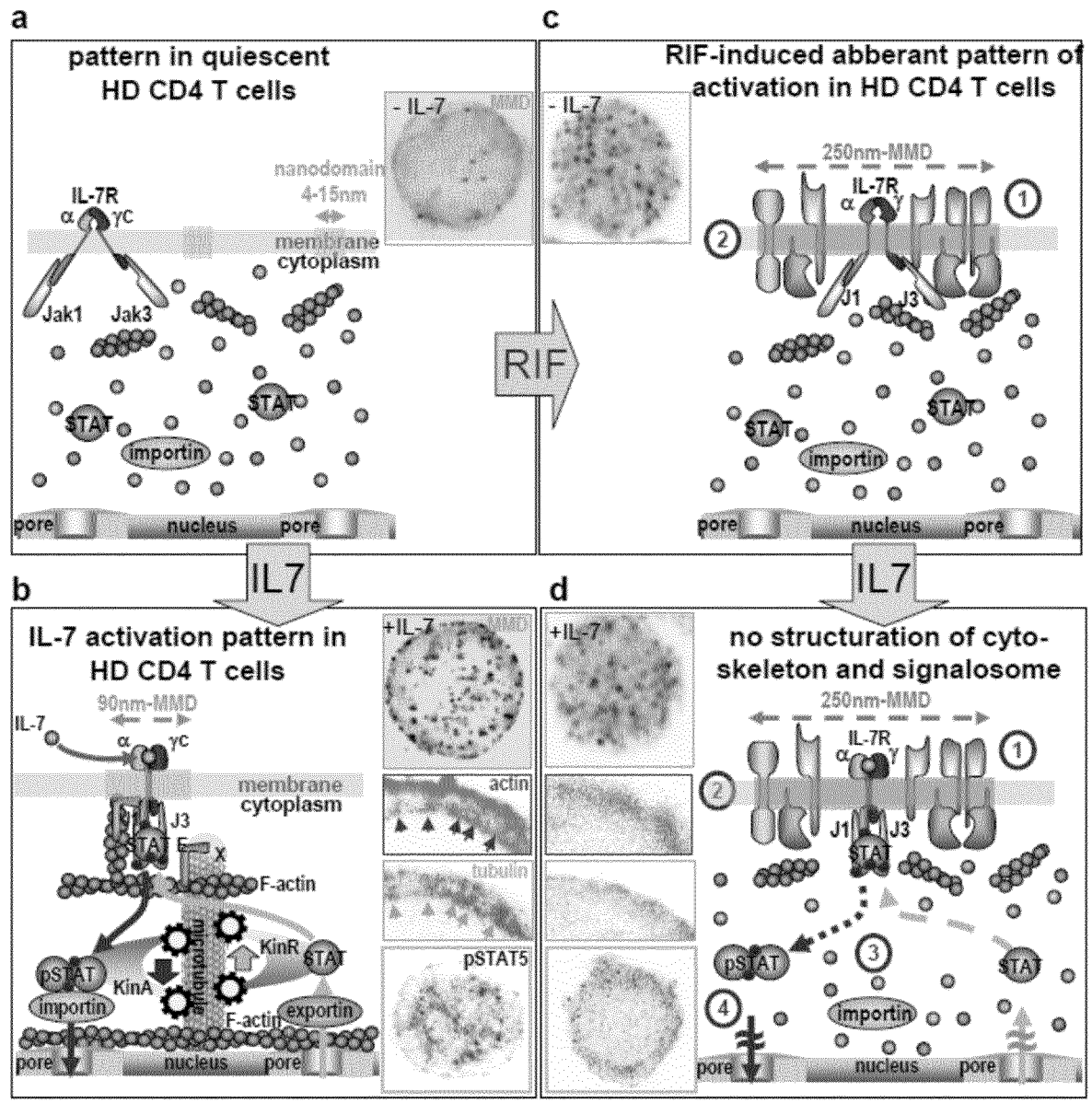

Example 4: Diffusion Rate of IL-7Ralpha at the Surface of Purified CD4 T Cells from HD, VP and PHA-Stimulated HD Cells. IL-7Ralpha in VP CD4 T Cells is Embedded in Lipid-Rich Abnormal MMD, Thus Limiting its Diffusion Rates and Precluding any Interactions with the Cytoskeleton and Therefore any Ability to Transmit Signals The two-dimensional diffusion of IL-7Ralpha stained with AF488-anti-IL-7Ralpha mAb was measured by FCS at the surface of living CD4 T-cells. The results are shown in FIG. 8. Diffusion times $\tau D$ (in $10^{-3}$ sec) were measured in the absence of IL-7 (○, autocorrelation) or in the presence of IL-7-biotin•SAF633 (●, crosscorrelation) as described (10, 12). These times were then plotted versus cell surface area $\omega_0^2$ (in $10^3$ nm$^2$) intercepted by the confocal volume. The diffusion plots are shown with and without pre-treatment with MMD inhibitors (COase 1 µg/ml plus SMase 0.1 µg/ml for 30 min) or cytoskeleton inhibitors (CytD 20 µM plus Col 10 µM for 30 min).

Bars indicate SEM from 5 independent experiments. Slopes of the linear regression give effective diffusion rates $D_{eff}$ and y-intercepts extrapolate confinement time TO as we described previously (12). $D_{eff}$ are shown in the bar graph FIG. 3a.

(FIGS. 8a, 8d) at the surface of HD CD4 T-cells,
(FIGS. 8b, 8e) at the surface of VP CD4 T cells,
(FIGS. 8c, 8f) at the surface of HD CD4 T cells pre-activated with PHA (1 µg/ml).

(FIG. 8g) Scheme of the mechanism of IL-7Ralpha diffusion embedded in MMD before and after treatment by MMD inhibitors or cytoskeleton inhibitors. MMD are indicated by disks, receptors by rods, cytoskeleton is shown as a net. Diffusion rates (fast, slow, very slow) are indicated to facilitate data interpretation. This scheme illustrates the results also reported in FIG. 3a.

Figure 3:
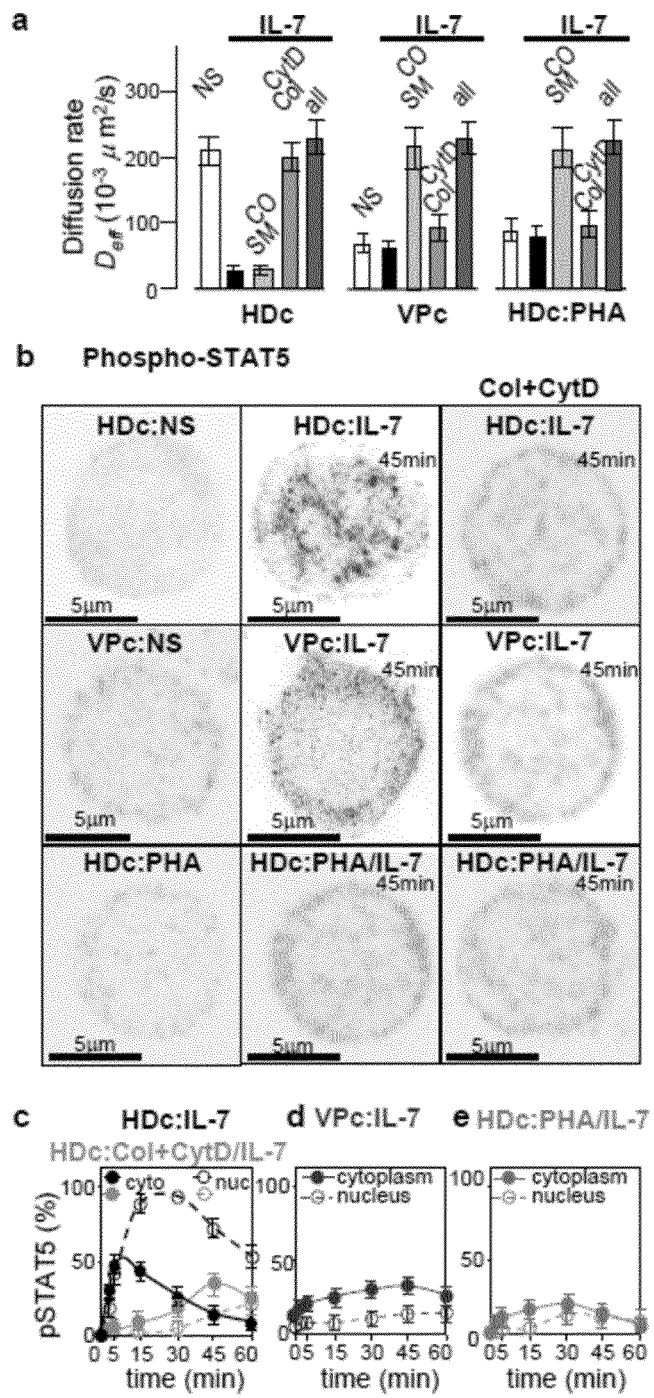

Example 5: IL-7R Chains Sequestered in the Abnormal MMD of VP CD4 T Cells are Non Functional IL-7R alpha diffusion rates were measured at the surface of CD4 T cells as previously described (10, 12) and as detailed in Example 4. Before any stimulation, these diffusion rates were seen to be three times slower on VP than HD CD4 T cells (FIG. 3a). This further demonstrates that IL-7R alpha chains are embedded in abnormal MMD at the surface of these CD4 T cells (FIG. 3a). COase plus SMase treatment released the receptor from its MMD constraints and therefore increased its diffusion rate (FIG. 3a). By contrast, treatment with cytochalasin D (Cyt D) plus colchicine (Col)—which disorganizes the cytoskeleton—had no effect on the diffusion rate of the IL-7R alpha chain in VP CD4 T cells (FIG. 3a). Since cytoskeleton organization is an absolute necessity for signal transduction, this absence of any functional or structural link between IL-7R alpha and the cytoskeleton meshwork suggests that signaling cannot proceed when IL-7R complexes are sequestered in abnormal MMD, as is the case in VP CD4 T cells.

Pulsed-STED microscopy was then used to study STAT5 phosphorylation (phospho-STAT5) and phospho-STAT5 partition in the cytoplasm and nucleus of both HD and VP CD4 T cells. FIG. 3b shows STED images of phospho-STAT5 distribution before and after 15 min of IL-7 stimulation. We noted that phospho-STAT5 accumulated in the nucleus of HD CD4 T cells, and this phenomenon was inhibited by cytoskeleton disorganization. By contrast, no phospho-STAT5 translocation to the nucleus occurred in VP CD4 T cells or in PHA pre-stimulated HD CD4 T cells (FIG. 3b).

The kinetics of phospho-STAT5 appearance in the cytoplasm and nucleus was then followed for one hour (FIGS. 3c, d, e). This showed that phospho-STAT5 in VP CD4 T cells mostly accumulated in the cytoplasm and did not migrate to the nucleus (FIG. 3d), as in PHA-stimulated HD CD4 T cells (FIG. 3e). This was particularly clear when the results were compared with those obtained in the five minutes following IL-7 stimulation of HD CD4 T cells where 50% of phospho-STAT5 was found in the nucleus (FIG. 3c).

Figure 4:
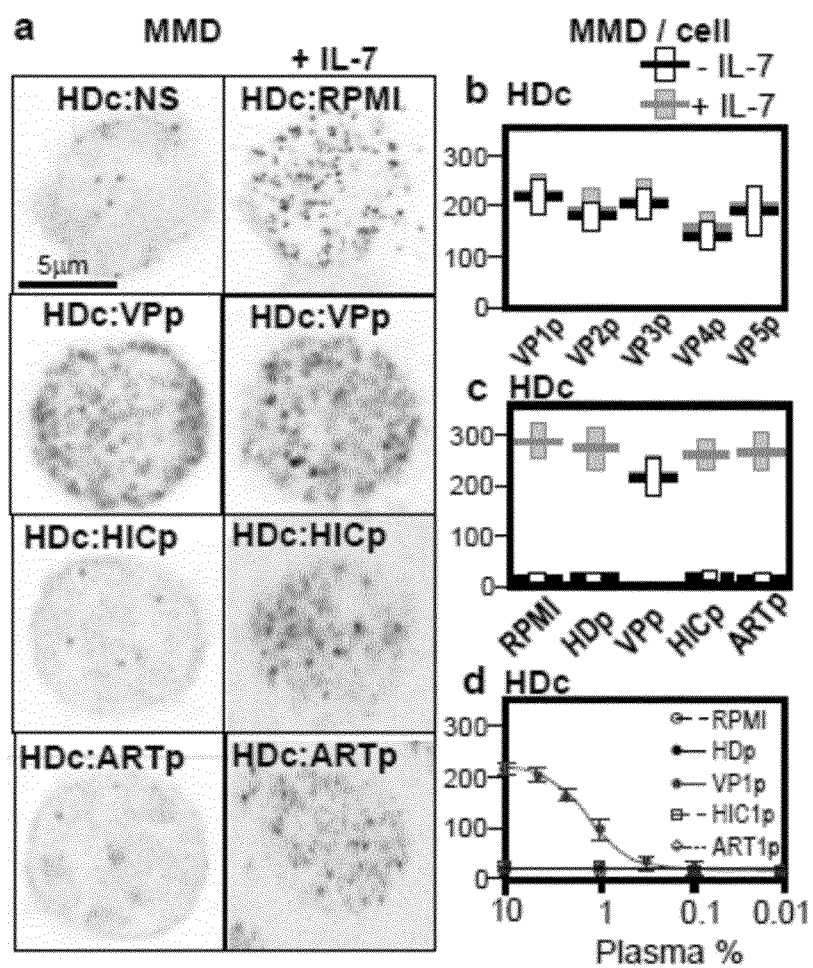

Example 6: Plasma from VP Induces Abnormal MMD at the Surface of Purified HD CD4 T Cells The origin of the aberrant activation of VP CD4 T cells was then investigated. The fact that all the CD4 T cells were involved and that a non physiological signal such as PHA mimics the results led to an investigation of the plasma of VP. Purified HD CD4 T cells were incubated with 10% VP plasma for 30 min and MMD counted at the surface of the CD4 T cells as detected by labeled cholera toxin B (CtxB-AF488). FIG. 4a shows the images obtained. VP plasma alone induced large numbers of MMD on HD CD4 T cells. Adding IL-7 did not affect the size or number of these MMD (FIG. 4a). These results are shown for plasma from five different VP (FIG. 4b) and were verified using many more plasma samples from these VP (>15). The experiments were also repeated using CD4 T cells from different HD (>5). Controls consisted of testing plasma samples from HIV-controllers (HIC) and antiretroviral-treated (ART) patients on purified HD CD4 T cells. None of these induced MMD or inhibited the IL-7 induction of MMD (FIG. 4c).

This was further verified by testing a large number of dilutions of the various plasmas (FIG. 4d). VP plasma down to a 0.1% dilution resulted in the formation of MMD scattered across the cell surface. VP plasma diluted 50 to 100 fold gave 50% maximum activity. None of the plasma samples from HIC or ART patients induced MMD at any dilution.

Figure 5:
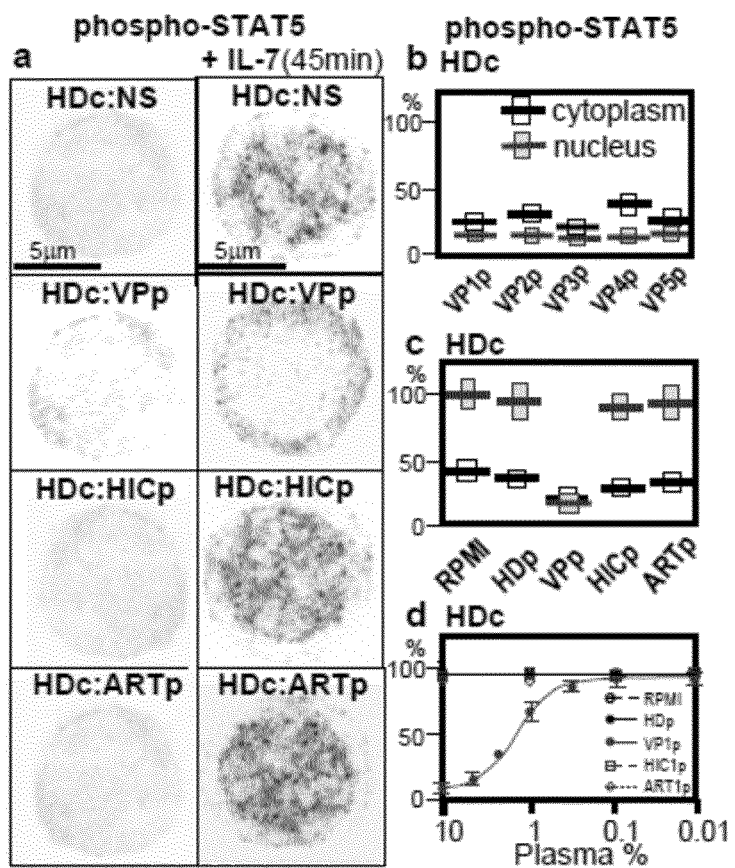
Figure 6:
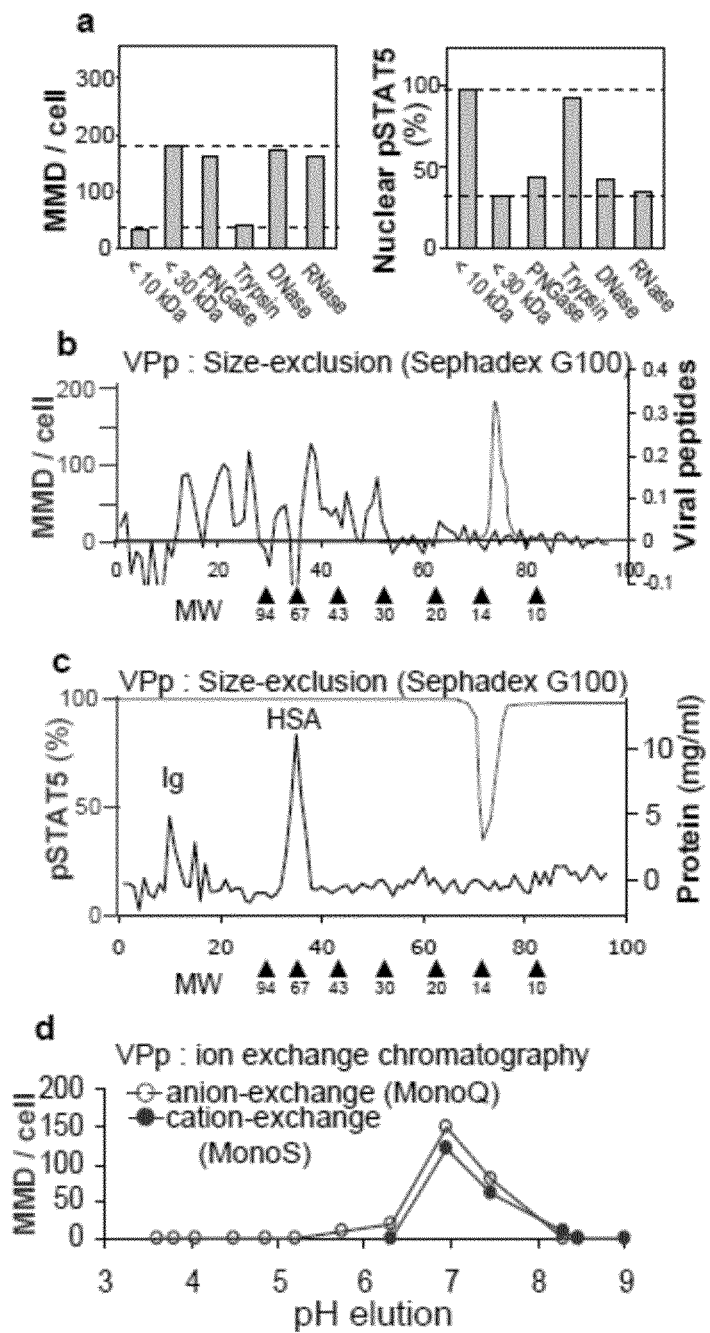

Example 7: Plasma from VP Inhibits IL-7-Induced Phospho-STAT5 Nuclear Translocation The function of the IL-7R in HD CD4 T cells treated with VP plasma was tested by following STAT5 phosphorylation and nuclear translocation. As seen in FIG. 5a, pre-incubation of HD CD4 T cells with VP plasma (10% concentration) inhibited IL-7-induced
STAT5 phosphorylation and its nuclear translocation. FIG. 5b shows the results obtained with five VP plasma samples. All at a 10% dilution inhibited the nuclear translocation of phospho-STAT5. These results were confirmed with plasmas from different VP (>15) and various sources of HD CD4 T cells (>5).

The effect of plasma derived from HIC and ART patients was also tested by pre-incubating these with purified HD CD4 T cells (FIGS. 5a and 5c). Here again, only VP plasma was able to inhibit the IL-7-induced nuclear translocation of phospho-STAT5. It was also determined (FIG. 5d) that VP plasma was active down to a 0.1% dilution, and half maximum activity was obtained at a 50 to 100 fold dilution, thus correlating with the ability to induce abnormal MMD (FIG. 4d).

The effect of plasma derived from ART-treated patients but non-responsive (CD4-NR) to their treatment (low count of viral RNA and low count of CD4 T-cells) was also tested by pre-incubating these with purified HD CD4 T cells. Here again, only CD4-NR plasma was able to inhibit the IL-7-induced nuclear translocation of phospho-STAT5. It was also determined that CD4-NR plasma was active down to a 0.1% dilution, and half maximum activity was obtained at a 50 to 100 fold dilution, thus correlating with the ability to induce abnormal MMD as observed with VP.

Example 8: Molecular Characterization of the Refractory State Inducing Factor

The chemical nature of RIF was investigated. The studies performed (FIG. 6a) showed that RIF is a protein since its activity was destroyed by trypsin. Treatment with peptide N-glycanase (PNGase) had no effect, indicating that N-glycosylation is not required for RIF activity.

The molecular weight of RIF was then measured by size-exclusion chromatography on Sephadex G-100. Induction of MMD (FIG. 6b) and inhibition of IL-7-induced phospho-STAT5 nuclear translocation (FIG. 6c) was measured for all fractions eluted from the column. Two representative column profiles are given in FIG. 6. Both show that RIF is a single factor with a MW between 10 and 15 kDa.

FIG. 6b shows the densities of the viral peptides or proteins measured by dot blot in each of the 100 fractions collected from the Sephadex G100 column. Measurements were repeated three times with different polyclonal antibodies from VP plasma samples characterized by their high activity against viral proteins. For each experiment the signals obtained with HD plasmas were then subtracted from the values. The pattern shown in FIG. 6b demonstrates that no viral proteins or fragments were detected in the fraction containing RIF activity while the dot blot assay was able to detect viral proteins at higher MW (from 190 to 32 kDa).

Ten to 15 kDa active, enriched fractions from the Sephadex G100 columns were then used to frame the isoelectric point of RIF by retention on anion (MonoQ) or cation (MonoS) exchange columns followed by pH elution (pH increase with MonoS or pH decrease with MonoQ) (FIG. 6d). The MMD-inducing activity of the various pH fractions was then measured after adjusting their pH to 7.4. In all, 25 to 30% of the initial activity was recovered in two fractions, a result consistent with an isoelectric point of 6.5 to 8.0.

RIF is therefore a secreted protein, with a MW of about 15 kDa, a pI around 7.5-8.0, which contains disulfide bridge. Following the above structural and functional features, RIF identity was directly obtained. In particular, amongst all of the 36853 known human proteins, 62 only had the above four characteristics of RIF. Semi-purified material prepared from three viremic patients and three HD were analyzed using mass spectrometry and standard Mascot program. Proteins recovered were ranked according to the p score described in Materials and Methods. The results shown in Table 1 below clearly and directly indicate that RIF is GIBsPLA2.

GIBsPLA2, more specifically the secreted form thereof. The amino acid sequence of a human GIBsPLA2 is provided as SEQ ID NO: 2.

Example 9: PLA2sGIB Induces Unresponsiveness (Anergy) of CD4 Lymphocytes

Example 7 shows that PLA2sGIB, through induction of aMMD, induces a blockade of IL-7-induced nuclear translocation of phospho STAT5 (NT pSTAT5). Consequently, CD4 T lymphocytes do not respond to IL-7 and despite of the high level of this cytokine in the plasma of HIV patients, their number decreases then leading to CD4 lymphopenia the hallmark of HIV-infected patients.

Here we investigated the possibility that PLA2sGIB also participates to the induction of anergy, another characteristic of the CD4 lymphocytes from chronically HIV-infected patients.

Bioassay

MMD Induction:

VP plasma containing PLA2sGIB was first incubated (20 min) in medium with purified HD CD4 T cells. The cells were then plated on polylysine-coated glass slides for an additional 10 min. They were then fixed with paraformaldehyde (PFA, 1.5%, 15 min at 37° C. followed by 15 min at room temperature) before being stained by cholera toxin B (CtxB-AF488), MMD were counted by CW-STED microscopy.

Inhibition of STAT Phosphorylation and Nuclear Translocation:

VP plasma containing PLA2sGIB was first incubated with purified HD CD4 T cells (20 min) before stimulation by IL-7 (2 nM, 15 min.). Cells were then plated on polylysine coated glass slides before fixation by PFA (1.5%) and permeabilization by methanol (90% at −20° C.). pSTAT5 was then stained by rabbit anti-STAT5 labelled with goat anti-rabbit-Atto642 and analyzed by FACS or pulsed STED microscopy.

Results

FIG. 10a shows that after exposition to PLA2 GIB (plasma of viremic patient), CD4 lymphocytes from healthy

TABLE 1

| Mnemonic | ID | PI | MW | i_s | p_score | description |
|---|---|---|---|---|---|---|
| PA21B_HUMAN | P04054 | 7.95 | 14138.99 | 9 | 0.64 | phospholipase A2 group 1 |
| TMEM9_HUMAN | Q9P0T7 | 6.23 | 18568.37 | 5 | 0.29 | Transmembrane protein 9 (TM) |
| ESM1_HUMAN | Q9NQ30 | 6.83 | 18122.42 | 5 | 0.10 | Endothelial cell-spe molecule 1 |
| CYTD_HUMAN | P28325 | 6.76 | 13858.6 | 3 | 0.08 | Cystatin-D |
| SSRB_HUMAN | P43308 | 7.03 | 18273.74 | 7 | 0.05 | Signal seq R sub beta (TM) |
| GPIX_HUMAN | P14770 | 6.14 | 17316.06 | 6 | 0.04 | Platelet glycoprotein IX |
| B2MG_HUMAN | P61769 | 7.67 | 18510.47 | 4 | 0.03 | Beta-2-microglobulin |
| EPGN_HUMAN | Q6UW09 | 7.72 | 14724.99 | 1 | 0.02 | Epigen |
| IL19_HUMAN | Q9UHD0 | 7.8 | 17812.56 | 5 | 0.02 | Interleukin-19 |
| IL3_HUMAN | P08700 | 7.05 | 15091.38 | 3 | 0.02 | Interleukin-3 |
| GML_HUMAN | Q99445 | 6.67 | 15918.41 | 7 | 0.02 | Glycosyl-PPI-anc like protein |
| CYTM_HUMAN | P05113 | 7.02 | 13149.22 | 4 | 0.017 | Cystatin-M |

The protein found in the plasma of viremic patients is thus the secreted form of GIBsPLA2. The mature protein has 125 aa (MW14138), PI 7.95 and 7 disulfide bridges. Using commercial purified porcine GIBsPLA2, we were able to verify in vitro that this protein induces abnormal MDM, which block IL-7 pSTAT5 nuclear translocation in the plasma of viremic patients, further confirming that RIF is donors (HD) become unable to respond to IL-2, as measured by the inhibition of the IL-2-induced NT pSTAT5. This inhibition is total with 3% plasma, and highly significant with 1% plasma (p<0.0001).

We further studied the response of CD4+ CD25+ T reg lymphocytes to PLA2 GIB. The results are presented in FIG. 10b. As illustrated, while 100% of healthy cells respond to IL-2 by NT pSTAT5, PLA2 GIB (1% plasma of viremic patients) completely inhibited this signal transduction mechanism. Since CD4+ CD25+ cells represent less than 5% of total CD4 T cells, they cannot significantly influence the data presented in FIG. 10a.

IL-7 and IL-2 are members of the gamma c cytokine family. To confirm that unresponsiveness to this cytokine may be linked to gamma c, we tested the response to IL-4. IL-4 response was measured by following the IL-4 induced NT of pSTAT6 (FIG. 11). Our results clearly show that IL-4 response is inhibited by PLA2 GIB (completely with 3% plasma and greatly with 1% plasma).

These results therefore show that the signaling mechanisms induced by cytokines of the gamma c family are altered by PLA2 GIB. This is in complete agreement with our finding that gamma c receptor chain is found completely sequestered in aMMD spontaneously found at the surface of CD4 lymphocytes from HIV-patients (data not shown).

Example 10: Activity of Recombinant Forms of PLA2 GIB

In this example, the activity of various purified forms of PLA2 GIB proteins was tested, to further confirm the effect of this protein in purified form on the immune system, and to further confirm its specificity.

Enzymatic Assay

The assay was performed with the Enz Check PLA2 assay kit from Life Technologies (ref.: E102147). This assay provides a continuous rapid real-time monitoring of PLA2 enzyme activities. The PLA2 activity is followed by the intensity increase of a single wavelength at 515 nm. PLA2 is detected by changes in the emission intensity ratio at 515/575 nm with excitation at 460 nm. Specific activities are expressed in amount of fluorescent substrate (U) obtained per second and per μg of enzyme in solution.

Results

The results are provided in Table 2 below.

TABLE 2

Activity of recombinant PLA2 GIB proteins

| PLA2 | Nature | Initial concentration (mg/ml) | Final concentration (ug/ml) | Quantity (ug) | Specific activity (U/ug/s) |
|---|---|---|---|---|---|
| ppPLA2 IB | Purified porcine pancreas | 2.90 | 0.58 | 0.06 | 7694.31 |
| pPLA2 IB | recombinant porcine (in E. coli) | 1.40 | 2.80 | 0.14 | 10353.57 |
| hPLA2 IB | recombinant human (in E. coli) | 0.70 | 1.40 | 0.07 | 10694.57 |
| hPLA2 IIA | recombinant human (in E. coli) | 1.45 | 2.90 | 0.15 | 214.93 |
| hPLA2 IID | recombinant human (E. coli) | 0.70 | 1.40 | 0.07 | 445.21 |
| hPLA2 X | recombinant human (in E. coli) | 0.68 | 1.36 | 0.07 | 3318.97 |

The results show that recombinant human PLA2 GIB produced in E. Coli exhibit a potent enzymatic activity. Furthermore, the results also show that recombinant porcine PLA2GIB produced in E. Coli has a specific activity similar to that of recombinant human PLA2GIB. By contrast, recombinant PLA2GIIA and PLA2GIID are not active and PLA2GX has a very limited activity.

Recombinant PLA2 GIB thus represents a potent active agent for use in the present invention.

Example 11: The Effects of PLA2sGIB on CD4 Lymphocytes Involve its Enzymatic Activity In this example, we investigated whether the activity of PLA2sGIB on CD4 lymphocytes involved (e.g., was a consequence of) an enzymatic (e.g., catalytic) activity of PLA2sGIB. Such enzymatic activity would modify the membrane structure leading to the formation of multiple aMMD at the surface of CD4 lymphocytes.

In these experiments, we tested a mutant of PLA2sGIB where a critical histidine at position 48 was replaced by glutamine (mutant H48Q). Using the enzymatic test described in example 10, we compared the enzymatic activity of recombinant porcine PLA2 GIB produced in E. coli with the activity of mutant H48Q also produced in E. Coli. Each protein was used at 200 microM. As shown FIG. 12, the mutant has lost all of its enzymatic activity, illustrating the critical role of histidine at position 48 in PLA2 GIB.

We then compared the activity of wild type porcine PLA2 GIB with its mutant H48Q in a bioassay. The results presented in FIG. 13 show that the mutant has lost the ability of wtPLA2 GIB to induce aMMD or to reduce or abrogate IL-7 induced Nuclear Translocation of pSTAT5 (NT pSTAT5).

These results thus demonstrate that the enzymatic activity is involved in the pathogenic effects of PL2 GIB on CD4 lymphocytes.

Example 12: Anti-GIBsPLA2 Antibodies Restore CD4-T Cell Activity in the Plasma of HIV Viremic Patients This example illustrates that, in the plasma of viremic patients, GIBsPLA2 transforms CD4 lymphocytes from HD into "sick" lymphocytes comparable to those characterized in the blood of HIV-infected patients. This example further shows that anti-GIBsPLA2 antibodies do effectively suppress the pathogenic activity.

In a first series of experiments, the plasma were treated by sepharose beads coated either by goat antibodies directed against human GIBsPLA2 or by two control goat antibodies directed against non relevant antigens. FIG. 14(a) clearly shows that anti-GIBsPLA2 antibodies completely abolished or removed the activity of the plasma, which became unable to induce abnormal MMD in CD4 lymphocytes from HD. Control I and control II antibodies had no effect. These experiments were repeated three times for each plasma and three different plasma from viremic patients were studied.

FIG. 14(*b*) shows identical results. Here the plasma were treated as above but were analyzed using the second bioassay. The plasma treated by sepharose beads coated with anti-GIBsPLA2 antibodies do not inhibit anymore IL-7-induced pSTAT5 nuclear translocation. Control I and control II goats antibodies did not affect the ability of the plasma from viremic patients to inhibit IL-7 induced pSTAT5 nuclear translocation.

In a second series of experiments, we tested the effects of neutralizing rabbit antibodies specifically directed against human GIBsPLA2, -GIIA and -GIID. These antibodies were incubated with the plasma and the cells during the bio assays. The results obtained show that anti-GIBsPLA2 antibodies neutralize the effects of the viremic plasma as measured by the induction of abnormal MMD and by inhibition of IL-7-induced pSTAT5 nuclear translocation. It is noteworthy that antibodies directed against secreted PLA2-GIIA or secreted PLA2-GIID, two phospholipases which are closely related to GIBsPLA2, had no effect in this test.

These results show that anti-GIBsPLA2 antibodies can revert and prevent the immunosuppressive effect of viremic plasma. These results show that anti-GIBsPLA2 antibodies can prevent immunodeficiency and restimulate the immune response in immuno-defective subjects.

These results further demonstrate that the response is specific. GIBsPLA2 is the only effector involved in the pathogenic effect examined and characterizing the plasma of viremic patients.

Example 13: Anti-PLA2GIB Antibodies Inhibit PLA2 GIB Effects on CD4 Cells

Cloned and purified human PLA2G1B was used to immunize rabbits. Immunoglobulin fractions of the corresponding sera were prepared. Their capacity to inhibit the enzymatic activity of PLA2G1B was measured on radiolabelled *E. coli* membranes. Active immunoglobulin fractions were added to the bioassay including CD4 Lymphocytes purified from the blood of healthy donors. Cloned and purified secreted PLA2 (GIB, GIIA, GIID and GX) were subsequently added to the cultures. As controls immunoglobulin fractions prepared from rabbits immunized with various secreted PLA2 were used FIG. 15 show that different concentrations of polyclonal antibody inhibit the induction of aMMD (FIG. 15*a*) and block the IL-7-induced NT pSTAT5 (FIG. 15*b*). This activity can be obtained from 1 µg/ml to 100 µg/ml of Ig containing anti-PLA2 GIB antibodies. This activity is totally specific since antibodies directed against PLA2 GIIA, PLA2GIID or PLA2GX showed no effect in the bioassay (FIGS. 15 *a* and *b*).

These results thus further demonstrate that inhibiting PLA2GIB can be used to treat immunodeficiencies and to restore CD4 activity.

Example 14: Soluble PLA2GIB Receptor Inhibits PLA2 GIB Effects on CD4 T Cells As a further demonstration that inhibitors of PLA2GIB can exert therapeutic effect, we tested a soluble form of a PLA2GIB receptor.

In a first series of experiment, we used, the soluble murine receptor specific for PLA2 GIB having the following amino acid sequence (SEQ ID NO: 22):

MVQWLAMLQLLWLQQLLLLGIHQGIAQDLTHIQEPSLEWRDKGIFIIQSE

SLKTCIQAGKSVLTLENCKQPNEHMLWKWVSDDHLFNVGGSGCLGLNISA

LEQPLKLYECDSTLISLRWHCDRKMIEGPLQYKVQVKSDNTWARKQIHRW

IAYTSSGGDICEHPSRDLYTLKGNAHGMPCVFPFQFKGHWHHDCIREGQK

EHLLWCATTSRYEEDEKWGFCPDPTSMKVFCDATWQRNGSSRICYQFNLL

SSLSWNQAHSSCLMQGGALLSIADEDEEDFIRKHLSKWKEVWIGLNQLDE

KAGWQWSDGTPLSYLNWSQEITPGPFVEHHCGTLEWSAAWRSRDCESTLP

YICKRDLNHTAQGILEKDSWKYHATHCDPDWTPFNRKCYKLKKDRKSWLG

ALHSCQSNDSVLMDVASLAEVEFLVSLLRDENASETWIGLSSNKIPVSFE

WSSGSSVIFTNWYPLEPRILPNRRQLCVSAEESDGRWKVKDCKERLFYIC

KKAGQVPADEQSGCPAGWERHGRFCYKIDTVLRSFEEASSGYYCSPALLT

ITSRFEQAFITSLISSVAEKDSYFWIALQDQNNTGEYTWKTVGQREPVQY

TYWNTRQPSNRGGCVWRGGSSLGRWEVKDCSDFKAMSLCKTPVKIWEKTE

LEERWPFHPCYMDWESATGLASCFKVFHSEKVLMKRSWREAEAFCEEFGA

HLASFAHIEEENFVNELLHSKFNWTQERQFWIGFNRRNPLNAGSWAWSDG

SPWSSFLDNAYFEEDAKNCAVYKANKTLLPSNCASKHEWICRIPRDVRPK

FPDWYQYDAPWLFYQNAEYLFHTHPAEWATFEFVCGWLRSDFLTIYSAQE

QEFIHSKIKGLTKYGVKWWIGLEEGGARDQIQWSNGSPVIFQNWDKGREE

RVDSQRKRCVFISSITGLWGTENCSVPLPSICKRVKIWVIEKEKPPTQPG

TCPKGWLYFNYKCFLVTIPKDPRELKTWTGAQEFCVAKGGTLVSIKSELE

QAFITMNLFGQTTNVWIGLQSTNHEKWVNGKPLVYSNWSPSDIINIPSYN

TTEFQKHIPLCALMSSNPNFHFTGKWYFDDCGKEGYGFVCEKMQDTLEHH

VNVSDTSAIPSTLEYGNRTYKIIRGNMTWYAAGKSCRMHRAELASIPDAF

HQAFLTVLLSRLGHTHWIGLSTTDNGQTFDWSDGTKSPFTYWKDEESAFL

GDCAFADTNGRWHSTACESFLQGAICHWTETKAFEHPGLCSETSVPWIKF

KGNCYSFSTVLDSRSFEDAHEFCKSEGSNLLAIRDAAENSFLLEELLAFG

SSVQMVWLNAQFDNNNKTLRWFDGTPTEQSNWGLRKPDMDHLKPHPCWLR

IPEGIWHFTPCEDKKGFICKMEAGIPAVTAQPEKGLSHSIVPVTVTLTLI

IALGIFMLCFWIYKQKSDIFQRLTGSRGSYYPTLNFSTAHLEENILISDL

EKNTNDEEVRDAPATESKRGHKGRPICISP

The inhibitor was tested in the bioassay described in example 9, at a concentration of 100 nM. The results are presented in FIG. 16. They show that a recombinant PLA2 soluble receptor can be used as a potent antagonist and that such molecule is able to significantly block the negative effect of PLA2sGIB on the NT of pSTAT5 (FIG. 16).

Similar results can be obtained in further sets of experiments using PLA2-GIB-binding polypeptides comprising the sequence of SEQ ID NO: 25 or 28.

Example 15: Overexpression of GIBsPLA2 Induces Immunological Deficiency

It has been previously shown that Highly Active Anti-Retroviral Therapy (HAART) which reduced viral load also induces a CD4 count increase in most patients. However, in some patients, despite the fact that HIV becomes undetectable, the CD4 counts do not increase. We have previously studied this clinical situation and we have shown that in these patients called CD4 Non Responders (CD4-NR) a strong and persistent defects of the CD4 T lymphocytes population is found.

FIG. 17 shows that the plasma of CD4-NR patients do contains more PLA2 GIB activity than plasma from a viremic patient taken as control. This was first measured by the induction of abnormal MMD per cells. These data were also confirmed by measuring the ability to inhibit IL-7-induced pSTAT5 nuclear translocation.

Altogether, the results show that the plasma of CD4-NR patients contains hundred times more PLA2 GIB activity than the plasma from viremic patients.

Discussion

Our results show that PLA2 GIB induces an immunosuppression similar to that which characterizes CD4 T cells from viremic patients, including the inability to respond to IL-2 (anergy) and to IL-7 (central mechanism towards CD4 lymphopenia). Therefore, expression of GIBsPLA2 during HIV infection plays a central role in the pathophysiology of the immune disease that characterizes these patients. These defects are cell-type specific since CD8 T lymphocytes from HIV patients do not exhibit abnormal MMD and continue to respond to IL-7 (data not shown). The mode of action of PLA2 GIB is probably the consequence of its enzymatic activity. By attacking the membrane of CD4 lymphocyte, it modifies its fluidity and probably allows the formation of abnormal and very large MMD.

Inflammatory reactions play an important role during HIV infection. However, their exact role in HIV pathogenesis remains to be elucidated. Taking into account our data, one can hypothesize that HIV infection induces a very peculiar type of inflammation which includes GIBsPLA2. Furthermore, one can speculate that after PLA2 GIB induction, its secretion escape to normal regulatory processes therefore leading to a chronic production and to the immunological disorders which are the direct consequence of the CD4 T lymphocytes dysfunction. As an indirect consequence of the CD4 T lymphocytes dysfunction, other defects can also be observed. For instance, diminished production of Interferon gamma will decrease the functions of monocytes/macrophages and of natural killers.

Correlation between the recovery of plasmatic PLA2 GIB activity and the characteristics of different groups of patients is also very informative. "HIV controllers" are very rare patients which maintain an undetectable viral load and quasi normal CD4 counts over the years. Our results show that they do not express PLA2 GIB activity in their plasma. By contrast, in most patients, this enzyme is expressed and represents the negative side of the inflammation which leads to the immunological disease. Altogether, this clearly establishes that PLA2 GIB is a very critical parameter in the pathophysiology of HIV infection.

HAART viral load decrease is followed by an immune restoration including CD4 counts increase. During this treatment, PLA2 GIB activity disappears in the plasma of the patients. Since, HAART is considered to decrease the inflammatory reactions this further suggests that PLA2 GIB is part of these inflammatory processes. More importantly, we describe here the case of the CD4-NR patients which remain with very low CD4 counts while HAART control their viral load. The overproduction of PLA2 GIB found in these individuals may explain the persistence of the immune disease that characterizes this clinical status. Therefore, after HAART, there is a strong correlation between the decrease production of PLA2 GIB leading to immune restoration or its persistent overproduction leading to the irreversibility of the immune disease.

The therapeutic consequences and utilities of this discovery are huge. Inhibition of PLA2 GIB may indeed be used to prevent or cure the immunological disease of HIV patients as well as, more generally, of immunodepressed subjects. Applied early during infection, inhibitors of PLA2 GIB lead the patients toward a HIV controller status. Applied later, alone or in conjunction/alternance with HAART, they accelerate the recovery of the CD4 T lymphocytes functions and by boosting host defenses, inhibitors of PLA2 GIB lead to an equilibrium between the virus and the immune system like in many other viral chronic infection. Therefore, inhibitors of PLA2 GIB represent very potent agents for use, alone or in combination, to treat disorders associated with an abnormal immune response or activity. They can also help in sparing HAART and could lead to the interruption of these treatments which are known for their severe detrimental effects.

Furthermore, since a lack of GIBsPLA2 expression (as in mice KO for the corresponding gene) is well tolerated, transient or permanent suppression of GIBsPLA2 using inhibitors or through vaccination, represents a strong and valid immunotherapy of immune diseases, particularly HIV patients.

REFERENCES (1) Grossman Z, Meier-Schellersheim M, Sousa A E, Victorino R M M, Paul W E (2002) CD4+ T-cell depletion in HIV infection: are we closer to understanding the cause? *Nat Med* 8(4):319-323
(2) Catalfamo M, et al. (2008) HIV infection-associated immune activation occurs by two distinct pathways that differentially affect CD4 and CD8 T cells. *PNAS* 105(50): 19851-19856.
(3) Armah K A, et al. (2012) HIV status, burden of comorbid disease and biomarkers of inflammation, altered coagulation, and monocyte activation. *Clin Infec Dis* 55(1)126-36.
(4) David D, et al. (1998) Regulatory dysfunction of the Interleukin-2 receptor during HIV-infection and the impact of triple combination therapy. *PNAS* 95:11348-11353.
(5) Colle J H, et al. (2006) Regulatory dysfunction of the interleukin-7 receptor in CD4 and CD8 lymphocytes from HIV-infected patients—effects of antiretroviral therapy. *J Acquir Immune Defic Syndr* 42(3):277-285.
(6) Kryworuchko M, Pasquier V, Thèze J (2003). Human Immunodeficiency Virus-1 envelope glycoproteins and anti-CD4 antibodies inhibit Interleukin-2 induced Jack/STAT signaling in human CD4 T lymphocytes. *Clinical and Experimental Immunology* 131(3):422-427.
(7) Landires I, et al. (2011) HIV infection perturbs IL-7 signaling at the step of STAT5 nuclear relocalization. *AIDS* 25(15):1443-1453.
(8) Vranjkovic A, Crawley A M, Patey A, Angel J B (2011) IL-7 dependent STAT-5 activation and CD8+ T cell proliferation are impaired in HIV infection. *J Leukoc Biol* 89(4):499-506.
(9) Benoit A, et al. (2009) Inverse association of repressor growth factor independent-1 with CD8 T cell interleukin (IL)-7 receptor [alpha] expression and limited signal transducers and activators of transcription signaling in response to IL-7 among [gamma]-chain cytokines in HIV patients. *AIDS* 23(11):1341-7.
(10) Rose T, et al. (2010) Interleukine-7 compartimentilizes its receptor signaling complex to initiate CD4 T lymphocyte response. *J Biol Chem* 285(20):14898-14908.

(11) Lingwood D, Simons K (2010) Lipid rafts as a membrane-organizing principle. *Science* 327(5961):46-50.
(12) Tamarit B, et al. (2013) Membrane microdomains and cytoskeleton organisation shape and regulate the IL-7-receptor signalosome in human CD4 T-cells. *J Biol Chem.*
(13) Beq S, et al. (2004) HIV infection: pre-highly active antiretroviral therapy IL-7 plasma levels correlate with long term CD4 cell count increase after treatment. *AIDS* 18(3):563-5.
(14) Rose T, Lambotte O, Pallier C, Delfraissy J F, Colle J H (2009) Identification and biochemical characterization of human plasma soluble IL-7R: lower concentrations in HIV-1 infected patients. *J Immunol* 182(12):7389-97.
(15) Sauce D, Elbim C, Appay V (2013) Monitoring cellular immune markers in HIV infection: from activation to exhaustion. *Curr Opin HIV AIDS* 8:125-131.
(16) Younes S A, et al. (2003) HIV-1 viremia prevents the establishment of interleukin-2 producing HIV-specific memory $CD4^+$ T cells endowed with proliferative capacity. *J Exp Med* 198:1909-1922.
(17) Sirskyj D, Thèze J, Kumar A, Kryworuchko M (2008) Disruption of the gamma c cytokine network in T cells during HIV infection. *Cytokine* 43(1):1-14.
(18) Pallikkuth S, Parmigiani A, Pahwa S (2012) The role of interleukin-21 in HIV infection. *Cytokine* 23(4-5):173-80.
(19) Vingert B, et al. (2012) HIV Controllers maintain a population of highly efficient TH1 effector in contrast to patients treated in the long term. *J Virol* 86(19):10661-10674.
(20) Sandler N G, Douek D C (2012) Microbial translocation in HIV infection: causes, consequences and treatment opportunities. *Nat Rev Microbiol* 10(9):655-66.

The invention claimed is:

1. A method for stimulating an immune response in a subject having a disorder associated with a CD4 T cell immune deficiency, or for treating a disorder associated with a CD4 T cell immune deficiency in a subject, comprising administering to the subject an effective amount of an inhibitor of secreted phospholipase A2 group IB (GIBsPLA2), said GIBsPLA2 inhibitor being:
   a) a polyclonal antibody that binds to GIBsPLA2 or a GIBsPLA2-binding fragment of said polyclonal antibody, said polyclonal antibody or GIBsPLA2-binding fragment thereof inhibiting a GIBsPLA2 enzymatic activity, wherein said GIBsPLA2 is a protein comprising amino acid residues 23-148 of SEQ ID NO: 2 or a naturally-occurring variant thereof; or
   b) a soluble GIBsPLA2-binding protein comprising a sequence selected from any one of SEQ ID NOs: 22-31.

2. The method of claim 1, wherein said method induces or stimulates CD4 T cells activation in the subject.

3. The method of claim 1, wherein the CD4 T cell immune deficiency is caused by a viral infection.

4. The method of claim 3, wherein the viral infection is an HIV infection.

5. The method of claim 4, said method suppressing or reversing HIV-mediated immunodeficiency.

6. The method of claim 1, wherein the inhibitor is administered intramuscularly, subcutaneously, transdermally, intravenously, intraarterially, nasally, orally, mucosally, rectally or by inhalation.

7. The method of claim 1, wherein the polyclonal anti-GIBsPLA2 antibody or GIBsPLA2-binding fragment is human.

8. The method of claim 1, wherein the polyclonal anti-GIBsPLA2 antibody or GIBsPLA2-binding fragment thereof binds an epitope comprising an amino acid selected from amino acid 50, amino acid 52, amino acid 54, amino acid 70, amino acid 71, amino acid 121, or a combination thereof.

9. The method of claim 1, wherein the polyclonal anti-GIBsPLA2 antibody or GIBsPLA2-binding fragment thereof binds an epitope comprising amino acid residues 50-71 of GIBsPLA2.

10. The method of claim 1, wherein the polyclonal anti-GIBsPLA2 antibody or GIBsPLA2-binding fragment thereof inhibits an activity of GIBsPLA2 selected from induction of formation of membrane microdomains (MMD) in CD4 T cells from healthy subjects or rendering CD4 T cells of healthy subjects refractory to interleukin signaling.

11. A method for stimulating an immune response in a subject having a disorder associated with a CD4 T cell immune deficiency, or for treating a disorder associated with a CD4 T cell immune deficiency in a subject, comprising administering to the subject an effective amount of an inhibitor of secreted phospholipase A2 group IB (GIBsPLA2), said GIBsPLA2 inhibitor being a polyclonal antibody that binds to GIBsPLA2 or a GIBsPLA2-binding fragment thereof, said polyclonal GIBsPLA2-binding antibody or GIBsPLA2-binding fragment inhibiting a GIBsPLA2 enzymatic activity, wherein said GIBsPLA2 is a protein comprising amino acid residues 23-148 of SEQ ID NO: 2 or a naturally-occurring variant thereof.

12. The method according to claim 11, said method comprising stimulating an immune response in a subject having a disorder associated with a CD4 T cell immune deficiency, comprising administering to the subject an effective amount of an inhibitor of secreted phospholipase A2 group IB (GIBsPLA2), said GIBsPLA2 inhibitor being a polyclonal antibody that binds to GIBsPLA2 or a GIBsPLA2-binding fragment of said antibody, said polyclonal GIBsPLA2-binding antibody or GIBsPLA2-binding fragment inhibiting a GIBsPLA2 enzymatic activity.

13. The method according to claim 11, said method comprising treating a disorder associated with a CD4 T cell immune deficiency in a subject, comprising administering to the subject an effective amount of an inhibitor of secreted phospholipase A2 group IB (GIBsPLA2), said GIBsPLA2 inhibitor being a polyclonal antibody that binds to GIBsPLA2 or a GIBsPLA2-binding fragment of said antibody, said polyclonal GIBsPLA2-binding antibody or GIBsPLA2-binding fragment inhibiting a GIBsPLA2 enzymatic activity.

14. A method for stimulating an immune response in a subject having a disorder associated with a CD4 T cell immune deficiency, or for treating a disorder associated with a CD4 T cell immune deficiency in a subject, comprising administering to the subject an effective amount of an inhibitor of secreted phospholipase A2 group IB (GIBsPLA2), said GIBsPLA2 inhibitor being a soluble GIBsPLA2 binding protein comprising a sequence selected from any one of SEQ ID NOs: 22-31.

15. The method according to claim 14, said method comprising stimulating an immune response in a subject having a disorder associated with a CD4 T cell immune deficiency, comprising administering to the subject an effective amount of an inhibitor of secreted phospholipase A2 group IB (GIBsPLA2), said GIBsPLA2 inhibitor being a soluble GIBsPLA2 binding protein comprising a sequence selected from any one of SEQ ID NOs: 22-31.

16. The method according to claim 14, said method comprising treating a disorder associated with a CD4 T cell immune deficiency in a subject comprising administering to the subject an effective amount of an inhibitor of secreted phospholipase A2 group IB (GIBsPLA2), said GIBsPLA2 inhibitor being a soluble GIBsPLA2 binding protein comprising a sequence selected from any one of SEQ ID NOs: 22-31.

* * * * *

UNITED STATES PATENT AND TRADEMARK OFFICE
CERTIFICATE OF CORRECTION

PATENT NO. : 11,365,264 B2
APPLICATION NO. : 15/105042
DATED : June 21, 2022
INVENTOR(S) : Jacques Theze, Thierry Rose and Florence Bugault Page 1 of 1

It is certified that error appears in the above-identified patent and that said Letters Patent is hereby corrected as shown below:

In the Specification

Column 11,
Line 43, "group TB," should read --group IB,--.
Line 44, "group D3 is" should read --group IB is--.
Line 48, "group TB" designates" should read --group IB" designates--.

Column 35,
Line 6, "time TO" should read --time τ0--.

Column 42,
Line 5, "NTWAR" should read --NTVVAR--.
Line 10, "SKWKE" should read --SKVVKE--.
Line 11, "LEWSA" should read --LEVVSA--.
Line 22, "CVWRG" should read --CVVVRG--.
Line 26, "SPWSS" should read --SPVVSS--.
Line 40, "CHWTE" should read --CHVVTE--.
Line 43, "PCWLR" should read --PCVVLR--.

Signed and Sealed this
Fourth Day of April, 2023

Katherine Kelly Vidal
*Director of the United States Patent and Trademark Office*